(12) United States Patent
Tangri et al.

(10) Patent No.: US 8,741,576 B2
(45) Date of Patent: Jun. 3, 2014

(54) HETEROCLITIC ANALOGS AND RELATED METHODS

(75) Inventors: Shabnam Tangri, San Diego, CA (US); Alessandro Sette, La Jolla, CA (US); Glenn Ishioka, Solana Beach, CA (US); John D. Fikes, San Diego, CA (US)

(73) Assignee: Epimunne Inc., San Diego, CA (US)

( * ) Notice: Subject to any disclaimer, the term of this patent is extended or adjusted under 35 U.S.C. 154(b) by 1675 days.

(21) Appl. No.: 10/116,118

(22) Filed: Apr. 5, 2002

(65) Prior Publication Data

US 2003/0143672 A1 Jul. 31, 2003

Related U.S. Application Data

(63) Continuation-in-part of application No. PCT/US00/31856, filed on Nov. 20, 2000.

(60) Provisional application No. 60/166,529, filed on Nov. 18, 1999, provisional application No. 60/239,008, filed on Oct. 6, 2000.

(51) Int. Cl.
*G01N 33/00* (2006.01)
*G01N 33/53* (2006.01)
*C07K 4/04* (2006.01)
*A61K 38/03* (2006.01)
*C07K 4/00* (2006.01)

(52) U.S. Cl.
USPC ............ 435/7.1; 435/7.24; 530/333; 530/334

(58) Field of Classification Search
None
See application file for complete search history.

(56) References Cited

U.S. PATENT DOCUMENTS

| | | | |
|---|---|---|---|
| 4,235,877 A | 11/1980 | Fullerton | |
| 4,487,715 A | 12/1984 | Nitecki et al. | |
| 4,599,230 A | 7/1986 | Milich et al. | |
| 4,837,028 A | 6/1989 | Allen | |
| 5,013,548 A | 5/1991 | Haynes et al. | |
| 5,128,319 A | 7/1992 | Arlinghaus | |
| 5,200,320 A | 4/1993 | Sette et al. | |
| 5,503,829 A | 4/1996 | Ladant et al. | |
| 5,662,907 A | 9/1997 | Kubo et al. | |
| 5,736,142 A | 4/1998 | Sette et al. | |
| 5,783,567 A | 7/1998 | Hedley et al. | |
| 6,034,214 A | 3/2000 | Boon et al. | |
| 6,037,135 A | 3/2000 | Kubo et al. | |
| 6,632,435 B1 * | 10/2003 | Diamond ................... | 424/186.1 |
| 2002/0098197 A1 | 7/2002 | Sette et al. | |
| 2002/0168374 A1 | 11/2002 | Kubo et al. | |
| 2002/0177694 A1 | 11/2002 | Sette et al. | |
| 2003/0152580 A1 | 8/2003 | Sette et al. | |

FOREIGN PATENT DOCUMENTS

| | | |
|---|---|---|
| EP | 0 044 710 A1 | 1/1982 |
| EP | 0 429 816 A1 | 6/1991 |
| EP | 0 433 242 A1 | 6/1991 |
| EP | 0 378 881 B1 | 6/1993 |
| WO | WO 92/02543 A1 | 2/1992 |
| WO | WO 92/12996 A2 | 8/1992 |
| WO | WO 92/21033 A1 | 11/1992 |
| WO | WO 93/03764 A1 | 3/1993 |
| WO | WO 94/11738 A1 | 5/1994 |
| WO | WO 94/20127 A1 | 9/1994 |
| WO | WO 95/07707 A1 | 3/1995 |
| WO | WO 95/22317 A1 | 8/1995 |
| WO | WO 96/03140 A1 | 2/1996 |
| WO | WO 96/22067 A2 | 7/1996 |
| WO | WO 97/33602 A1 | 9/1997 |
| WO | WO 97/34617 A1 | 9/1997 |
| WO | WO 97/41440 A1 | 11/1997 |
| WO | WO 98/33888 | 8/1998 |
| WO | WO 99/45954 A1 | 9/1999 |
| WO | WO 01/00225 A1 | 1/2001 |
| WO | WO 01/36452 A2 | 5/2001 |

OTHER PUBLICATIONS

Guo et al. Nature. 1992, vol. 360, pp. 364-366.*
Celis et al. Mol. Immunol. 1994, vol. 31, No. 18, pp. 1423-1430.*
Ochoa-Garay et al. Mol. Immunol. 1997, vol. 34, No. 3, pp. 273-281.*
Karin et al. J. Exp. Med. 1994, vol. 180, pp. 2227-2237.*
Chaux et al. Int. J. Cancer. 1998, vol. 77, pp. 538-542.*
Valmori et al. J. Immunol. 1998, vol. 160, pp. 1750-1758.*
Alexander, J., et al., "Development of High Potency Universal DR-Restricted Helper Epitopes by Modification of High Affinity DR-Blocking Peptides," *Immunity* 1:751-761, Cell Press (1994).
Arndt, S.O., et al., "Selection of the MHC Class II-Associated Peptide Repertoire by HLA-DM," *Immunol Res.* 16:261-272, Humana Press (Dec. 1997).
Barouch, D., et al., "HLA-A2 Subtypes Are Functionally Distinct in Peptide Binding and Presentation," *J. Exp. Med.* 182:1847-1856, Rockefeller University Press (1995).
Bender, A., et al., "Improved methods for the generation of dendritic cells from nonproliferating progenitors in human blood," *J. Immunol. Methods* 196:121-135, Elsevier Science (1996).
Ben-Yedidia, T., and Arnon, R., "Design of peptide and polypeptide vaccines," *Curr. Opin. Biotechnol.* 8:442-448, Current Biology, Ltd. (1997).
Carbone, F.R., and Bevan, M.J., "Induction of Ovalbumin-Specific Cytotoxic T Cells by in Vivo Peptide Immunization," *J. Exp. Med.* 169:603-612, Rockefeller University Press (1989).
Carbone, F.R., et al., "Induction of Cytotoxic T Lymphocytes by Primary in Vitro Stimulation with Peptides," *J. Exp. Med.* 167:1767-1779, Rockefeller University Press (1988).

(Continued)

*Primary Examiner* — Gerald R Ewoldt
*Assistant Examiner* — Marianne DiBrino
(74) *Attorney, Agent, or Firm* — Sterne, Kessler, Goldstein & Fox, P.L.L.C.

(57) ABSTRACT

Heteroclitic analogs of Class I epitopes are prepared by providing conservative or semi-conservative amino acid substitutions at positions 3 and/or 5 and/or 7 of these epitopes. The analogs are useful in eliciting immune responses with respect to the corresponding wildtype epitopes.

12 Claims, 18 Drawing Sheets

(56) References Cited

OTHER PUBLICATIONS

Cassell, D., and Forman, J., "Linked Recognition of Helper and Cytotoxic Antigenic Determinants for the Generation of Cytotoxic T Lymphocytes," *Ann. N.Y. Acad. Sci.*532:51-60, New York Academy of Sciences (1991).

Deres, K., et al., "In vivo priming of virus-specific cytotoxic T lymphocytes with synthetic lipopeptide vaccine," *Nature*342:561-564, Nature Publishing Group (1989).

del Guercio, M-F., et al., "Potent immunogenic short linear peptide constructs composed of B cell epitopes and Pan DR T Helper Epitopes (PADRE) for antibody responses in vivo," *Vaccine*15:441-448, Elsevier Science (Mar. 1997).

DiBrino, M., et al., "Endogenous Peptides with Distinct Amino Acid Anchor Residue Motifs Bind to HLA-A1 and HLA-B8," *J. Immunol.* 152:620-631, American Association of Immunologists (1994).

DiBrino, M., et al., "The HLA-B14 Peptide Binding Site Can Accommodate Peptides with Different Combinations of Anchor Residues," *J. Biol. Chem.* 269:32426-32434, American Society for Biochemistry and Molecular Biology (1994).

Donnelly, J.J., et al., "DNA Vaccines," *Annu. Rev. Immunol.* 15:617-648, Annual Reviews Inc. (Apr. 1997).

Francis, M.J., et al., "Non-responsiveness to a foot-and-mouth disease virus peptide overcome by addition of foreign helper T-cell determinants," *Nature*330:168-170, Nature Publication Group (1987).

Fynan, E.F., et al., "DNA vaccines: Protective immunizations by parental, mucosal, and gene-gun inoculations," *Proc. Natl. Acad. Sci. USA*90:11478-11482, National Academy of Sciences (1993).

Gileadi, U., et al., "Effect of epitope flanking residues on the presentation of N-terminal cytotoxic T lymphocyte epitopes," *Eur. J. Immunol.* 29:2213-2222, Wiley-VCH Verlag GmbH (Jul. 1999).

Golvano, J., et at., "Polarity of immunogens: implications for vaccine design," *Eur. J. Immunol.* 20:2363-2366, VCH Verlagsgesellschaft mbH (1990).

Gulukota, K., et al., "Two Complementary Methods for Predicting Peptides Binding Major Histocompatibility Complex Molecules," *J. Mol. Biol.* 267:1258-1267, Academic Press Limited (Apr. 1997).

Hahn, Y.S., et al., "CD8$^+$T Cell Recognition of an Endogenously Processed Epitope is Regulated Primarily by Residues within the Epitope," *J. Exp. Med.* 176:1335-1341, Rockefeller University Press (1992).

Hahn, Y.S., et al., "Presentation of Viral Antigen to Class I Major Histocompatibility Complex-Restricted Cytotoxic T Lymphocyte. Recognition of an Immunodominant Influenza Hemagglutinin Site by Cytotoxic T Lymphocyte is Independent of the Position of the Site in the Hemagglutinin Translation Product," *J. Exp. Med.* 174:733-736, Rockefeller University Press (1991).

Hammer, J., et al., "Precise Prediction of Major Histocompatibility Complex Class II-Peptide Interaction Based on Peptide Side Chain Scanning," *J. Exp. Med.* 180:2353-2358, Rockefeller University Press (1994).

Hill, C.M., et al., "Exploration of Requirements for Peptide Binding to HLA DRB1*0101 and DRB1*0401," *J. Immunol.* 152:2890-2898, American Association of Immunologists (1994).

Huczko, E.L., et al., "Characteristics of Endogenous Peptides Eluted from the Class I MHC Molecule HLA-B7 Determined by Mass Spectrometry and Computer Modeling," *J. Immunol.* 151:2572-2587, American Association of Immunologists (1993).

Ishioka, G.Y., et al., "Class I MHC-restricted, peptide specific cytotoxic T lymphocytes generated by peptide priming in vivo," in *Vaccines90: Modern Approaches to New Vaccines Including Prevention of AIDS*, Brown, F., et al., eds., Cold Spring harbor Laboratory Press, Cold Spring Harbor, NY, pp. 7-11 (1990).

Ishioka, G.Y., et al., "Induction of Class I MHC-Restricted, Peptide-Specific Cytolytic T Lymphocytes by Peptide Priming in Vivo," *J. Immunol.* 143:1094-1100, American Association of Immunologists (1989).

Jardetzky, T.S., et al., "Peptide binding to HLA-DR1: a peptide with most residues substituted to alanine retains MHC binding," *EMBO J.* 9:1797-1803, Oxford University Press (1990).

Kast, W.M., et al., "Protection against lethal Sendai virus infection by in vivo priming of virus specific cytotoxic T lymphocytes with a free synthetic peptide," *Proc. Natl. Acad. Sci. USA*88:2283-2287, National Academy of Sciences (1991).

Kondo, A., et al., "Two distinct HLA-A *0101-specific submotifs illustrate alternative peptide binding modes," *Immunogenetics*45:249-258, Springer-Verlag (Jan. 1997).

Kubitscheck, U., et al., "Peptide Binding to Class I Molecules of the Major Histocompatibility Complex on the Surface of Living Target Cells," *Scand. J. Immunol.* 36:341-348, Blackwell Scientific Publications (1992).

Kubo, R.T., et al., "Definition of Specific Peptide Motifs for Four Major HLA-A Alleles," *J. Immunol.* 152:3913-3924, American Association of Immunologists (1994).

Kumar, A., et al., "'Universal T Helper Cell Determinants Enhance Immunogenicity of a *Plasmodium falciparum*Merozoite Surface Antigen Peptide," *J. Immunol.* 148:1499-1505, American Association of Immunologists (1992).

Lasarte, J-J., et al., "Induction of Cytotoxic T Lymphocytes in Mice against the Principal Neutralizing Domain of HIV-1 by Immunization with an Engineered T-Cytotoxic-T-Helper Synthetic Helper Peptide Construct," *Cell. Immunol.* 14/:211-218, Academic Press Inc. (1992).

Madden, D.R., et al., "The structure of HLA-B27 reveals nonamer self-peptides bound in an extended conformation," *Nature*353:321-325, Nature Publishing Group (1991).

Maier, R., et al., "Peptide motifs of HLA-A3, -A24, and -B7 molecules as determined by pool sequencing," *Immunogenetics*40:306-308, Springer-Verlag (1994).

Martinon, F., et al., "Immunization of Mice with Lipopeptides Bypasses the Prerequisite for Adjuvant,"*J. Immunol.* 149:3416-3422, American Association of Immunologists (1992).

Niedermann, G., et al., "Contribution of Proteasome-Mediated Proteolysis to the Hierarchy of Epitopes Presented by Major Histocompatibility Complex Class I Molecules," *Immunity*2:289-299, Cell Press (1995).

Niedermann, G., et al., "The specificity of proteasomes: impact on MHC class I processing and presentation of antigens," *Immunol. Rev.* 172:29-48, Munksgaard (Dec. 1999).

Nikolić-Žugić, J., and Carbone, F.R., "Peptide Presentation by Class-I Major Histocompatibility Complex Molecules," *Immunol. Res.* 10:54-65, S. Karger AG (1991).

O'Sullivan, D., et al., "Characterization of the Specificity of Peptide Binding to Four DR Haplotypes,"*J. Immunol.* 145:1799-1808, American Association of Immunologists (1990).

O'Sullivan, D., et al., "On the Interaction of Promiscuous Antigenic Peptides with Different DR Alleles," *J. Immunol.* 147:2663-2669, American Association of Immunologists (1991).

Panina-Bordignon, P., et al., "Universally immunogenic T cell eptiopes: promiscuous binding to human MHC class II and promiscuous recognition by T cells," *Eur. J. Immunol.* 19:2237-2242, VCH Verlagsgesellschaft mbH (1989).

Paz, P., et al., "Discrete Proteolytic Intermediates in the MHC Class I Antigen Processing Pathway and MHC I-Dependent Peptide Trimming in the ER," *Immunity*11:241-251, Cell Press (Aug. 1999).

Penna, A., et al., "Cytotoxic T Lymphocytes Recognize an HLA-A2-Restricted Epitope Within the Hepatitis B Virus Nucleocapsid Antigen," *J. Exp. Med.* 174:1565-1570, Rockefeller University Press (1991).

Pryjma, J., et al., "Induction and Suppression of Immunoglobulin Synthesis in Cultures of Human Lymphocytes: Effects of Pokeweed Mitogen and *Staphylococcus Aureus*Cowan I," *J. Immunol.* 124:656-661, Williams & Wilkins Co. (1980).

Rahemtulla, A., et al., "Normal development and function of CD8$^+$cells but markedly decreased helper cell activity in mice lacking CD4," *Nature*353:180-183, Nature Publishing Group (1991).

Rammensee, H-G., et al., "SYFPEITHI: database for MHC ligands and peptide motifs," *Immunogenetics*50:213-219, Springer-Verlag (Nov. 1999).

Reitermann, A., et al., "Lipopeptide Derivatives of Bacterial Lipoprotein Constitute Potent Immune Adjuvants Combined with or Covalently Coupled to Antigen or Hapten," *Biol Chem. Hoppe Seyler*370:343-352, Walter De Gruyter (1989).

(56) References Cited

OTHER PUBLICATIONS

Restifo, N. P., et al., "Antigen Processing in Vivo and the Elicitation of Primary CTL Responses," *J. Immunol.* 154:4414-4422, American Association of Immunologists (1995).
Saper, M.A., et al., "Refined Structure of the Human Histocompatibility Antigen HLA-A2 at 2.6 ÅResolution," *J. Mol. Biol.* 219:277-319, Academic Press Ltd. (1991).
Schaeffer, E.B., et al., "Relative contribution of 'determinant selection' and 'holes in the T-cell repertoire' to T-cell responses," *Proc. Natl. Acad. Sci. USA* 86:4649-4653, National Academy of Sciences (1989).
Schumacher, T.N.M., et al., "Peptide selection by MHC class I molecules," *Nature* 350:703-706, Nature Publishing Group (1991).
Sette, A., and Sidney, J., "HLA supertypes and supermotifs: a functional perspective on HLA polymorphism," *Curr. Opin. Immunol.* 10:478-482, Current Biology Publications (Aug. 1998).
Sette, A., et al., "A Novel Approach to the Generation of High Affinity Class II-Binding Peptides," *J. Immunol.* 145:1809-1813, American Association of Immunologists (1990).
Sette, A., et al., "Effect of Conformational Propensity of Peptide Antigens in Their Interaction with MHC Class II Molecules," *J. Immunol.* 143:1268-1273, American Association of Immunologists (1989).
Sette, A., et al., "Peptide Binding to the Most Frequent HLA-A Class I Alleles Measured by Quantitative Molecular Binding Assays," *Mol. Immunol.* 31:813-822, Pergamon Press (1994).
Sidney, J., et al., "Definition of an HLA-A3-Like Supermotif Demonstrates the Overlapping Peptide-Binding Repertoires of Common HLA Molecules," *Hum. Immunol.* 45:79-93, Elsevier Science Inc. (1996).
Sidney, J., et al., "Practical, biochemical and evolutionary implications of the discovery of HLA class I supermotifs,"*Immunol. Today* 17:261-266, Elsevier Science (1996).
Sidney, J., et al., "The HLA-A*0207 Peptide Binding Repertoire is Limited to a Subset of the A*0201 Repertoire," *Hum. Immunol.* 58:12-20, Elsevier Science Inc. (Nov. 1997).
Sinigaglia, F., and Hammer, J., "Defining rules for the peptide-MHC class II interaction," *Curr. Opin. Immunol.* 6:52-56, Current Biology Ltd. (1994).
Southwood, S., et al., "Several Common HLA-DR Types Share Largely Overlapping Peptide Binding Repertoires," *J. Immunol.* 160:3363-3373, American Association of Immunologists (Apr. 1998).
Sprent, J., and Schaefer, M., "Properties of Purified T Cell Subsets. I. In Vitro Responses to Class I vs. Class II H-2 Alloantigens," *J. Exp. Med.* 162:2068-2088, Rockefeller University Press (1985).
Stark, J.M., el al., "Immunogenicity of lipid-conjugated antigens. I. The Influence of Chain Length and Degree of Conjugation on Induction of Antibody in Mice," *Immunology* 39:345-352, Blackwell Scientific Publications (1980).
Steinman, R.M., "Dendritic cells and immune-based therapies," *Exp. Hematol.* 24:859-862, Elsevier Science Inc. (1996).
Sudo, T., et al., "Differences in MHC Class I Self Peptide Repertoires Among HLA-A2 Subtypes," *J. Immunol.* 155:4749-4756, American Association of Immunologists (1995).
Sugawara, S., et al., "A simple method to eliminate the antigenicity of surface class I MHC molecules from the membrane of viable cells by acid treatment at pH 3," *J. Immunol. Methods* 100:83-90, Elsevier Science (1987).
Tam, J.P., and Lu, Y-A., "Vaccine engineering: Enhancement of immunogenicity of synthetic peptide vaccines related to hepatitis in chemically defined models consisting of T-and B-cell epitopes," *Proc. Natl. Acad. Sci. USA* 86:9084-9088, National Academy of Sciences (1989).
Townsend, A., and Bodmer, H., "Antigen Recognition by Class I-Restricted T Lymphocytes," *Ann. Rev. Immunol.* 7:601-624, Annual Reviews, Inc. (1989).
von Boehmer, H., and Haas, W., "Distinct Ir Genes for Helper and Killer Cells in the Cytotoxic Response to H-Y Antigen," *J. Exp. Med.* 150:1134-1142, Rockefeller University Press (1979).

Watari, E., et al., "A Synthetic Peptide Induces Long-Term Protection from Lethal Infection with Herpes Simplex Virus 2," *J. Exp. Med.* 165:459-470, Rockefeller University Press (1987).
Wentworth, P.A., et al., "In Vitro Induction of Primary, Antigen-Specific CTL from Human Peripheral Blood Mononuclear Cells Stimulated with Synthetic Peptides," *Mol. Immunol.* 32:603-612, Elsevier Science Ltd. (1995).
Wherry, E.J., et al., "The Induction of Virus-Specific CTL as a Function of Increasing Epitope Expression: Responses Rise Steadily Until Excessively High Levels of Epitope Are Attained," *J. Immunol.* 163:3735-3745, American Association of Immunologists (Oct. 1999).
Widmann, C., et al., "T helper epitopes enhance the cytotoxic response of mice immunized with MHC class I-restricted malaria peptides," *J. Immunol. Meth.* 155:95-99, Elsevier Science Publishers B.V. (1992).
Wiesmüller, K-H., et al., "Lipopeptide-Helper-T-Cell Epitope-CTL Epitope Conjugate Induces Antibodies Against the CTL Epitope," *Innovation Perspective Solid Phase Synthesis Collect. Papers, Int. Symp. 2nd*, pp. 499-502 (1991).
Wiesmüller, K-H., et al., "Novel low-molecular-weight synthetic vaccine against foot-and mouth disease containing a potent B cell and macrophage activator," *Vaccine* 7:29-33, Butterworth & Co. (1989).
Yewdell, J.W., and Bennink, J.R., "Immunodominance in Major Histocompatibility Complex Class I-Restricted T Lymphocyte Responses," *Annu. Rev. Immunol.* 17:51-88, Annual Reviews Inc. (Apr. 1999).
Zhou, X., et al., "In vivo primary induction of virus-specific CTL by immunization with 9-mer synthetic peptides," *J. Immunol. Methods* 153:193-200, Elsevier Science Publishers B.V. (1992).
Zinkernagel, R.M., et al., "The Lymphoreticular System in Triggering Virus Plus Self-Specific Cytotoxic T Cells: Evidence for T Help," *J. Exp. Med.* 147:897-911, Rockefeller University Press (1978).
Bakker A.B.H., et al., "Analogues of CTL epitopes with improved MHC class-I binding capacity elicit anti-melanoma CTL recognizing the wild-type epitope." *Int. J. Cancer* 70:302-309 Wiley-Liss, Inc. (Jan. 1997).
De Magistris, M.T., et al., "Antigen Analog-Major Histocompatibility Complexes Act As Antagonists of the T Cell Receptor," *Cell* 68:625-634, Cell Press (1992).
Dyall, R., et al., "Heteroclitic Immunization Induces Tumor Immunity," *J. Exp. Med.* 188:1553-1561, Rockefeller University Press (Nov. 1998).
Aichele, P., et al., "Antiviral cytotoxic T cell response induced by in vivo priming with a free synthetic peptide," *J. Exp. Med.* 171:1815-1820, Rockefeller University Press (1990).
Alexander, J., et al., "Derivation of HLA-A11/$K^b$ Transgenic Mice. Functional CTL Repertoire and Recognition of Human All-Restricted CTL Epitopes," J. immunol. 159: 4753-4761, The American Association of Immunologists (Nov. 1997).
Bergmann, C.C., et al., "Differential Effects of Flanking Residues on Presentation of Epitopes from Chimeric Peptides," *J. Virol.* 68:5306-5310, American Society for Microbiology (Aug. 1994).
Bertoni, R., et al., "Human Histocompatibility Leukocyte Antigen-binding Supermotifs Predict Broadly Cross-reactive Cytotoxic T Lymphocyte Responses in Patients with Acute Hepatitis," *J. Clin. Invest.* 100:503-513. The American Society for Clinical Investigation, Inc. (Aug. 1997).
Bertoni, R., et al., "Human Class I Supertypes and CTL Repertoires Extend to Chimpanzees," *J. Immunol.* 161:4447-4455, American Association of Immunologists (Oct. 1998).
Bjorkman, P.J., et al., "Structure of the human class I histocompatibility antigen, HLA-A2," *Nature* 329:506-512, Macmillan Publishers, Ltd. (1987).
Bjorkman, P.J., et al., "The foreign antigen binding site and T cell recognition regions of class I histocompatibility antigens," *Nature* 329:512-518, Macmillan Publishers, Ltd. (1987).
Buus, S., et al., "Autologous Peptides Constitutively Occupy the Antigen Binding Site on Ia," *Science* 242:1045-1047, American Association for the Advancement of Science (1988).
Carreno, B.M., et al., "HLA-B37 and HLA-A2.1 molecules bind largely nonoverlapping sets of peptides," *Proc. Natl. Acad. Sci. USA* 87:3420-3424, National Academy Press (1990).

(56) References Cited

OTHER PUBLICATIONS

Corr, M., et al., "Endogenous Peptides of a Soluble Major Histocompatibility Complex Class I Molecule, H-2L$^d$,: Sequence Motif, Quantitative Binding, and Molecular Modeling of the Complex," *J. Exp. Med.* 176:1681-1692, Rockefeller University Press (Dec. 1992).
De Bruijn, M.L.H., et al., "Peptide loading of empty major histocompatibility complex molecules on RMA-S cells allows the induction of primary cytotoxic T lymphocyte responses," *Eur. J. Immunol.* 21:2963-2970, VCH Verlagsgesellschaft mbH (1991).
Del Val, M., et al., "Efficient Processing of an Antigenic Sequence for Presentation by MHC Class I Molecules Depends on Its Neighboring Residues in the Protein," *Cell* 66:1145-1153, Cell Press (1991).
Deres, K., et al., "In vivo priming of virus-specific cytotoxic T lymphocytes with synthetic lipopeptide vaccine," *Nature* 342:561-564, Macmillan Publishers, Ltd. (1989).
DiBrino, M., et al., "HLA-A1 and HLA-A3 T Cell Epitopes Derived from Influenza Virus Proteins Predicted from Peptide Binding Motifs," *J. Immunol.* 151:5930-5935, The Association of Immunologists (Dec. 1993).
DiBrino, M., et al., "Endogenous peptides bound to HLA-A3 possess a specific combination of anchor residues that permit identification of potential antigenic peptides," *Proc. Natl. Acad. Sci. USA* 90:15081512, National Academy Press (Feb. 1993).
Ding, Y.-H., et al., "Two Human T Cell Receptors Bind in a Similar Diagonal Mode to the HLA-A2/Tax Peptide Complex Using Different TCR Amino Acids," *Immunity* 8: 403-11, Cell Press (Apr. 1998).
Eisenlohr, L.C., et al., "Flanking Sequences Influence the Presentation of an Endogenously Synthesized Peptide to Cytotoxic T Lymphocytes," *J. Exp. Med.* 175:481-487, The Rockefeller University Press (Feb. 1992).
Engelhard, V.H., "Structure of peptides associated with MHC Class I molecules," *Curr. Opin. Immunol.* 6:13-23, Current Biology, Ltd. (Feb. 1994).
Falk, K., et al., "Allele-specific motifs revealed by sequencing of self-peptides eluted from MHC molecules," *Nature* 351:290-296, Macmillan Publishers, Ltd. (1991).
Falk, K., et al., "MHC peptide motif register. Peptide motifs of HLA-B35 and -B37 molecules," *Immunogenetics* 38:161-162, Springer-Verlag (Apr. 1993).
Falk, K., et al., "Allele-specific peptide ligand motifs of HLA-C molecules," *Proc. Natl. Acad. Sci. USA* 90:12005-12009, National Academy Press (Dec. 1993).
Falk, K., et al., "Pool sequencing of natural HLA-DR, DQ, and DP ligands reveals detailed peptide motifs, constraints of processing, and general rules," *Immunogenetics* 39:230-242, Springer-Verlag (Feb. 1994).
Falk, K., et al., "Peptide motifs of HLA-A1, -A11, -A31, and -A33 molecules," *Immunogenetics* 40:238-241, Springer-Verlag (Jul. 1994).
Foon, K.A., "Biological Response Modifiers: The New Immunotherapy," *Cancer Res.* 49:1621-1639, American Association for Cancer Research (1989).
Geysen, H.M., et al., "Cognitive Features of Continuous Antigenic Determinants," *J. Mol. Recognit.* 1:32-41, Heyden & Sons, Ltd. (1988).
Guo, H.-C., et al., "Different length peptides bind to HLA-Aw68 similarly at their ends but bulge out in the middle," *Nature* 360:364-366, Macmillan Publishers, Ltd. (Nov. 1992).
Henderson, R.A., et al., "HLA-A2.1-Associated Peptides from a Mutant Cell Line: A Second Pathway of Antigen Presentation," *Science* 255:1264-1266, American Association for the Advancement of Science (Mar. 1992).
Hill, A., et al., "Characterization of two Epstein-Barr virus epitopes restricted by HLA-B7," *Eur. J. Immunol.* 25:18-24, VCH Verlagsgesellschaft mbH (Jan. 1995).
Hunt, D.F., et al., "Characterization of Peptides Bound to the Class I MHC Molecule HLA-A2.1 by Mass Spectrometry," *Science* 255:1261-1263, American Association for the Advancement of Science (Mar. 1992).

Ishioka, G.Y., et al., "Utilization of MHC Class I Transgenic Mice for Development of Minigene DNA Vaccines Encoding Multiple HLA-Restricted CTL Epitopes," *J. Immunol.* 162:3915-3925, The American Association of Immunologists (Apr. 1999).
Jameson, S.C., and Bevan, M.J., "Dissection of major histocompatibility complex (MHC) and T cell receptor contact residues in a K$^b$-restricted ovalbumin peptide and an assessment of the predictive power of MHC-binding motifs," *Eur. J. Immunol.* 22:2663-2667, VCH Verlagsgesellschaft mbH (Oct. 1992).
Jardetzky, T.S., et al., "Identification of self peptides bound to purified HLA-B27," *Nature* 353:326-329, Macmillan Publishers, Ltd. (1991).
Kannagi, M., et al., "Target Epitope in the Tax Protein of Human T-Cell Leukemia Virus Type I Recognized by Class I Major Histocompatibility Complex-Restricted Cells," *J. Virol.* 66:2928-2933, American Society for Microbiology (May 1992).
Kest, W.M., et al., "Protection against lethal Sendai virus infection by in vivo priming of virus-specific cytotoxic T lymphocytes with a free synthetic peptide," *Proc. Natl. Acad. Sci. USA* 88:2283-2287, National Academy Press (1991).
East, W.M., et al., "Strict peptide length is not required for the induction of cytotoxic T lymphocyte-mediated antiviral protection by peptide vaccination," *Eur. J. Immunol.* 23:1189-1192, VCH Verlagsgesellschaft mbH (May 1993).
Krieger, J.I., et al., "Single amino acid changes in DR and antigen define residues critical for peptide-MHC binding and T cell recognition," *J. Immunol.* 146:2331-2340, American Association of Immunologists (1991).
Lipford, G.B., et al., "Primary in Vivo Responses to Ovalbumin. Probing the Predictive Value of the K$^b$ Binding Motif," *J. Immunol.* 150:1212-1222, The American Association of Immunologists (Feb. 1993).
Maryanski, J.L., at al., "Synthetic peptides as antigens and competitors in recognition by H-2-restricted cytolytic T cells specific for HLA," *J. Exp. Med.* 167:1391-1405, Rockefeller University Press (1988).
Maryanski, J.L., et al., "Competitor Analogs for Defined T Cell Antigens: Peptides Incorporating a Putative Binding Motif and Polyproline or Polyglycine Spacers," *Cell* 60:63-72, Cell Press (1990).
Morrison, J., et al., "Identification of the nonamer peptide from influenza A matrix protein and the role of pockets of HLA-A2 in its recognition by cytotoxic T lymphocytes," *Eur. J. Immunol.* 22:903-907, VCH Verlagsgesellschaft mbH (Apr. 1992).
Niedermann, G., at al., "The proteolytic fragments generated by vertebrate proteosomes: Structural relationships to major histocompatibility complex class I binding peptides," *Proc. Natl. Acad. Sci. USA* 93:8572-8577, National Academy Press (Aug. 1996).
Ochoa-Garay, J., et al., "The ability of peptides to induce cytotoxic T cells in vitro does not strongly correlate with their affinity for the H-2L$^d$ molecule: implications for vaccine design and immunotherapy," *Mol. Immunol.* 34:273-281, Elsevier Science, Ltd. (Feb. 1997).
Pamer, E.G., et al., "Precise prediction of a dominant class I MHC-restricted epitome of *Listeria monocytogenes*," *Nature* 353:852-855, Macmillan Publishers, Ltd. (1991).
Parham, P., et al., "The Origins of HLA-A,B,C Polymorphism," *Immunol. Rev.* 143:141-180, Munksgaard (Feb. 1995).
Parker, K.C., et al., "Peptide Binding to HLA-A2 and HLA-B27 Isolated from *Escherichia coli*," *J. Biol. Chem.* 267:5451-5459. American Society for Biochemistry and Molecular Biology, Inc. (Mar. 1992).
Parker, K.C., at al., "Sequence motifs important for peptide binding to the human MHC class I molecule, HLA-A2," *J. Immunol.* 149:3580-3587, American Association of Immunologists (Dec. 1992).
Rammensee, H.-G., et al., "Peptides Naturally Presented by MHC Class I Molecules," *Annu. Rev. Immunol.* 11:213-244, Annual Reviews, Inc. (Jan. 1993).
Rammensee, H.-G., et al., "MHC ligands and peptide motifs: first listing," *Immunogenetics* 41:178-228, Springer-Verlag (Feb. 1995).

(56) References Cited

OTHER PUBLICATIONS

Reddehase, M.J., et al., "A pentapeptide as minimal antigenic determinant for MHC class I-restricted T lymphocytes," *Nature* 337:651-653, Macmillan Publishers, Ltd. (1989).
Romero, P., et al., "H-2K$^d$-restricted Antigenic Peptides Share a Simple Binding Motif," *J. Exp. Med.* 174:603-612, Rockefeller University Press (1991).
Rothbard, J.B., "Major histocompatibility complex-peptide interections," *Curr. Opin. Immunol.* 2:99-105, Current Biology, Ltd. (1989).
Rötzschke, O., at al., "Isolation and analysis of naturally processed viral peptides as recognized by cytotoxic T cells," *Nature* 348:252-254, Macmillan Publishers, Ltd. (1990).
Rötzschke, O., at al., "Characterization of Naturally Occurring Minor Histocompatibility Peptides Including H-4 and H-Y," *Science* 249:283-287, American Association for the Advancement of Science (1990).
Rötzschke, O., and Falk, K., "Naturally-occurring peptide antigens derived from the MHC class-I-restricted processing pathway," *Immunol. Today* 12:447-455, Elsevier Science Publishers, Ltd. (1991).
Rotzschke, O., et al., "Peptide motifs of closely related HLA class I molecules encompass substantial differences," *Eur. J. immunol.* 22:2453-2456, VCH Verlagsgesellschaft mbH (Sep. 1992).
Rötzschke, O., and Falk, K., "Origin, structure and motifs of naturally processed MHC class II ligands," *Curr. Opin. immunol.* 6:45-51, Current Biology, Ltd. (Feb. 1994).
Rudinger, J., "Characteristics of the amino acids as components of a peptide hormone sequence," in *Peptide Hormones, Parsons*, J.A., ed., University Park Press, Baltimore, MD, pp. 1-7 (1976).
Ruppert, J., et al., "Prominent Role of Secondary Anchor Residues in Peptide Binding to HLA-A2.1 Molecules," *Cell* 74:929-937, Cell Press (Sep. 1993).
Schulz, M., et al., "Major histocompatibility complex binding and T cell recognition of a viral nonapeptide containing a minimal tetrapeptide," *Eur. J. Immunol.* 21:1181-1185, VCH Verlagsgesellschaft mbH (1991).
Sette, A., et al., "Prediction of major histocompatibility complex binding regions of protein antigens by sequence pattern analysis," *Proc. Natl. Acad. Sci. USA* 86:3296-3300, National Academy Press (1989).
Sette, A., at al., "Random association between the peptide repertoire of A2.1 class I and several different DR class II molecules," *J. Immunol.* 147:3893-3900, The American Association of Immunologists (1991).
Sette, A., at al., "The Relationship Between Class I Binding Affinity and Immunogenicity of Potential Cytotoxic T Cell Epitopes," *J. Immunol.* 153:5586-5592, The American Association of Immunologists (Dec. 1994).
Shastri, N., at al., "Presentation of Endogenous Peptide/MHC Class I Complexes is Profoundly Influenced by Specific C-Terminal Flanking Residues," *J. Immunol.* 155: 4339-4346, The American Association of Immunologists (Nov. 1995).
Sherman, L.A., et al., "Extracellular Processing of Peptide Antigens That Bind Class I Major Histocompatibility Molecules," *J. Exp. Med.* 175:1221-1226, The Rockefeller University Press (May 1992).
Shimojo, N., et al., "Specificity of peptide binding by the HLA-A2.1 molecule," *J. Immunol.* 143:2939-2947, The American Association of Immunologists (1989).

Sidney, J., et al., "Several HLA Alleles Share Overlapping Peptide Specificities," *J. Immunol.* 154:247-259, The American Association of Immunologists (Jan. 1995).
Threlkeld, S.C., at al., "Degenerate and Promiscuous Recognition by CTL of Peptides Presented by the MHC Class I A3-like Superfamily. Implications for Vaccine Development," *J. Immunol.* 159:1648-1657, The American Association of Immunologists (Aug. 1997).
Wentworth, P.A., at al., "Differences and similarities in the A2.1-restricted cytotoxic T cell repertoire in humans and human leukocyte antigen-transgenic mice," *Eur. J. Immunol.* 26:97-101, VCH Verlagsgesellschaft mbH (Jan. 1996).
Whitton, J.L., et al., "Molecular Analyses of a Five-Amino-Acid Cytotoxic T- Lymphocyte (CTL) Epitope: an Immunodominant Region Which Induces Nonreciprocal CTL Cross-Reactivity," *J. Virol.* 63:4303-4310, American Society for Microbiology (1989).
Yewdell, J.W., and Bennink, J.R., "Cell Biology of Antigen Processing and Presentation to Major Histocompatibility Complex Class I Molecule-Restricted T Lymphocytes," *Adv. Immunol.* 52:1-123, Academic Press (Jul. 1992).
York, I.A., and Rock, K.L., "Antigen processing and presentation by the class I major histocompatibility complex," *Annu. Rev. Immunol.* 14:369-396, Annual Reviews, Inc. (Apr. 1996).
Zhang, Q-J., et al., "An HLA-A11-specific motif in nonamer peptides derived from viral and cellular proteins," *Proc. Nacl. Acad. Sci. USA* 90:2217-2221, National Academy Press (Mar. 1993).
Kawashima, I. et al., "The Multi-epitope Approach for Immunotherapy for Cancer: Identification of Several CTL Epitopes from Various Tumor-Associated Antigens Expressed on Solid Epithelial Tumors," *Human Immunology*, 59:1-14, Elsevier Science Inc.(1998).
Communication pursuant to Article 94(3) EPC for European Application No. 09 172 693.5, European Patent Office, The Netherlands, mailed Apr. 6, 2011, 7 pages.
Dialog File 351, Accession No. 9888606, Derwent WPI English language abstract for WO 94/11738. Jan. 7, 2003.
Parker, K.C., et al., "Scheme for Ranking Potential HLA-A2 Binding Peptides Based on Independent Binding of Individual Peptide Side-Chains," *J. Immunol.* 152:163-175, The American Association of Immunologists (Jan. 1994).
Dialog File 351, Accession No. 7180926, Derwent WPI English language abstract for EP 02 26 513. Jan. 7, 2003.
Dialog File 351, Accession No. 9263567, Derwent WPI English language abstract for Wo 92/21033. Jan. 7, 2003.
Snoke, K., et al., "The Inhibition of Different T Cell Linea Specific for the Same Antigen with TCR Antagonist Peptides," *J. Immunol.* 151:6815-6821, The American Association of Immunologists (1993).
Tangri, S., et al., "Structural Features of Peptide Analogs of Human Histocompatibility Luekocyte Antigen Class I Epitopes that Are More Potent and Immunogenic than Wild-Type Peptide," *J. Exp. Med.* 194;833-846, The Rockefeller University Press (Sep. 2001).
Co-pending U.S. Appl. No. 08/205,713, inventor Grey, filed Mar. 4, 1994 (Not published).
Co-pending U.S. Appl. No. 08/347,610, inventors Kubo et al., filed Dec. 1, 1994 (Not published).
Co-pending U.S. Appl. No. 09/017,524, inventors Kubo et al., filed Feb. 3, 1998 (Not published).

* cited by examiner

Figure 1C, D
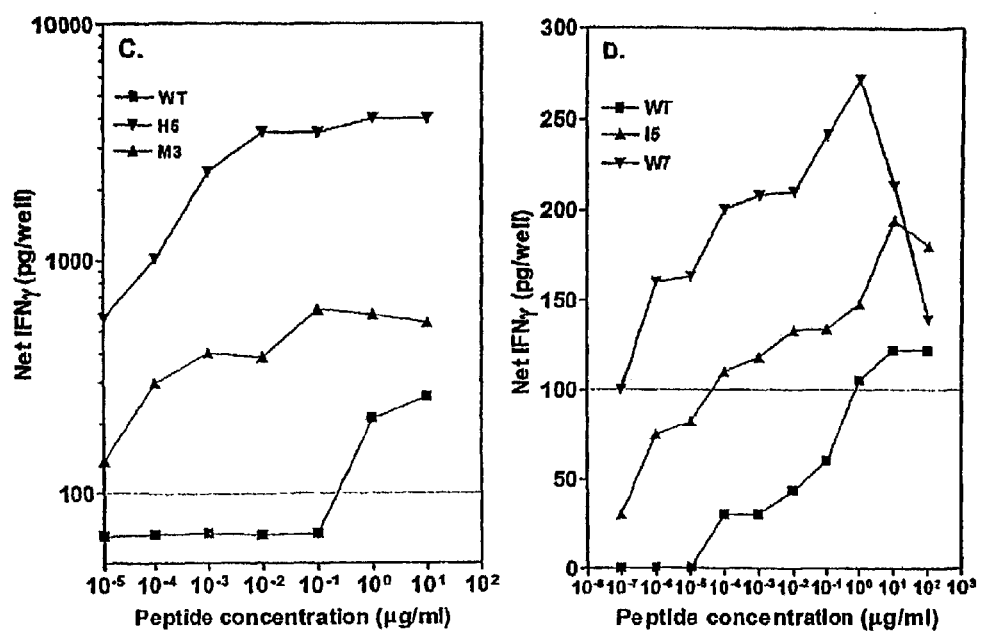

Figure 2B: Antigenicity of HBV Pol455 (suboptimal dose)

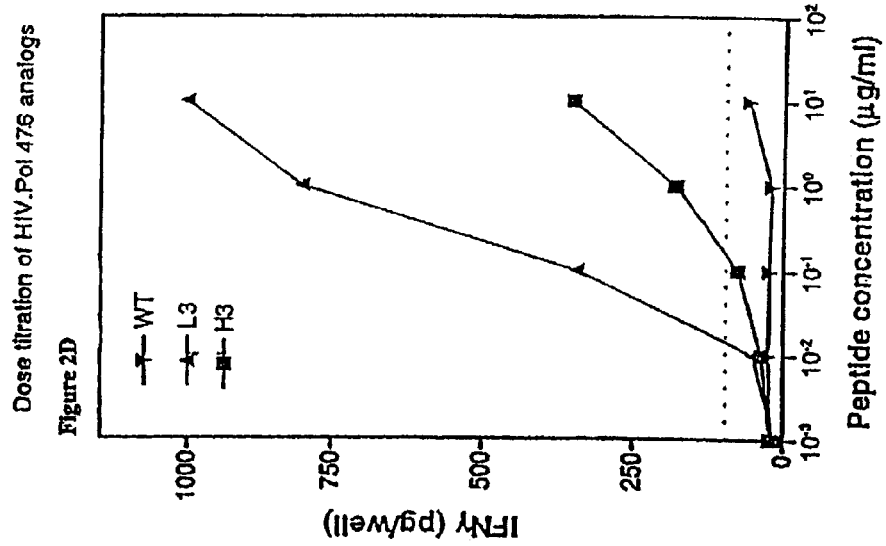

Figure 3A
Figure 3B
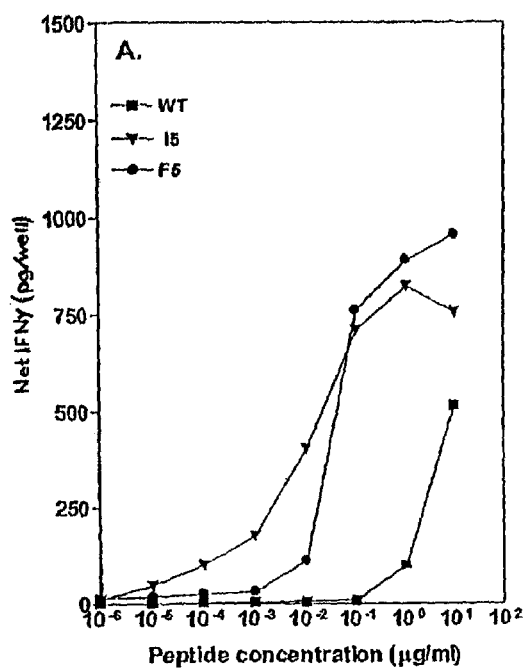
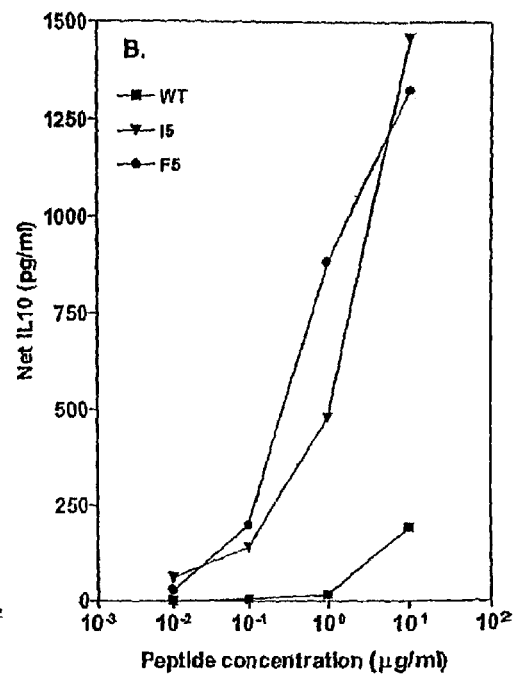
MAGE 2.157 ANALOGS

HIV Pol. 476

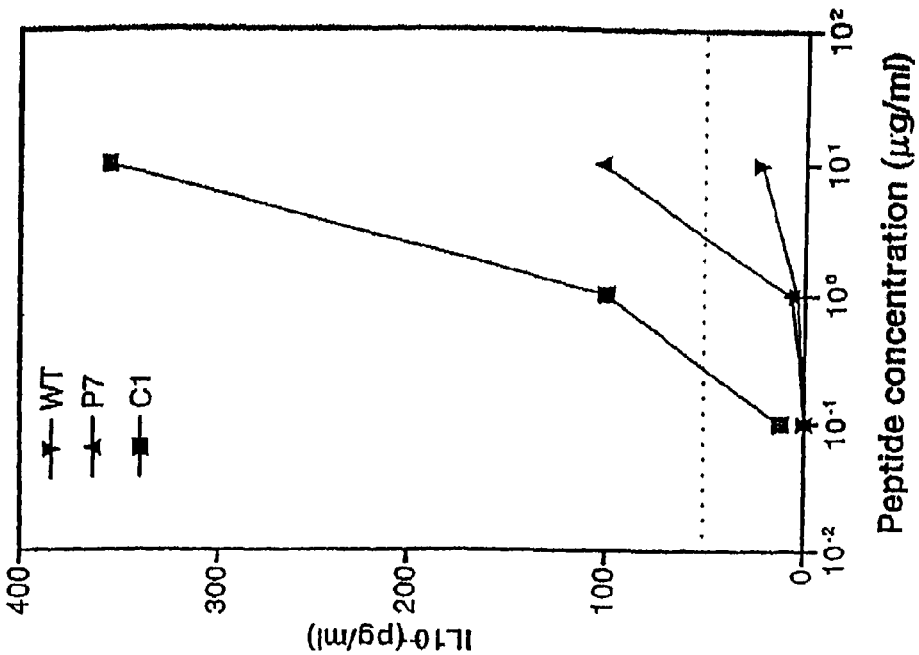
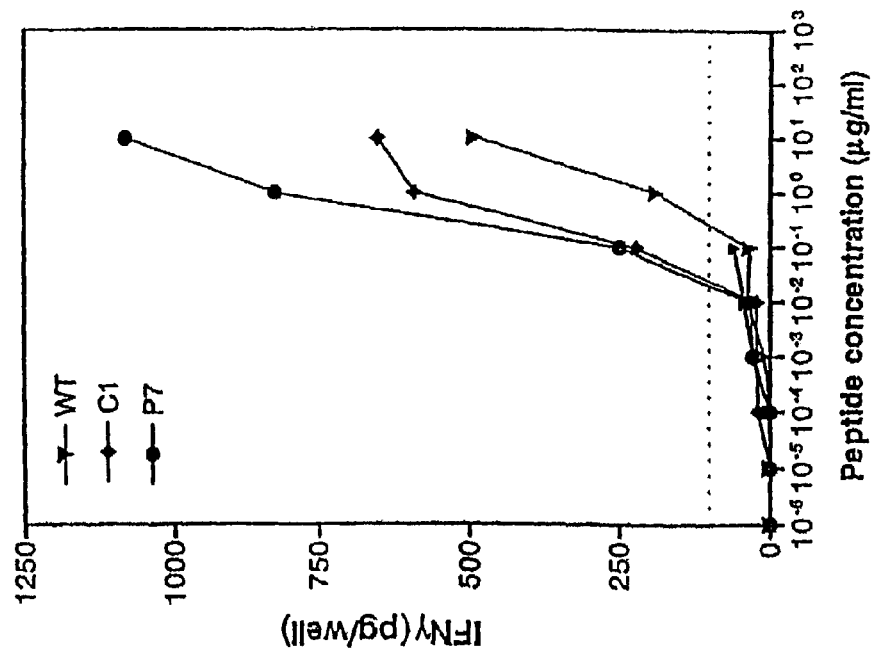

SEQUENCE LISTING

<160> NUMBER OF SEQ ID NOS: 53

<210> SEQ ID NO 1
<211> LENGTH: 9
<212> TYPE: PRT
<213> ORGANISM: Artificial Sequence
<220> FEATURE:
<223> OTHER INFORMATION: CEA.691

<400> SEQUENCE: 1

```
Ile Met Ile Gly Val Leu Val Gly Val
 1               5
```

<210> SEQ ID NO 2
<211> LENGTH: 9
<212> TYPE: PRT
<213> ORGANISM: Artificial Sequence
<220> FEATURE:
<223> OTHER INFORMATION: CEA.691 M3

<400> SEQUENCE: 2

```
Ile Met Met Gly Val Leu Val Gly Val
 1               5
```

<210> SEQ ID NO 3
<211> LENGTH: 9
<212> TYPE: PRT
<213> ORGANISM: Artificial Sequence
<220> FEATURE:
<223> OTHER INFORMATION: CEA.691 H5

```
<400> SEQUENCE: 3

Ile Met Ile Gly His Leu Val Gly Val
1               5

<210> SEQ ID NO 4
<211> LENGTH: 9
<212> TYPE: PRT
<213> ORGANISM: Artificial Sequence
<220> FEATURE:
<223> OTHER INFORMATION: MAGE3.112

<400> SEQUENCE: 4

Lys Val Ala Glu Leu Val His Phe Leu
1               5

<210> SEQ ID NO 5
<211> LENGTH: 9
<212> TYPE: PRT
<213> ORGANISM: Artificial Sequence
<220> FEATURE:
<223> OTHER INFORMATION: MAGE3.112 I5

<400> SEQUENCE: 5

Lys Val Ala Glu Ile Val His Phe Leu
1               5

<210> SEQ ID NO 6
<211> LENGTH: 9
<212> TYPE: PRT
<213> ORGANISM: Artificial Sequence
<220> FEATURE:
<223> OTHER INFORMATION: MAGE3.112 W7

<400> SEQUENCE: 6

Lys Val Ala Glu Leu Val Trp Phe Leu
1               5

<210> SEQ ID NO 7
<211> LENGTH: 10
<212> TYPE: PRT
<213> ORGANISM: Artificial Sequence
<220> FEATURE:
<223> OTHER INFORMATION: MAGE2.157

<400> SEQUENCE: 7

Tyr Leu Gln Leu Val Phe Gly Ile Glu Val
1               5                   10

<210> SEQ ID NO 8
<211> LENGTH: 10
<212> TYPE: PRT
<213> ORGANISM: Artificial Sequence
<220> FEATURE:
<223> OTHER INFORMATION: MAGE2.157 I5

<400> SEQUENCE: 8

Tyr Leu Gln Leu Ile Phe Gly Ile Glu Val
1               5                   10

<210> SEQ ID NO 9
<211> LENGTH: 10
<212> TYPE: PRT
<213> ORGANISM: Artificial Sequence
<220> FEATURE:
<223> OTHER INFORMATION: MAGE2.157 F5

<400> SEQUENCE: 9
```

-continued

Tyr Leu Gln Leu Phe Phe Gly Ile Glu Val
 1               5                   10

<210> SEQ ID NO 10
<211> LENGTH: 9
<212> TYPE: PRT
<213> ORGANISM: Artificial Sequence
<220> FEATURE:
<223> OTHER INFORMATION: p53.149M2

<400> SEQUENCE: 10

Ser Met Pro Pro Pro Gly Thr Arg Val
 1               5

<210> SEQ ID NO 11
<211> LENGTH: 9
<212> TYPE: PRT
<213> ORGANISM: Artificial Sequence
<220> FEATURE:
<223> OTHER INFORMATION: p53.149M2 C1

<400> SEQUENCE: 11

Cys Met Pro Pro Pro Gly Thr Arg Val
 1               5

<210> SEQ ID NO 12
<211> LENGTH: 9
<212> TYPE: PRT
<213> ORGANISM: Artificial Sequence
<220> FEATURE:
<223> OTHER INFORMATION: p53.149M2 P7

<400> SEQUENCE: 12

Ser Met Pro Pro Pro Gly Pro Arg Val
 1               5

<210> SEQ ID NO 13
<211> LENGTH: 11
<212> TYPE: PRT
<213> ORGANISM: Artificial Sequence
<220> FEATURE:
<223> OTHER INFORMATION: p53.Mu184

<400> SEQUENCE: 13

Gly Leu Ala Pro Pro Gln His Leu Ile Arg Val
 1               5                   10

<210> SEQ ID NO 14
<211> LENGTH: 11
<212> TYPE: PRT
<213> ORGANISM: Artificial Sequence
<220> FEATURE:
<223> OTHER INFORMATION: p53.Mu184 T3

<400> SEQUENCE: 14

Gly Leu Thr Pro Pro Gln His Leu Ile Arg Val
 1               5                   10

<210> SEQ ID NO 15
<211> LENGTH: 11
<212> TYPE: PRT
<213> ORGANISM: Artificial Sequence
<220> FEATURE:
<223> OTHER INFORMATION: p53.Mu184 T3, E6

<400> SEQUENCE: 15

Gly Leu Thr Pro Pro Glu His Leu Ile Arg Val

```
<210> SEQ ID NO 16
<211> LENGTH: 9
<212> TYPE: PRT
<213> ORGANISM: Artificial Sequence
<220> FEATURE:
<223> OTHER INFORMATION: HBV Pol455

<400> SEQUENCE: 16

Gly Leu Ser Arg Tyr Val Ala Arg Leu
1               5

<210> SEQ ID NO 17
<211> LENGTH: 9
<212> TYPE: PRT
<213> ORGANISM: Artificial Sequence
<220> FEATURE:
<223> OTHER INFORMATION: HBV Pol455 P7

<400> SEQUENCE: 17

Gly Leu Ser Arg Tyr Val Pro Arg Leu
1               5

<210> SEQ ID NO 18
<211> LENGTH: 9
<212> TYPE: PRT
<213> ORGANISM: Artificial Sequence
<220> FEATURE:
<223> OTHER INFORMATION: HIV Pol476

<400> SEQUENCE: 18

Ile Leu Lys Glu Pro Val His Gly Val
1               5

<210> SEQ ID NO 19
<211> LENGTH: 9
<212> TYPE: PRT
<213> ORGANISM: Artificial Sequence
<220> FEATURE:
<223> OTHER INFORMATION: HIV Pol476 H3

<400> SEQUENCE: 19

Ile Leu His Glu Pro Val His Gly Val
1               5

<210> SEQ ID NO 20
<211> LENGTH: 9
<212> TYPE: PRT
<213> ORGANISM: Artificial Sequence
<220> FEATURE:
<223> OTHER INFORMATION: HIV Pol476L3

<400> SEQUENCE: 20

Ile Leu Ile Glu Pro Val His Gly Val
1               5

<210> SEQ ID NO 21
<211> LENGTH: 9
<212> TYPE: PRT
<213> ORGANISM: Artificial Sequence
<220> FEATURE:
<223> OTHER INFORMATION: p53.261

<400> SEQUENCE: 21

Leu Leu Gly Arg Asp Ser Phe Glu Val
1               5
```

```
<210> SEQ ID NO 22
<211> LENGTH: 9
<212> TYPE: PRT
<213> ORGANISM: Artificial Sequence
<220> FEATURE:
<223> OTHER INFORMATION: p53.261 D3

<400> SEQUENCE: 22

Leu Leu Asp Arg Asp Ser Phe Glu Val
 1               5

<210> SEQ ID NO 23
<211> LENGTH: 9
<212> TYPE: PRT
<213> ORGANISM: Artificial Sequence
<220> FEATURE:
<223> OTHER INFORMATION: p53.261 H3

<400> SEQUENCE: 23

Leu Leu His Arg Asp Ser Phe Glu Val
 1               5

<210> SEQ ID NO 24
<211> LENGTH: 9
<212> TYPE: PRT
<213> ORGANISM: Artificial Sequence
<220> FEATURE:
<223> OTHER INFORMATION: p53.261 L7

<400> SEQUENCE: 24

Leu Leu Gly Arg Asp Ser Leu Glu Val
 1               5

<210> SEQ ID NO 25
<211> LENGTH: 9
<212> TYPE: PRT
<213> ORGANISM: Artificial Sequence
<220> FEATURE:
<223> OTHER INFORMATION: p53.261 H7

<400> SEQUENCE: 25

Leu Leu Gly Arg Asp Ser His Glu Val
 1               5

<210> SEQ ID NO 26
<211> LENGTH: 9
<212> TYPE: PRT
<213> ORGANISM: Artificial Sequence
<220> FEATURE:
<223> OTHER INFORMATION: p53.261 N5

<400> SEQUENCE: 26

Leu Leu Gly Arg Asn Ser Phe Glu Val
 1               5

<210> SEQ ID NO 27
<211> LENGTH: 9
<212> TYPE: PRT
<213> ORGANISM: Artificial Sequence
<220> FEATURE:
<223> OTHER INFORMATION: p53.261 G5

<400> SEQUENCE: 27

Leu Leu Gly Arg Gly Ser Phe Glu Val
 1               5

<210> SEQ ID NO 28
```

```
<211> LENGTH: 9
<212> TYPE: PRT
<213> ORGANISM: Artificial Sequence
<220> FEATURE:
<223> OTHER INFORMATION: None

<400> SEQUENCE: 28

Ala Pro Ala Ala Ala Ala Ala Ala Tyr
1               5

<210> SEQ ID NO 29
<211> LENGTH: 10
<212> TYPE: PRT
<213> ORGANISM: Artificial sequence
<220> FEATURE:
<223> OTHER INFORMATION: None

<400> SEQUENCE: 29

Lys Val Phe Pro Tyr Ala Leu Ile Asn Lys
1               5                   10

<210> SEQ ID NO 30
<211> LENGTH: 13
<212> TYPE: PRT
<213> ORGANISM: Artificial Sequence
<220> FEATURE:
<223> OTHER INFORMATION: (HBV core)

<400> SEQUENCE: 30

Thr Pro Pro Ala Tyr Arg Pro Pro Asn Ala Pro Ile Leu
1               5                   10

<210> SEQ ID NO 31
<211> LENGTH: 10
<212> TYPE: PRT
<213> ORGANISM: Artificial Sequence
<220> FEATURE:
<223> OTHER INFORMATION: (HBI Core)

<400> SEQUENCE: 31

Phe Leu Pro Ser Asp Phe Phe Asp Ser Val
1               5                   10

<210> SEQ ID NO 32
<211> LENGTH: 14
<212> TYPE: PRT
<213> ORGANISM: Tetanus toxoid

<400> SEQUENCE: 32

Gln Tyr Ile Lys Ala Asn Ser Lys Phe Ile Gly Ile Thr Glu
1               5                   10

<210> SEQ ID NO 33
<211> LENGTH: 21
<212> TYPE: PRT
<213> ORGANISM: Plasmodium falciparum

<400> SEQUENCE: 33

Asp Ile Glu Lys Lys Ile Ala Lys Met Glu Lys Ala Ser Ser Val Phe
1               5                   10                  15

Asn Val Val Asn Ser
                20

<210> SEQ ID NO 34
<211> LENGTH: 16
<212> TYPE: PRT
<213> ORGANISM: Streptococcus 18 kD
```

```
<400> SEQUENCE: 34

Gly Ala Val Asp Ser Ile Leu Gly Gly Val Ala Thr Tyr Gly Ala Ala
1               5                   10                  15

<210> SEQ ID NO 35
<211> LENGTH: 13
<212> TYPE: PRT
<213> ORGANISM: Artificial Sequence
<220> FEATURE:
<223> OTHER INFORMATION: pan-DR-binding epitope peptide
<220> FEATURE:
<221> NAME/KEY: MISC_FEATURE
<222> LOCATION: (1)..(1)
<223> OTHER INFORMATION: Xaa may be D- or L-Alanine
<220> FEATURE:
<221> NAME/KEY: MISC_FEATURE
<222> LOCATION: (3)..(3)
<223> OTHER INFORMATION: Xaa represents cyclohexylalanine
<220> FEATURE:
<221> NAME/KEY: MISC_FEATURE
<222> LOCATION: (13)..(13)
<223> OTHER INFORMATION: Xaa may be D- or L-Alanine

<400> SEQUENCE: 35

Xaa Lys Xaa Val Ala Ala Trp Thr Leu Lys Ala Ala Xaa
1               5                   10

<210> SEQ ID NO 36
<211> LENGTH: 13
<212> TYPE: PRT
<213> ORGANISM: Artificial Sequence
<220> FEATURE:
<223> OTHER INFORMATION: pan-DR-binding epitope peptide
<220> FEATURE:
<221> NAME/KEY: MISC_FEATURE
<222> LOCATION: (1)..(1)
<223> OTHER INFORMATION: Xaa may be D- or L-Alanine
<220> FEATURE:
<221> NAME/KEY: MISC_FEATURE
<222> LOCATION: (13)..(13)
<223> OTHER INFORMATION: Xaa may be D- or L-Alanine

<400> SEQUENCE: 36

Xaa Lys Phe Val Ala Ala Trp Thr Leu Lys Ala Ala Xaa
1               5                   10

<210> SEQ ID NO 37
<211> LENGTH: 13
<212> TYPE: PRT
<213> ORGANISM: Artificial Sequence
<220> FEATURE:
<223> OTHER INFORMATION: pan-DR-binding epitope peptide
<220> FEATURE:
<221> NAME/KEY: MISC_FEATURE
<222> LOCATION: (1)..(1)
<223> OTHER INFORMATION: Xaa may be D- or L-Alanine
<220> FEATURE:
<221> NAME/KEY: MISC_FEATURE
<222> LOCATION: (13)..(13)
<223> OTHER INFORMATION: Xaa may be D- or L-Alanine

<400> SEQUENCE: 37

Xaa Lys Tyr Val Ala Ala Trp Thr Leu Lys Ala Ala Xaa
1               5                   10

<210> SEQ ID NO 38
<211> LENGTH: 10
<212> TYPE: PRT
<213> ORGANISM: Artificial Sequence
<220> FEATURE:
<223> OTHER INFORMATION: HBV Core.18 epitope
```

```
<400> SEQUENCE: 38

Phe Leu Pro Ser Asp Phe Phe Pro Ser Val
1               5                   10

<210> SEQ ID NO 39
<211> LENGTH: 9
<212> TYPE: PRT
<213> ORGANISM: Artificial Sequence
<220> FEATURE:
<223> OTHER INFORMATION: HLA-B7 supermotif bearing peptide

<400> SEQUENCE: 39

Ala Pro Arg Thr Leu Val Tyr Leu Leu
1               5

<210> SEQ ID NO 40
<211> LENGTH: 9
<212> TYPE: PRT
<213> ORGANISM: Artificial Sequence
<220> FEATURE:
<223> OTHER INFORMATION: HLA-B7 supermotif bearing peptide

<400> SEQUENCE: 40

Ala Pro Glu Thr Leu Val Tyr Leu Leu
1               5

<210> SEQ ID NO 41
<211> LENGTH: 9
<212> TYPE: PRT
<213> ORGANISM: Artificial Sequence
<220> FEATURE:
<223> OTHER INFORMATION: HLA-B7 supermotif bearing peptide

<400> SEQUENCE: 41

Ala Pro Arg Thr Trp Val Tyr Leu Leu
1               5

<210> SEQ ID NO 42
<211> LENGTH: 9
<212> TYPE: PRT
<213> ORGANISM: Artificial Sequence
<220> FEATURE:
<223> OTHER INFORMATION: HLA-B7 supermotif bearing peptide

<400> SEQUENCE: 42

Ala Pro Arg Thr Leu Val Pro Leu Leu
1               5

<210> SEQ ID NO 43
<211> LENGTH: 10
<212> TYPE: PRT
<213> ORGANISM: Artificial Sequence
<220> FEATURE:
<223> OTHER INFORMATION: HLA-A3 supermotif bearing peptide

<400> SEQUENCE: 43

Lys Val His Pro Tyr Ala Leu Ile Asn Lys
1               5                   10

<210> SEQ ID NO 44
<211> LENGTH: 10
<212> TYPE: PRT
<213> ORGANISM: Artificial Sequence
<220> FEATURE:
<223> OTHER INFORMATION: HLA-A3 supermotif bearing peptide

<400> SEQUENCE: 44
```

```
Lys Val Phe Pro Gln Ala Leu Ile Asn Lys
  1               5                   10

<210> SEQ ID NO 45
<211> LENGTH: 10
<212> TYPE: PRT
<213> ORGANISM: Artificial sequence
<220> FEATURE:
<223> OTHER INFORMATION: HLA-A3 supermotif bearing peptide

<400> SEQUENCE: 45

Lys Val Phe Pro Tyr Ala Lys Ile Asn Lys
  1               5                   10

<210> SEQ ID NO 46
<211> LENGTH: 9
<212> TYPE: PRT
<213> ORGANISM: Artificial sequence
<220> FEATURE:
<223> OTHER INFORMATION: MAGE3.122

<400> SEQUENCE: 46

Lys Val Ala Glu Leu Val His Phe Leu
  1               5

<210> SEQ ID NO 47
<211> LENGTH: 9
<212> TYPE: PRT
<213> ORGANISM: Artificial Sequence
<220> FEATURE:
<223> OTHER INFORMATION: HIV Pol.476

<400> SEQUENCE: 47

Ile Leu Lys Glu Pro Val His Gly Phe
  1               5

<210> SEQ ID NO 48
<211> LENGTH: 9
<212> TYPE: PRT
<213> ORGANISM: Artificial Sequence
<220> FEATURE:
<223> OTHER INFORMATION: MAGE2.170

<400> SEQUENCE: 48

Val Pro Ile Ser His Leu Tyr Ile Leu
  1               5

<210> SEQ ID NO 49
<211> LENGTH: 9
<212> TYPE: PRT
<213> ORGANISM: Artificial Sequence
<220> FEATURE:
<223> OTHER INFORMATION: MAGE2.170 H7

<400> SEQUENCE: 49

Val Pro Ile Ser His Leu His Ile Leu
  1               5

<210> SEQ ID NO 50
<211> LENGTH: 9
<212> TYPE: PRT
<213> ORGANISM: Artificial Sequence
<220> FEATURE:
<223> OTHER INFORMATION: MAGE2.170 M7

<400> SEQUENCE: 50

Val Pro Ile Ser His Leu Met Ile Leu
```

-continued

```
<210> SEQ ID NO 51
<211> LENGTH: 9
<212> TYPE: PRT
<213> ORGANISM: Artificial Sequence
<220> FEATURE:
<223> OTHER INFORMATION: MAGE2.170 G7

<400> SEQUENCE: 51

Val Pro Ile Ser His Leu Gly Ile Leu
1               5

<210> SEQ ID NO 52
<211> LENGTH: 9
<212> TYPE: PRT
<213> ORGANISM: Artificial Sequence
<220> FEATURE:
<223> OTHER INFORMATION: MAGE2.170 E7

<400> SEQUENCE: 52

Val Pro Ile Ser His Leu Glu Ile Leu
1               5

<210> SEQ ID NO 53
<211> LENGTH: 9
<212> TYPE: PRT
<213> ORGANISM: Artificial Sequence
<220> FEATURE:
<223> OTHER INFORMATION: MAGE2.170 D7

<400> SEQUENCE: 53

Val Pro Ile Ser His Leu Asp Ile Leu
1               5
```

HETEROCLITIC ANALOGS AND RELATED METHODS

CROSS-REFERENCE TO RELATED APPLICATIONS

The present application is a continuation-in-part of International Application No. PCT/US00/31856, filed Nov. 20, 2000, which published under PCT article 21(2) in English, and which claims the benefit of U.S. Provisional Patent Application No. 60/166,529, filed Nov. 18, 1999, and U.S. Provisional Patent Application No. 60/239,008, filed Oct. 6, 2000; each of said applications is incorporated by reference in its entirety.

BACKGROUND OF THE INVENTION

Field of the Invention

The invention relates to methods for generating heteroclitic analogs of an original peptide which have increased stimulatory capacity for a given T cell.

Several studies suggest the cytotoxic T lymphocytes (CTLs) play a central role in the eradication of infectious disease and cancer by the immune system (Byrne, et al., *J. Immunol.* 51:682 (1984), McMichael, et al., *N. England J. Med.*, 309:13 (1983)). Since CTLs are stimulated by peptides comprising epitopes, considerable effort is ongoing in developing epitope-based vaccines that stimulate CTL responses. One class of epitopes, designated heteroclitic analogs, provides benefit as vaccine components since these analogs induce T cell responses stronger than those induced by the native epitope. Heteroclitic analogs are defined as peptides having increased stimulatory capacity or potency for a specific T cell, as measured by increased responses to a given dose, or by a requirement of lesser amounts to achieve the same response.

The advantages associated with using heteroclitic analogs in clinical applications are as follows. First, heteroclitic analogs have the ability to break/overcome tolerance by reversing a state of T cell anergy, activating non-tolerized cross-reactive clones of T cells, or by mediating "immune deviation," i.e., the type of CTL produced, such as Th1 or Th2. Recent studies indicate that heteroclitic analogs are immunogenic (Zaremba, et al., *Cancer Research*, 57:4570 (1997); Rivoltoni, et al., *Cancer Research*, 59:301 (1999); Selby, et al., 162(2):669 (1999)) in that they are capable of inducing CTLs that recognize endogenously processed epitope. This is confirmed by studies in different immunological systems (Zugel, et al., *J. Immunol.*, 161:1705 (1998), Wang, et al., *J. Exp. Med.*, 190:983 (1999), Men, et al., *J. Immunol.*, 162:3566, (1999)). For example, studies by Zugel et al. (Zugel, et al., supra) have shown that T cell tolerance to an immunodominant T cell epitope in adult mice can be overcome by immunization with heteroclitic cross-reactive peptide analogs of that peptide.

This is particularly significant in the field of cancer vaccines, where most of the CTL epitopes are derived from self antigens. Due to the fact that cancer related antigens are often self-antigens there is a corresponding phenomenon that there may be preexisting tolerance to these antigens, whereby generation of a T cell response to such epitopes is a challenge. Breaking of tolerance by heteroclitic analogs has been shown in a recent study in a murine Class II system (Wang, et al., *J. Exp. Med.* 190:983 (1999)). In this study, the mechanism involved in breaking of tolerance was the stimulation of non-tolerized, low affinity clones, rather than reversal of anergy. The heteroclicity demonstrated herein is associated with the induction of high avidity CTL, this represents an important difference.

Second, peptide analogs have been demonstrated to modulate cytokine production from T cells (Pfeiffer, et al., *J. Exp. Med.*, 181:1569 (1995), Tao, et al., *J. Immunol.*, 158:4237 (1997), Salazar, et al., *Int. J. Cancer* 85(6):829-38 (2000), Nicholson, et al., *Int. Immunol.* 12(2):205-13 (2000)). The immune deviation induced by such analogs has implications in several disease states, where generation of a specific subset of Th cell responses correlate with tumor regression (Zitvogel, et al., *J. Exp. Med.*, 183:87 (1996), Celluzzi, et al., *J. Exp. Med.* 183:283 (1996)) or affected the clinical outcome of autoimmune or infectious disease (Romagnani, et al., *Annu. Rev. Immunol.*, 12:227-57 (1994)). Thus, immunization with heteroclitic analogs offers the capacity to modulate cytokine production by induction of specific subsets of effector T cells, thereby altering the course of disease.

Third, heteroclitic analogs offer an advantage in drug development since significantly smaller amounts of peptide are needed for treatment doses, due to their strong biological potency. This feature overcomes certain manufacturing and toxicity concerns. In this regard, it has been shown that a heteroclitic analog of a MART-1 peptide (Rivoltini, et al., *Cancer Research* 59:301 (1999)), which generated antigen specific T cells in melanoma patients, was active at much lower concentrations than the native epitope. Similar results were reported by Schlom and colleagues (Zaremba, et al., *Cancer Research* 57:4570 (1997)) regarding heteroclitic analog of the CEA derived CAP1 epitope. However, a side-by-side precursor frequency analysis or a TCR avidity analysis against wildtype peptide was not performed.

Accordingly, because of their biological relevance, it would be extremely useful to predict amino acid substitutions that render heteroclitic activity to a given epitope. However, prior to the present disclosure there has been no easy method for predicting such substitutions. Indeed, in previous studies (Selby, et al., *J. Immunol.*, 162(2):669 (1999), Skipper, et al., *J. Exp. Med.* 183:527 (1996)), heteroclitic epitopes were fortuitously identified by eluting naturally occurring mutant peptides from melanoma cells, or by systematically screening a large number of analogs consisting of substitutions at almost every position in the epitope (Zaremba, et al., *Cancer Research*, 57:4570 (1997), Loftus, et al., *Cancer Research* 58:2433 (1998), Blake, et al., *J. Exp. Med.* 18:121 (1996)). Alternatively, heteroclitic analogs were identified by screening random combinatorial peptide libraries which also has required the arduous synthesis and screening of large numbers of peptides (Pinilla, et al., *Current Opinion in Immunology* 11:193-202 (1999)). Genetic approaches, such as screening of DNA expression libraries, have provided another method for generating CTL epitopes and analogs (Boon, et al., *Annu. Rev. Immunol.* 12:337-65 (1994), Gavin, et al., *Eur. J. Immunol.* 24(9):2124-33 (1994)). However, this approach may be problematic given the potentially small quantities and complexity of epitopes generated.

BRIEF SUMMARY OF THE INVENTION

The invention provides methods to prepare peptides containing epitopes which have enhanced ability to effect an immune response with respect to corresponding analogous wildtype epitopes. The resulting "heteroclitic analogs" are useful in immunological compositions for treatment of viral diseases, cancer, and other conditions which are characterized by displayed antigens on target cells.

Thus, in one aspect, the invention is directed to a method to enhance the immunogenicity of a peptide containing an epitope, the method comprising i) providing a peptide comprising a first Class I epitope wherein said epitope consists essentially of an amino acid sequence having an N-terminus and a C-terminus and at least one primary anchor residue, wherein amino acid residues of the epitope are numbered consecutively and the primary anchor residue nearest the N-terminus of the epitope is at position 2 or position 3; and ii) introducing one or more conservative or semi-conservative substitution between the N-terminus and the C-terminus of the epitope at position 3 and/or 5 and/or 7 which position does not contain a primary anchor residue, thereby constructing a peptide comprising a second Class I epitope which exhibits enhanced immunogenicity compared to the first Class I epitope.

In another aspect, in the case of B7 superfamily epitopes, the invention is directed to a method to enhance the immunogenicity of a peptide containing a B7 superfamily epitope, the method comprising i) providing a peptide comprising a first Class I epitope which is a B7 superfamily epitope wherein said epitope consists essentially of an amino acid sequence having an N-terminus and a C-terminus and at least one primary anchor residue, wherein amino acid residues of the epitope are numbered consecutively and the primary anchor residue nearest the N-terminus of the epitope is at position 2; and ii) introducing one or more conservative, semi-conservative, or non-conservative substitution between the N-terminus and the C-terminus of the epitope at position 3 and/or 5 and/or 7, thereby constructing a peptide comprising a second Class I epitope which is a B7 superfamily epitope which exhibits enhanced immunogenicity compared to the first Class I epitope.

Thus, the invention relates to a method of producing a polypeptide comprising an analog of a MHC class I epitope, wherein the analog has enhanced immunogenicity compared to the epitope, comprising (a) identifying a MHC class I epitope comprising a formula (A), wherein formula (A) is Rn-R2-R3-R4-R5-R6-R7-...Rx, Rn is the N-terminal amino acid, Rx is the C-terminal amino acid, x=8-11 such that Rx can be from the eighth to the eleventh amino acid residue from Rn, R2 or R3 and Rx are primary anchor residues of a motif or a supermotif, and (b) producing a polypeptide comprising an analog, said analog comprising a formula (B) identical to said formula (A) except one or more conservative or semiconservative amino acid substitutions at R3 and/or R5 and/or R7, provided said one or more substitutions is not of a primary anchor residues.

In some aspects, said analog comprises a formula (B) identical to said formula (A) except that R3 is Met, provided R3 is not an anchor residue of said motif or supermotif.

In some aspects, said analog comprises a formula (B) identical to said formula (A) except that R5 is Met.

In some aspects, said analog comprises a formula (B) identical to said formula (A) except that R7 is Met.

In some aspects, R3 is Ile in formula (A), and said analog comprises a formula (B) identical to said formula (A) except that R3 is Met.

In some aspects, R3 is Lys in formula (A), and said analog comprises a formula (B) identical to said formula (A) except that R3 is His or Leu.

In some aspects, R5 is Val in formula (A), and said analog comprises a formula (B) identical to said formula (A) except that R5 is His.

In some aspects, R5 is Leu in formula (A), and said analog comprises a formula (B) identical to said formula (A) except that R5 is Ile.

In some aspects, R5 is Val in formula (A), and said analog comprises a formula (B) identical to said formula (A) except that R5 is Ile or Phe.

In some aspects, R7 is His in formula (A), and said analog comprises a formula (B) identical to said formula (A) except that R7 is Trp.

In some aspects, R7 is Ala in formula (A), and said analog comprises a formula (B) identical to said formula (A) except that R7 is Pro.

In some aspects, R7 is Tyr in formula (A), and said analog comprises a formula (B) identical to said formula (A) except that R7 is His or Met.

In other aspects, the invention relates to a method of producing a polypeptide comprising an analog of a MHC class I epitope, wherein the analog has enhanced immunogenicity compared to the epitope, comprising (a) identifying a MHC class I epitope comprising a formula (A), wherein formula (A) is Rn-R2-R3-R4-R5-R6-R7-...Rx, Rn is the N-terminal amino acid, Rx is the C-terminal amino acid, x=8-11 such that Rx can be from the eighth to the eleventh amino acid residue from Rn, R2 or R3 and Rx are primary anchor residues of a motif or a supermotif, and (b) producing a polypeptide comprising an analog, said analog comprising a formula (B) identical to said formula (A) except one or more nonconservative amino acid substitutions at R3 and/or R5 and/or R7.

Thus, in some aspects, R7 is Tyr in formula (A), and said analog comprises a formula (B) identical to said formula (A) except that R7 is Gly, Glu, or Asp.

The second Class I epitope described above is generically referred to as a "heteroclitic analog" or an "analog."

In a preferred embodiment, the heteroclitic analog exhibits at least about 50% increased potency for a specific T-cell compared to the corresponding wildtype Class I epitope. The analog may contain only one substitution, or may contain two or three, and the substitution may be conservative or semi-conservative or, in the case of a B7 superfamily epitope, non-conservative. The heteroclitic analog may induce both Th1 and Th2 cytokines when bound by an HLA Class I molecule and contacted with the relevant cytotoxic T-cell. Preferably, the Class I epitope comprises an HLA supermotif selected from the group consisting of A1, A2, A3, A24, B7, B27, B44, B58 and B62, more preferably, the Class I epitope comprises an A2 supermotif or a B7 supermotif, most preferably, an A2.1 motif (e.g. an A*0201), or a B7 motif (e.g. a B*0702 motif).

The class I epitope may be from a viral antigen, a tumor-associated antigen, a parasitic antigen, a bacterial antigen or a fungal antigen.

The supermotif may be A1, wherein R2 is a primary anchor residue and is either T, I, L, V, M or S, and Rx is either F, W, or Y.

The supermotif may be A2, wherein R2 is a primary anchor residue and is either L, I, V, M, A, T, or Q, and Rx is I, V, M, A, T, or L.

The supermotif may be A2.1, wherein R2 is a primary anchor and is either L, M, V, Q, I, A, or T, and Rx is either V, L, I, M, A, or T.

The supermotif may be A3, wherein R2 is a primary anchor residue and is either V, S, M, A, T, L, or I, and Rx is R or K.

The supermotif may be A24, wherein R2 is a primary anchor residue and is either Y, f, W, I, V, L, M, or T, and Rx is either F, I, Y, W, L, or M.

The supermotif may be B7, wherein R2 is a primary anchor residue and is P and Rx is either V, I, L, F, M, W, Y, or A.

The invention also provides methods of inducing a human cytotoxic T cell response against a preselected Class I peptide epitope, the method comprising providing the heteroclitic analog described above; and contacting a human CTL with the heteroclitic analog.

In some aspects, the step of contacting is carried out in vitro. In some aspects, the step of contacting is carried out by administering to a subject a nucleic acid molecule comprising a sequence encoding the heteroclitic analog peptide epitope.

The invention also provides polypeptides produced by the method described above. The invention is also directed to peptides, e.g., polypeptides, comprising the heteroclitic analog epitopes which are obtainable by the method described above. In particular, and preferably, such peptides include those where the epitope (e.g., analog) consists of an amino acid sequence selected from the group consisting of SEQ ID NO: 2, SEQ ID NO: 3, SEQ ID NO: 5, SEQ ID NO: 6, SEQ ID NO: 8, SEQ ID NO: 9, SEQ ID NO: 11, SEQ ID NO: 12, SEQ ID NO: 14, SEQ ID NO: 15, SEQ ID NO: 17, SEQ ID NO: 19, SEQ ID NO:20, SEQ ID NO:22, SEQ ID NO:23, SEQ ID NO:24, SEQ ID NO:25, SEQ ID NO:26, SEQ ID NO:27, SEQ ID NO:49, SEQ ID NO:50, SEQ ID NO:51, SEQ ID NO:52, and SEQ ID NO:53. The peptide may contain 9-20 amino acids, preferably 9-16, more preferably 9-15, but may also contain only a total of 9, 10, 11, 12, 13 or 14 amino acids. The defined heteroclitic analog epitopes may be included in a longer polypeptide or protein which is a homopolymer of the same epitope (e.g., analog) or a heteropolymer which contains a variety of such epitopes (e.g., analogs) or the heteroclitic analog epitope in combination with wildtype epitopes. These peptides and proteins may be included in compositions which are designed for pharmaceutical use.

The peptides or heteropolymers or homopolymers containing the heteroclitic analog epitopes may be combined with other components to enhance further or modulate their activity in eliciting an immune response. These additional varieties may be covalently bound or non-covalently included in a mixture.

Thus, the polypeptide may comprise a T helper peptide, a spacer or linker amino acid, a carrier, may be linked to a lipid, may comprise a fusion protein, may comprise a homopolymer, a heteropolymer, and/or may comprise one or more second epitopes or second analogs.

Further, the heteroclitic analog epitope may be admixed or joined to a CTL epitope, or to an HTL epitope, especially where HTL epitope is a pan-DR binding molecule. A composition containing the heteroclitic analog epitope may further comprise a liposome, wherein the epitope is on or within the liposome, or the epitope may be joined to a lipid. The heteroclitic epitope may be bound to an HLA heavy chain, β2-microglobulin, and strepavidin complex, whereby a tetramer is formed. In addition, the heteroclitic epitope (e.g., polypeptide comprising an analog) may be modified in a composition which comprises an antigen presenting cell, wherein the epitope (e.g., a polypeptide comprising an analog) is on or within the antigen presenting cell, wherein the epitope (e.g., a polypeptide comprising an analog) is bound to an HLA molecule on the antigen presenting cell. Thus, when a cytotoxic lymphocyte (CTL) that is restricted to the HLA molecule is present, a receptor of the CTL binds to a complex of the HLA molecule and the epitope (e.g., a polypeptide comprising an analog). The antigen presenting cell may be a dendritic cell. The composition may also simply comprise an HLA molecule, wherein the peptide containing the epitope (e.g., a polypeptide comprising an analog) is bound by the HLA molecule. The composition may also comprise a label—e.g., biotin, a fluorescent moiety, a non-mammalian sugar, a radiolabel or a small molecule to which a monoclonal antibody binds.

The compositions described are useful in eliciting an immune response against the corresponding wildtype epitope. Typically, the heteroclitic analog is included in such compositions which will further contain suitable excipients. The active component heteroclitic epitopes (e.g., a polypeptide comprising an analog)s may be present in unit dosage form. Compositions useful in treating subjects may also comprise nucleic acid molecules that encode the peptides described above optionally including control sequences for their expression.

BRIEF DESCRIPTION OF THE DRAWINGS/FIGURES

FIGS. 1A-1D. FIGS. 1A and 1B represent the results of testing a panel of analogs of CEA.691 and MAGE3.112 respectively for ability to induce IFNγ production in the corresponding CTL. FIGS. 1C and 1D are the corresponding dose response curves for CEA.691 and MAGE3.112 heteroclitic analogs respectively.

FIGS. 2A-2D. FIGS. 2A, 2B and 2C show the results of testing panels of analogs of MAGE2.157, HIVPol.476, and HBVPol.455 epitope analogs with respect to the ability of these analogs to induce IFNγ production in the corresponding CTLs. FIG. 2D is the relevant dose response curve for the successful HIVPol.476 analogs.

FIGS. 3A and 3B show dose response curves of heteroclitic analogs of MAGE2.157 in comparison to wildtype with regard to their ability to induce IFNγ production or IL10 production from the appropriate CTLs.

FIGS. 6A and 6B are the corresponding dose response curves for production of IFNγ and IL10 by successful heteroclitic analogs of p53.149M2.

Figure 9:
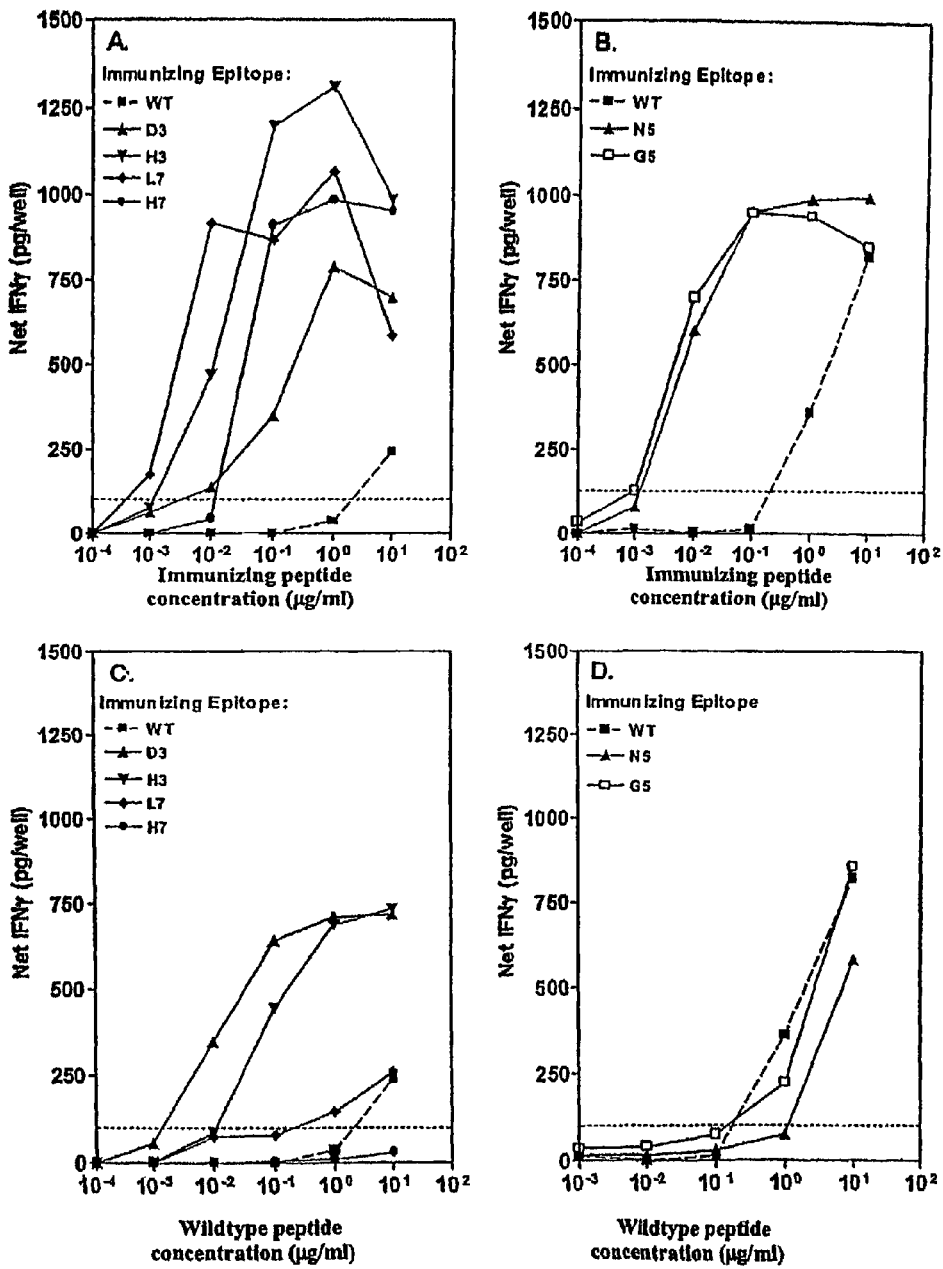

FIGS. 9A-9D show the cross-reactivity of heteroclitic analogs with regard to the corresponding wildtype epitope. In FIGS. 9A and 9B, IFNγ production is plotted as a function of concentration using stimulation by the immunizing peptide. FIGS. 9C and 9D show the corresponding results when wildtype epitope is used as the stimulant as opposed to the heteroclitic analog used for the initial induction of CTL.

Figure 10:
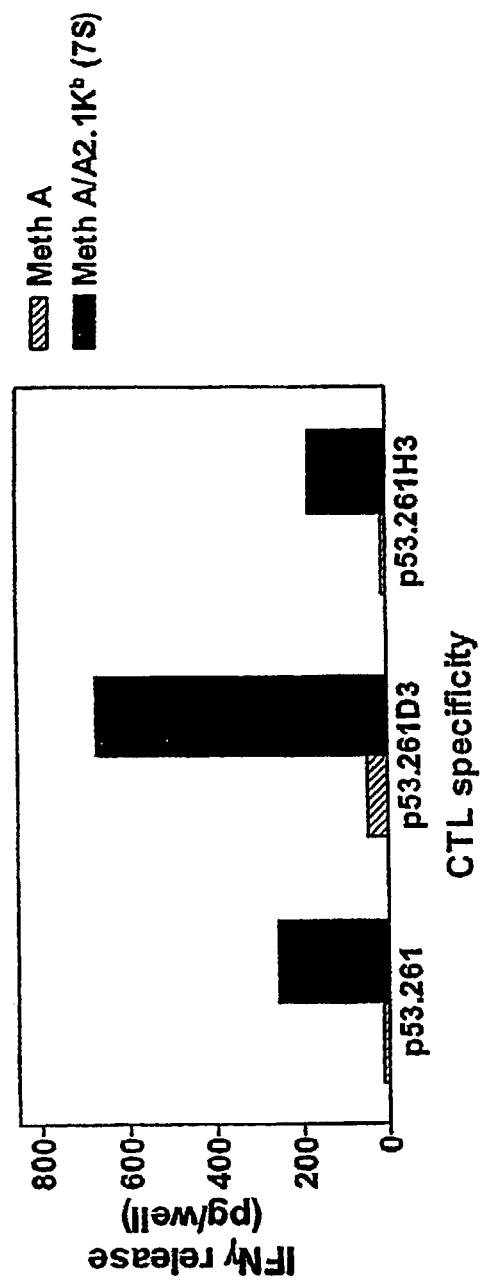

FIG. 10 shows the IFNγ release with respect to stimulation by p53.261 and its heteroclitic analogs.

Figure 11:
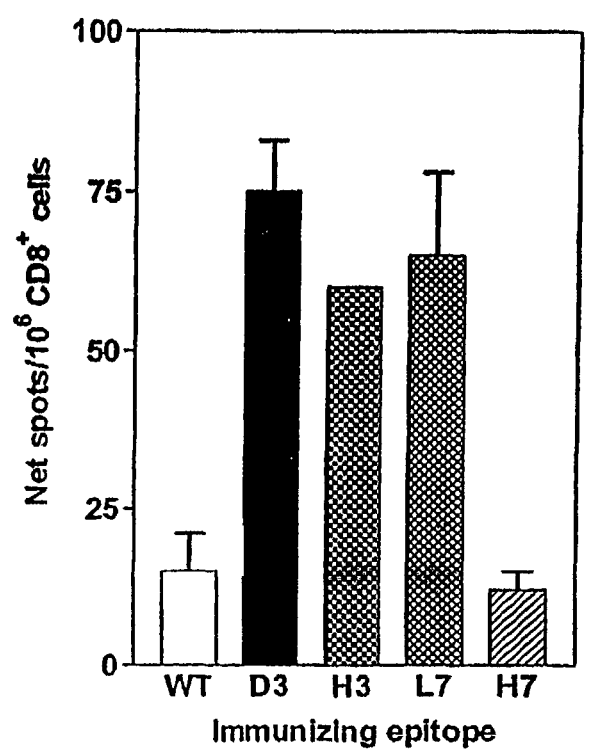

FIG. 11 shows Elispot results with respect to various heteroclitic analogs.

Figure 12:
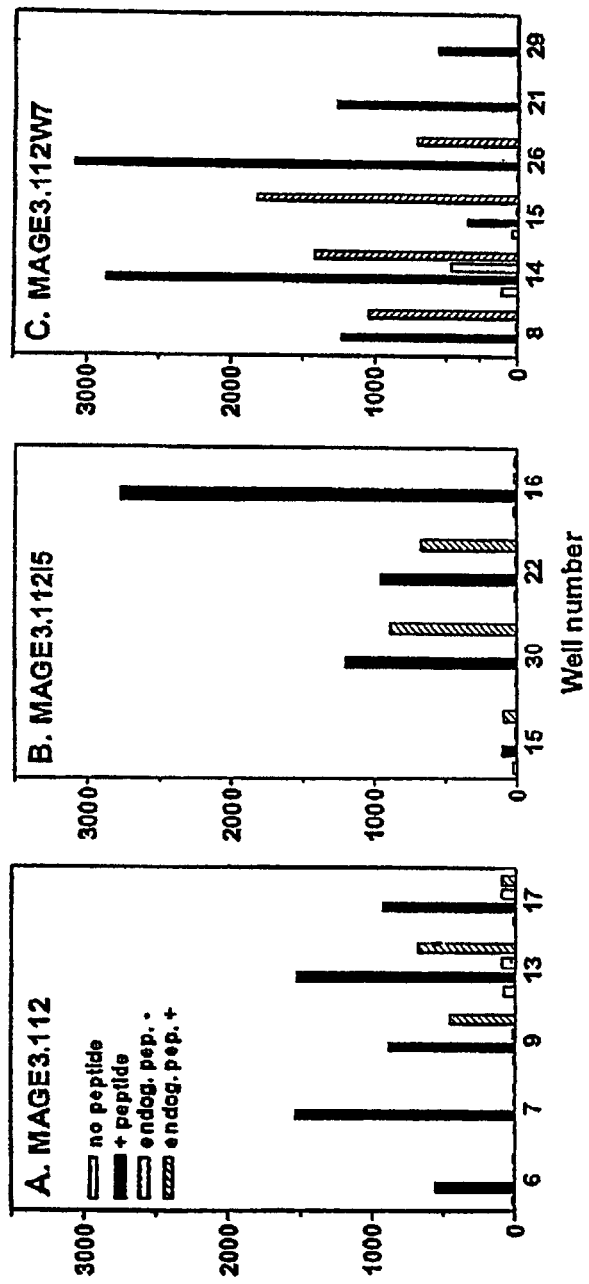

FIGS. 12A-12C show the results of stimulation of CTL activity against endogenous peptide using various heteroclitic analogs.

Figures 13A, 13B:
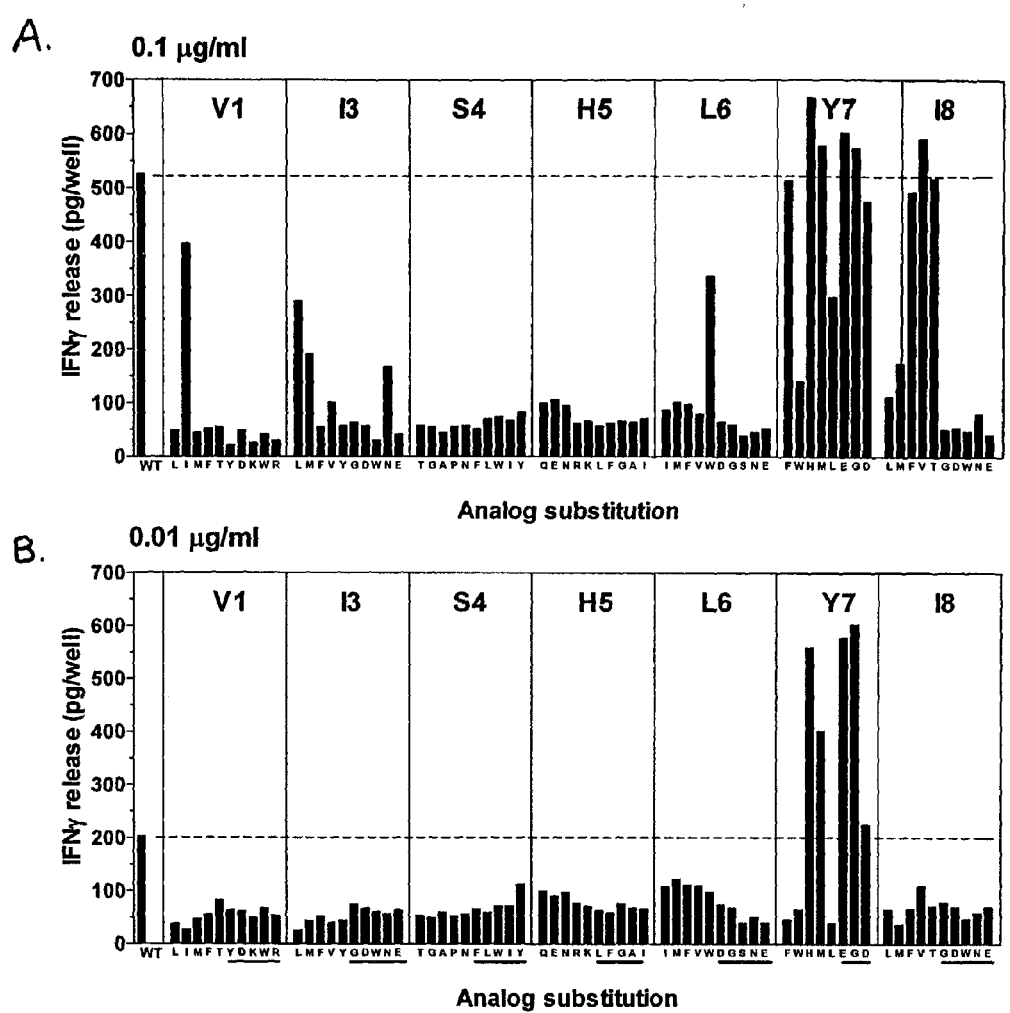

FIGS. 13A-13B show the results of testing a panel of potential heteroclitic analogs of the epitope MAGE2.170 with respect to IFNγ production from appropriate CTLs. Single residue substitutions, either conservative/semi-conservative or non-conservative in nature, were introduced in the MAGE2.170 epitope at every non-MHC anchor position.

Peptide analogs were screened for their capacity to stimulate a human CTL line specific for the MAGE2.170 wildtype epitope at two peptide doses. CTL responses were measured by stimulating CTL in vitro with peptide at the two indicated doses in the presence of GM3107 tumor cells as APC. IFNγ production of stimulated CTL was measured by ELISA. The x-axis shows the substituted residue (underlined residues denote non-conservative substitutions) and each response bar corresponds to the stimulatory activity of that analog. The native residue at the given position in the MAGE2.170 epitope is shown at the top of each panel.

Figure 14:
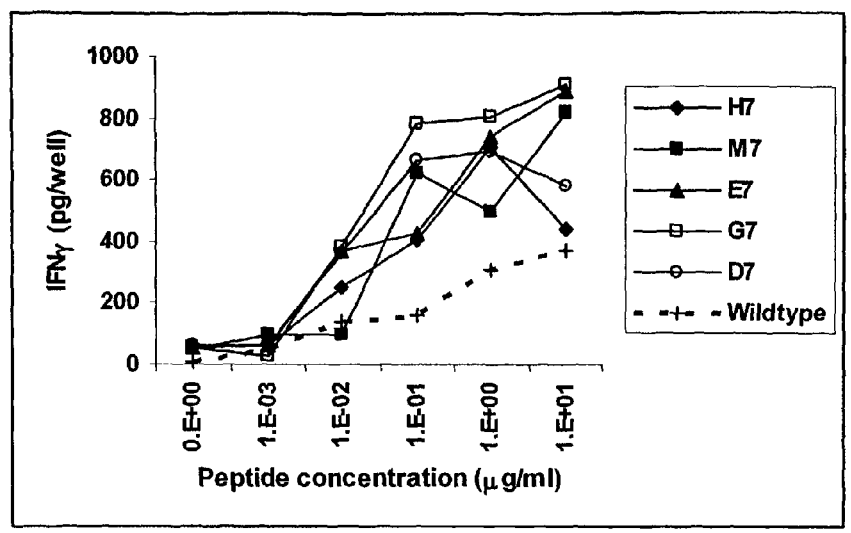

FIG. 14 shows dose response curves of heteroclitic analogs of MAGE2.170 in comparison to wildtype with regard to their ability to induce IFNγ. Analogs with hyperstimulatory activity identified in the initial screening assay were tested for CTL stimulation in a peptide dose titration. Each analog was tested in a dose titration against a human CTL line specific for the wildtype epitope and GM3107 cells as APC. IFNγ release was measured with an ELISA.

MODES OF CARRYING OUT THE INVENTION

1. Overview

The present invention relates to methods of designing heteroclitic analogs that bind to HLA Class I molecules. "Heteroclitic analogs," as described herein, are peptides comprising epitopes with increased potency for a specific T cell, as measured by increased responses to a given dose, or by a requirement of lesser amounts to achieve the same response as a homologous Class I peptide. The methods of the invention are useful to modify any Class I peptide, particularly those associated with human cancers and precancerous conditions, and from infectious agents such as viruses, bacteria, fungi, and protozoal parasites.

Importantly, the phenomenon of heteroclicity applies across HLA molecules that bind a particular Class I peptide. For example, a heteroclitic analog peptide bearing the A2 supermotif is heteroclitic (i.e., has higher potency) across all HLA molecules in the HLA-supertype (e.g., A*0201, A*0202, A*0203, A*0204, A*0205, A*0206, A*0207, etc.; see Table 5). Similarly, a heteroclitic analog peptide bearing the B7 supermotif is heteroclitic across all HLA molecules in the HLA-supertype (e.g., B*0702, B*0703, B*0704, B*0705, B*1508, B*3501, B*3502, B*3503, B*3503, B*3504, B*3505, B*3506, B*3507, B*3508, B*5101, B*5102, B*5103, B*5104, B*5105, B*5301, B*5401, B*5501, B*5502, B*5601, B*5602, B*6701, B*7801, etc.; see Table 5). Thus, a heteroclitic analog peptide bearing a different sequence motif (e.g., A1, A2, A3, A24, B7, B27, B44, B58, B62, etc.) induces a more potent immune response across all HLA molecules within their specific HLAsuperfamily.

Applicants have found specific rules for designing heteroclitic analogs which enhance the immune response to the corresponding wildtype epitope. These rules are applicable with respect to epitopes bearing motifs or supermotifs which bind to HLA molecules encoded by any Class I allele. By using these rules, it is possible to enhance the immunogenicity, therefore, of any "wildtype" or "native" Class I epitope.

Briefly, the rules state that the wildtype Class I epitope is modified by substituting a conservative or semi-conservative amino acid as position 3 and/or 5 and/or 7 of the epitope. For B7 superfamily epitopes, the rule states that the wildtype Class I epitope (i.e., the B7 superfamily epitope) is modified by substituting a conservative or semi-conservative or non-conservative amino acid as position 3 and/or 5 and/or 7 of the epitope. The nature of the conservative or semi-conservative or non-conservative amino acid to be substituted is defined by the description in Preparation B hereinbelow, the results of which are summarized in Table 2. Thus, by consulting Table 2, one can determine suitable candidates for substitution at these positions. As shown in Table 2, each of the amino acids shown across the top of the table bears a numerically defined relationship to the remaining 19 genetically encoded amino acids. The lower the index, the higher the conservation; the same amino acid will have a similarity assignment of 1.0; maximally different amino acids will have similarity assignments approaching 20. Using the method set forth in Preparation B, amino acids which are not gene-encoded can also be assigned similarity indices and can be classified with respect to any natively occurring amino acid as conservative or semi-conservative (or non-conservative).

Heteroclitic analog peptides of the invention are particularly useful to induce an immune response against antigens to which a subject's immune system has become tolerant. Human subjects are particularly preferred, but the methods can also be applied to other mammals such as laboratory mice, taking account of the corresponding HLA motifs with regard to these subjects. Tolerance refers to a specific immunologic nonresponsiveness induced by prior exposure to an antigen. Tolerance can be overcome by identifying a particular Class I peptide epitope to which a patient is tolerant, modifying the peptide epitope sequence according to the methods of the invention, and inducing an immune response that cross-reacts against the tolerized epitope (antigen). Overcoming tolerance is particularly desirable, for example, when the immune system of the subject is tolerant of a viral or tumor-associated antigen, the latter antigens being often overexpressed self-proteins as a consequence of cell transformation.

To determine rules for designing heteroclitics, several different CTL lines were screened for reactivity against panels of analogs. Modification of T cell stimulatory capacity was achieved with no alternation of the primary MHC anchors.

The wildtype epitopes include tumor epitopes derived from self antigens that are specifically up-regulated in epithelial cell cancers and have been shown to be immunogenic. Viral epitopes used, such as those from the polymerase genes of the HIV and HBV, have been shown to be immunogenic as well.

The rules described herein provide a basis to design heteroclitic analogs, drastically reducing the screening otherwise required and are extremely useful in designing epitope-based vaccines for cancer and infectious diseases.

In the examples set forth below, 17% of the total analogs screened (which fit the heteroclicity rules disclosed herein) were heteroclitic (16/95). This is significant for two reasons: first, the efficiency of detecting heteroclitics increased from 2.2% to 17% by employing analogs that follow the rules of heteroclitic substitution; second, the number of peptides which need to be synthesized is reduced dramatically from about a 100 analogs per epitope to about 15 analogs per epitope, making the process cost effective and amenable to high throughput. Through the application of the heteroclitic substitution rules of the invention, the efficiency of generating heteroclitic analogs was increased nearly 100 to 1000-fold, from 0.2% (4 identified from screening of 233 CEA.691 and MAGE3.112 analogs) to 33% (3 identified by screening of 9 predicted analogs). The latter frequency may be a gross underestimate since only 4 of 6 analogs showing potential heteroclitic activity in initial assays were subjected to further analysis.

Previous studies showed that modulation of T cell responses by heteroclitic analogs involved TCR contact residues (Byrne, et al., *J. Immunol.* 51:682 (1984), McMichael, et al., *N. England. J. Med.* 309:13 (1983), Zugel, et al., *J. Immunol.* 161:1705 (1998), Rivoltini, et al., *Cancer Research* 59:301 (1999)), but the present study did not find this. For example, for the CEA.691 epitope, the TCR contact residue is position 8, while heteroclicity was observed with analog substitutions at positions 3 and 5. While not intending to be bound by any theory, alteration of MHC binding may be a mechanism. Binding analyses performed on the analogs indicated that there is an alteration in MHC binding for the better or worse in a majority of cases (80%). Out of the 13 analogs which were tested for HLA-A2 binding, ten analogs had alteration in MHC binding, with six analogs binding better than wildtype peptides and four analogs that bound worse than wildtype, but still generated a substantially increased biological response. Some studies modify primary MHC anchor residues in order to increase MHC binding (this approach has been used by some groups to generate analogs (Pfeiffer, et al., *J. Exp. Med.* 181:1569 (1995), Valmori, et al., *J. Immunol.* 160:1750-1758 (1998), Parkhurst, et al., *J. Immunol.* 157:2539 (1996)). Increased biological responses without changing primary TCR contact residues or primary MHC anchor residues was observed in this study. Since increased responses were mediated with alteration in MHC binding, it is postulated that the effect may be mediated by changing secondary anchor positions. More evidence supporting this comes from the finding that heteroclitic substitutions occur at odd numbered positions (3, 5, 7) in the middle of the peptide. All these positions 3, 5, and 7 have been shown to be secondary anchor positions for binding to the HLA-A2 molecule (Ruppert, et al., *Cell* 74:929 (1993), Madden, *Annu. Rev. Immunol.* 13:587-622 (1995)).

Two of these positions (3 and 7) have been shown to be secondary anchor positions for binding to HLA-A2.1 molecule by several groups (Ruppert, et al., *Cell* 74:929 (1993), Madden, *Annu. Rev. Immunol.* 13:587-622 (1995)). Alteration of such secondary anchor positions can translate into T cell recognition differences (Valmori, et al., *J. Immonol.* 160: 1750 (1998); Davis, et al., *Annu. Rev. Immunol.* 16:523 (1998)), however in these studies T cell recognition differences were associated with changes in MHC binding and no rules were defined for the kinds of amino acid substitutions involved in obtaining heteroclicity. The mechanism by which such a translation from changing secondary anchors to change in T cell recognition takes place is currently unclear. However, some models suggest that changes in the way residues at secondary anchor positions engage the MHC may lead to alteration in the orientation or increased flexibility of TCR contact residues, resulting in enhancement of the binding of these analogs to the TCR (Kersh, et al., *J. Exp. Med.* 184:1259 (1996), Evavold, et al., *J. Immunol.* 148:347 (1992), Alam, et al., *Immunity* 10:227 (1999), Hampl, et al., *Immunity* 7:379-85 (1997)). Also, some previous studies implied that modulation of T cell responses by heteroclitic analogs directly involve main TCR contact residues (Zaremba, et al., *Cancer Research* 57:4570 (1997), Loftus, et al., *Cancer Research* 58:2433 (1998), Dressel, et al., *J. Immunol* 159:4943 (1997)). This finding, however, is not corroborated by the current systematic analysis. The enhanced T cell recognition against analogs identified in the present study is not likely due to increases in MHC binding capacity, though increased binding is likely to play an important role in the case of analogs in which primary anchor positions have been optimized. The present study suggests that heteroclitic analogs are most likely generated by subtle alterations in conformation rather than by gross alterations of TCR or MHC binding capacity.

Differential regulation of production of Th1 or Th2 cytokines was not observed. Instead, the present data suggested that the heteroclitic analogs increased the production of both Th1 and Th2 responses, although the magnitude and kinetics of the increase may be different. In fact, some groups (Nicholson, et al., *Int. Immunol.* 12(2):205-13 (2000), Parkhurst, et al., *J. Immunol.* 157:2539 (1996)) have recently reported such overall stimulation by peptide analogs. This is attributable to a stronger TCR signal induced by analogs, though the mechanism of such overall stimulation remains to be elucidated.

The efficacy of heteroclitic analogs in vivo using relevant tumor models or models in which tolerance to self antigens exists is evaluated. Accordingly, it is found that immunization with heteroclitic analogs is a more effective and efficient strategy for vaccination against tumors where raising effective CTLs has so far proved to be a challenge.

To summarize, in a set of experiments, applicants have identified heteroclitic analogs of a number of different HLA-A2.1-restricted CTL epitopes of cancer and viral origin. The relevant wildtype epitopes are shown in Table 1. All these epitopes have been shown to be immunogenic in our earlier reports (Kawashima, et al., *Human Immunology* 59:1-14 (1998), Ishioka, et al., *J. Immunol.* 162(7):3915-25 (1999)). In initial experiments, the antigenicity of 233 analogs of the CEA.691 and MAGE3.112 CTL epitopes was investigated. The nature of the four heteroclitic analogs identified suggested that heteroclitic substitutions involved conservative substitutions at positions 3, 5 and 7. This hypothesis, was tested in a subsequent study involving three additional epitopes MAGE2.157, HIVPol.476, and HBVPol.455. All of the heteroclitic analogs thus identified conformed to the rules proposed, namely that heteroclitic analogs were associated with conservative or semi-conservative substitutions at positions 3, 5 and/or 7.

To more closely mimic the clinical application of heteroclitic analogs in cancer immunotherapy, the murine epitope, p53.261 was also modified. A partial state of T cell tolerance has been reported for this epitope (Theobald, et al., *Proc. Natl. Acad. Sci.* 92:11993-11997 (1995), Theobald, et al., *J. Exp. Med.,* 185(5):833-841 (1997)). Four out of nine predicted p53.261 analogs were found to induce stronger analog-specific CTL responses in vivo compared to the CTL responses induced by the native peptide. More significantly, when the cross-reactivity of the CTL raised by immunization with heteroclitic analogs was analyzed, three p53.261 analogs induced CTL which responded vigorously against the native p53.261 epitope. Finally, the relevance of these findings for human CTL was addressed by demonstrating that heteroclitic analogs of the MAGE3.112 epitope are immunogenic for human T cells in vitro. The resulting CTL can recognize wildtype naturally processed antigen in the form of tumor cell lines.

The studies presented herein demonstrate that heteroclicity is a global phenomenon, as heteroclitic analogs were identified for all the epitopes studied. In addition, the present application shows that it is possible to detect heteroclitic analogs both in clonal T cell populations (as has been described earlier studies) as well as in bulk T cell populations following in vivo immunization. Moreover, it is demonstrated herein that heteroclicity (both in the HLA A2.1 system as well as for other Class I supermotifs) is associated with discrete structural features which allow rational prediction of heteroclicity.

It is demonstrated, further that p53.261 heteroclitic analogs induce CTLs with higher avidity and also induced these cells in greater numbers (precursor frequency) than those induced with wildtype peptide; heteroclitic CTL induction in vivo, and its application to breaking T cell tolerance is demonstrated.

The heteroclitic analogs were effective in raising bulk populations of specific T cells following in vivo immunization. Polyclonal responses that bear TCR from multiple TCR genes, are more efficacious in resolving disease states in a clinical setting. Finally, the ability to generate high precursor frequencies of CTL possessing strong cross-reactive avidity against wildtype epitope is important in instances where effective CTL responses against epitopes, normally tolerant to the immune system, are required.

In another set of experiments, applicants identified heteroclitic analogs of the B7 superfamily epitope MAGE2.170 (shown in Table 1). Like A2 heteroclitic epitopes, heteroclitic analogs of the B7 superfamily epitope could be generated by introducing substitutions at an odd-number position in the middle of the peptide (position 7). The nature of the substitutions for the MAGE2.170 epitope were either conservative/semi-conservative (the Y→H and Y→M substitutions) or non-conservative (the Y→E, Y→G, and Y→D substitutions) compared to the native residue (Table 5). Thus, the observation that non-conservative substitutions can result in heteroclitic analogs for the MAGE2.170 CTL epitope indicate a partially overlapping substitution pattern than that observed with A2 superfamily epitopes.

2. Definitions

With regard to a particular amino acid sequence, an "epitope" is a set of amino acid residues which is involved in recognition by a particular immunoglobulin, or in the context of T cells, those residues necessary for recognition by T cell receptor proteins when presented in the context of an HLA encoded by the Major Histocompatibility Complex (MHC). In an immune system setting, in vitro or in vivo, an epitope is the collective features of a molecule, such as primary, secondary and tertiary peptide structure, and charge, that together form a site recognized by an immunoglobulin, T cell receptor or HLA molecule. Throughout this disclosure epitope and peptide are often used interchangeably. It is to be appreciated, however, that isolated or purified protein or peptide molecules larger than and comprising an epitope of the invention are still within the invention.

A "Class I epitope" refers to a peptide that binds to a Class I HLA molecule. As described herein, a Class I epitope is typically about 8 to about 13 amino acids in length. Binding to the HLA molecule is primarily controlled by two primary anchor residues, one of which is at the C-terminus of the epitope and the other of which is at positions 2 or 3. Binding may be aided also by one or more secondary anchor residues. For the convenience of the reader, various primary HLA Class I binding anchors are set forth in Table 3. The pattern of anchors is referred to as a "motif." A "supermotif" is a peptide binding specificity shared by HLA molecules encoded by two or more HLA alleles. Preferably, a supermotif-bearing peptide is recognized with high or intermediate affinity (as defined herein) by two or more HLA antigens. Examples of Class I supermotifs include, e.g., A1, A2, A3, A24, B7, B27, B44, B58 and B62.

Throughout this disclosure, "binding data" results are often expressed in terms of "$IC_{50}$'s." $IC_{50}$ is the concentration of peptide in a binding assay at which 50% inhibition of binding of a reference peptide is observed. Given the conditions in which the assays are run (i.e., limiting HLA proteins and labeled peptide concentrations), these values approximate Kd values. Assays for determining binding are described in detail, e.g., in PCT publications WO 94/20127 and WO 94/03205, incorporated herein by reference. It should be noted that $IC_{50}$ values can change, often dramatically, if the assay conditions are varied, and depending on the particular reagents used (e.g., HLA preparation, etc.). For example, excessive concentrations of HLA molecules will increase the apparent measured $IC_{50}$ of a given ligand. Alternatively, binding is expressed relative to a reference peptide. Although as a particular assay becomes more, or less, sensitive, the $IC_{50}$'s of the peptides tested may change somewhat, the binding relative to the reference peptide will not significantly change. For example, in an assay run under conditions such that the $IC_{50}$ of the reference peptide increases 10-fold, the $IC_{50}$ values of the test peptides will also shift approximately 10-fold. Therefore, to avoid ambiguities, the assessment of whether a peptide is a good, intermediate, weak, or negative binder is generally based on its $IC_{50}$, relative to the $IC_{50}$ of a standard peptide. Binding may also be determined using other assay systems known in the art.

The designation of a residue position in an epitope as the "carboxyl or C-terminus" refers to the residue position at the end of the epitope which is nearest to the carboxyl terminus of a peptide, which is designated using conventional nomenclature as defined below. The "C-terminus" of the epitope may or may not actually correspond to the end of the peptide or polypeptide.

The designation of a residue position in an epitope as "N-terminus" or "amino-terminal position" refers to the residue position at the end of the epitope which is nearest to the N-terminus of a peptide, which is designated using conventional nomenclature as defined below. The "N-terminus" of the epitope may or may not actually correspond to the end of the peptide or polypeptide.

A "computer" or "computer system" generally includes: a processor; at least one information storage/retrieval apparatus such as, for example, a hard drive, a disk drive or a tape drive; at least one input apparatus such as, for example, a keyboard, a mouse, a touch screen, or a microphone; and display structure. Additionally, the computer may include a communication channel in communication with a network. Such a computer may include more or less than what is listed above.

As used herein amino acids that are "conserved" or "conservative," and "semi-conserved" or "semi-conservative," and "non-conserved" or "non-conservative" are defined in accordance with Preparation B and set forth in Table 2.

As used herein, "high affinity" with respect to HLA Class I molecules is defined as binding with an $IC_{50}$, or $K_D$ value, of 50 nM or less; "intermediate affinity" is binding with an $IC_{50}$ or $K_D$ value of between about 50 and about 500 nM. "High affinity" with respect to binding to HLA Class II molecules is defined as binding with an $IC_{50}$ or $K_D$ value of 100 nM or less; "intermediate affinity" is binding with an $IC_{50}$ or $K_D$ value of between about 100 and about 1000 nM.

An "immunogenic peptide" or "peptide epitope" is a peptide that comprises an allele-specific motif or supermotif such that the peptide will bind an HLA molecule and induce a CTL and/or HTL response. Thus, immunogenic peptides of the invention are capable of binding to an appropriate HLA molecule and thereafter inducing a cytotoxic T cell response, or a helper T cell response, to the antigen from which the immunogenic peptide is derived.

The phrases "isolated" or "biologically pure" refer to material that is substantially or essentially free from components which normally accompany the material as it is found in its native state. Thus, isolated peptides in accordance with the invention preferably do not contain materials normally associated with the peptides in their in situ environment.

A "PanDR binding peptide" is a member of a family of molecules that binds more that one HLA Class II DR molecule (e.g., PADRE™ peptide, Epimmune Inc., San Diego, Calif.). The pattern that defines the PADRE™ family of molecules can be thought of as an HLA Class II supermotif. Peptides comprising the pattern found in PADRE™ molecules bind to most HLA-DR molecules and stimulate in vitro and in vivo human helper T lymphocyte (HTL) responses.

"Pharmaceutically acceptable" refers to a generally nontoxic, inert, and/or physiologically compatible composition.

3. Peptides of the Invention

Peptides in accordance with the invention can be prepared synthetically, by recombinant DNA technology or chemical synthesis, or from natural sources such as native tumors or pathogenic organisms. Peptide epitopes may be synthesized individually or as polyepitopic peptides. Although the peptide will preferably be substantially free of other naturally occurring host cell proteins and fragments thereof, in some embodiments the peptides may be synthetically conjugated to native fragments or particles.

HLA Class I peptides are well known in the art and are defined as peptides that bind to MHC Class I molecules. The peptides in accordance with the invention can be a variety of lengths, and either in their neutral (uncharged) forms or in forms which are salts. The peptides in accordance with the invention are either free of modifications such as glycosylation, side chain oxidation, or phosphorylation; or they contain these modifications, subject to the condition that modifications do not destroy the biological activity of the peptides as described herein.

Class I epitopes that serve as the corresponding "wildtype" can be derived from any proteinaceous source. For example, the Class I peptides can be derived from viral antigens, tumor-associated antigens, parasitic antigens, bacterial antigens or fungal antigens. In some preferred aspects of the invention, the Class I peptide(s) are derived from antigens for which a the immune system of a subject has developed a tolerance, i.e., a specific immunologic nonresponsiveness induced by prior exposure to an antigen.

Thus, heteroclitic analogs based on a number of potential target epitopes can be used in the present invention. Examples of suitable tumor-associated antigens include prostate specific antigens (PSA), melanoma antigens MAGE 1, MAGE 2, MAGE 3, MAGE-11, MAGE-A10, as well as BAGE, GAGE, RAGE, MAGE-C1, LAGE-1, CAG-3, DAM, MUC1, MUC2, MUC18, NY-ESO-1, MUM-1, CDK4, BRCA2, NY-LU-1, NY-LU-7, NY-LU-12, CASP8, RAS, KIAA-2-5, SCCs, p53, p73, CEA, Her 2/neu, Melan-A, gp100, tyrosinase, TRP2, gp75/TRP1, kallikrein, prostate-specific membrane antigen (PSM), prostatic acid phosphatase (PAP), prostate-specific antigen (PSA), PT1-1, β-catenin, PRAME, Telomerase, FAK, cyclin D1 protein, NOEY2, EGF-R, SART-1, CAPB, HPVE7, p15, Folate receptor CDC27, PAGE-1, and PAGE-4. Examples of suitable infectious disease-associated antigens include hepatitis B core and surface antigens (HBVc, HBVs), hepatitis C antigens, Epstein-Barr virus antigens, human immunodeficiency virus (HIV) antigens and human papilloma virus (HPV) antigens, *Mycobacterium tuberculosis* and Chlamydia. Examples of suitable fungal antigens include those derived from *Candida albicans, Cryptococcus neoformans, Coccidoides* spp., *Histoplasma* spp, and *Aspergillus fumigatis*. Examples of suitable protozoal parasitic antigens include those derived from *Plasmodium* spp., including *P. falciparum, Trypanosoma* spp., *Schistosoma* spp., *Leishmania* spp and the like.

The epitopes that may be used as wildtype sequences to which the rules of the invention are applied to construct corresponding heteroclitic analogs can be found corresponding to any Class I epitope. For any desired antigen, such as those set forth above, the motif associated with a particular Class I allele can be used as a guide to determine the positions in the amino acid sequence of the antigen wherein such an epitope would reside. This determination can be done visually or, preferably, using computer technology and associated software. Thus, for example, by recognition of the A3 supermotif as containing, for example, valine in position 2 and arginine at the C-terminus, the amino acid sequence of any desired antigen can be surveyed for epitopes bearing this motif. That epitope can then be modified according to the rules set forth in the present invention to obtain the desired analogs.

When possible, it may be desirable to optimize HLA Class I binding epitopes of the invention, such as can be used in a polyepitopic construct, to a length of about 8 to about 13 amino acid residues, often 8 to 11, preferably 9 to 10. Preferably, the peptide epitopes are commensurate in size with endogenously processed pathogen-derived peptides or tumor cell peptides that are bound to the relevant HLA molecules, however, the identification and preparation of peptides that comprise epitopes of the invention can also be carried out using the techniques described herein.

In alternative embodiments, epitopes of the invention can be linked as a polyepitopic peptide, or as a minigene that encodes a polyepitopic peptide.

In another embodiment, it is preferred to identify native peptide regions that contain a high concentration of Class I epitopes and/or Class II epitopes. Such a sequence is generally selected on the basis that it contains the greatest number of epitopes per amino acid length. It is to be appreciated that epitopes can be present in a nested or overlapping manner, e.g., a 10 amino acid long peptide could contain two 9 amino acid long epitopes and one 10 amino acid long epitope; upon intracellular processing, each epitope can be exposed and bound by an HLA molecule upon administration of such a peptide. This larger, preferably multi-epitopic, peptide can be generated synthetically, recombinantly, or via cleavage from the native source.

The peptides of the invention can be prepared in a wide variety of ways. For the preferred relatively short size, the peptides can be synthesized in solution or on a solid support in accordance with conventional techniques. Various automatic synthesizers are commercially available and can be used in accordance with known protocols. (See, for example, Stewart & Young, SOLID PHASE PEPTIDE SYNTHESIS, 2D. E D., Pierce Chemical Co., 1984). Further, individual peptide epitopes can be joined using chemical ligation to produce larger peptides that are still within the bounds of the invention.

Alternatively, recombinant DNA technology can be employed wherein a nucleotide sequence which encodes an immunogenic peptide of interest is inserted into an expression vector, transformed or transfected into an appropriate host cell and cultivated under conditions suitable for expression. These procedures are generally known in the art, as described generally in Sambrook, et al., MOLECULAR CLONING, A LABORATORY MANUAL, Cold Spring Harbor Press, Cold Spring Harbor, N.Y. (1989). Thus, recombinant polypeptides which comprise one or more peptide sequences of the invention can be used to present the appropriate T cell epitope.

The nucleotide coding sequence for peptide epitopes of the preferred lengths contemplated herein can be synthesized by chemical techniques, for example, the phosphotriester method of Matteucci, et al., *J. Am. Chem. Soc.* 103:3185 (1981). Peptide analogs can be made simply by substituting the appropriate and desired nucleic acid base(s) for those that encode the native peptide sequence; exemplary nucleic acid substitutions are those that encode an amino acid defined by the motifs/supermotifs herein. The coding sequence can then be provided with appropriate linkers and ligated into expression vectors commonly available in the art, and the vectors used to transform suitable hosts to produce the desired fusion protein. A number of such vectors and suitable host systems are now available. For expression of the fusion proteins, the coding sequence will be provided with operably linked start and stop codons, promoter and terminator regions and usually a replication system to provide an expression vector for expression in the desired cellular host. For example, promoter sequences compatible with bacterial hosts are provided in plasmids containing convenient restriction sites for insertion of the desired coding sequence. The resulting expression vectors are transformed into suitable bacterial hosts. Of course, yeast, insect or mammalian cell hosts may also be used, employing suitable vectors and control sequences.

Analogs of the present invention may include peptides containing substitutions to modify the physical property (e.g., stability or solubility) of the resulting peptide. For example, peptides may be modified by the substitution of a cysteine (C) with α-amino butyric acid. Due to its chemical nature, cysteine has the propensity to form disulfide bridges and sufficiently alter the peptide structurally so as to reduce binding capacity. Substituting α-amino butyric acid for C not only alleviates this problem, but actually improves binding and crossbinding capability in certain instances. Substitution of cysteine with α-amino butyric acid may occur at any residue of a peptide epitope, i.e. at either anchor or non-anchor positions.

Modified peptides that have various amino acid mimetics or unnatural amino acids are particularly useful, as they tend to manifest increased stability in vivo. Such analogs may also possess improved shelf-life or manufacturing properties. More specifically, non-critical amino acids need not be limited to those naturally occurring in proteins, such as L-α-amino acids, or their D-isomers, but may include non-natural amino acids as well, such as amino acids mimetics, e.g. D- or L-naphylalanine; D- or L-phenylglycine; D- or L-2-thieneylalanine; D- or L-1, -2, 3-, or 4-pyreneylalanine; D- or L-3 thieneylalanine; D- or L-(2-pyridinyl)-alanine; D- or L-(3-pyridinyl)-alanine; D- or L-(2-pyrazinyl)-alanine; D- or L-(4-isopropyl)-phenylglycine; D-(trifluoromethyl)-phenylglycine; D-(trifluoromethyl)-phenylalanine; D-ρ-fluorophenylalanine; D- or L-ρ-biphenylphenylalanine; D- or L-ρ-methoxybiphenylphenylalanine; D- or L-2-indole(alkyl) alanines; and, D- or L-alkylalanines, where the alkyl group can be a substituted or unsubstituted methyl, ethyl, propyl, hexyl, butyl, pentyl, isopropyl, iso-butyl, sec-isotyl, iso-pentyl, or a non-acidic amino acids. Aromatic rings of a nonnatural amino acid include, e.g., thiazolyl, thiophenyl, pyrazolyl, benzimidazolyl, naphthyl, furanyl, pyrrolyl, and pyridyl aromatic rings.

Peptide stability can be assayed in a number of ways. For instance, peptidases and various biological media, such as human plasma and serum, have been used to test stability. See, e.g., Verhoef, et al., *Eur. J. Drug Metab. Pharmacokinetics* 11:291 (1986). Half life of the peptides of the present invention is conveniently determined using a 25% human serum (v/v) assay. The protocol is generally as follows: Pooled human serum (Type AB, non-heat inactivated) is delipidated by centrifugation before use. The serum is then diluted to 25% with RPMI-1640 or another suitable tissue culture medium. At predetermined time intervals, a small amount of reaction solution is removed and added to either 6% aqueous trichloroacetic acid (TCA) or ethanol. The cloudy reaction sample is cooled (4° C.) for 15 minutes and then spun to pellet the precipitated serum proteins. The presence of the peptides is then determined by reversed-phase HPLC using stability-specific chromatography conditions.

4. Class I Motifs

In the past few years, evidence has accumulated to demonstrate that a large fraction of HLA Class I molecules can be classified into a relatively few supertypes, each characterized by largely overlapping peptide binding repertoires, and consensus structures of the main peptide binding pockets. Thus, peptides of the present invention are identified by any one of several HLA-specific amino acid motifs (see, e.g., Tables 3-4), or if the presence of the motif corresponds to the ability to bind several allele-specific HLA antigens, a supermotif. The HLA molecules that bind to peptides that possess a particular amino acid supermotif are collectively referred to as an HLA "supertype."

For the convenience of the reader, the peptide motifs and supermotifs described below, and summarized in Tables 3-4, provide guidance for the identification and use of peptide epitopes in accordance with the invention. This will permit identification of candidate wildtype epitopes corresponding to various Class I motifs different from those illustrated in the examples below or epitopes bearing those illustrated below but in different antigens in order to apply the rules set forth herein to construct analogs.

Heteroclitic analogs can be designed according to the methods of the invention from a peptide, without regard to the motif or supermotif to which the peptide belongs. The primary anchor residues of the HLA Class I peptide epitope supermotifs and motifs delineated below are summarized in Table 3. The HLA Class I motifs set out in Table 4 are those most particularly relevant to the invention claimed here. Allele-specific HLA molecules that comprise HLA Class I supertype families are listed in Table 5. In some cases, peptide epitopes may be listed in both a motif and a supermotif. The relationship of a particular motif and respective supermotif is indicated in the description of the individual motifs.

i. HLA-A1 Supermotif

The HLA-A1 supermotif is characterized by the presence in peptide ligands of a small (T or S) or hydrophobic (L, I, V, or M) primary anchor residue in position 2, and an aromatic (Y, F, or W) primary anchor residue at the C-terminal position of the epitope. The corresponding family of HLA molecules that bind to the A1 supermotif (i.e., the HLA-A1 supertype) is comprised of at least A*0101, A*2601, A*2602, A*2501, and A*3201 (see, e.g., DiBrino, M. et al., *J. Immunol.* 151:5930, 1993; DiBrino, M. et al., *J. Immunol.* 152:620, 1994; Kondo, A. et al, *Immunogenetics* 45:249, 1997). Other allele-specific HLA molecules predicted to be members of the A1 superfamily are shown in Table 5.

ii. HLA-A2 Supermotif

Primary anchor specificities for allele-specific HLA-A2.1 molecules (see, e.g., Falk et al., *Nature* 351:290-296, 1991; Hunt et al., *Science* 255:1261-1263, 1992; Parker et al., *J. Immunol.* 149:3580-3587, 1992; Ruppert et al., *Cell* 74:929-937, 1993) and cross-reactive binding among HLA-A2 and -A28 molecules have been described. (See, e.g., Fruci et al., *Human Immunol.* 38:187-192, 1993; Tanigaki et al., *Human*

Immunol. 39:155-162, 1994; Del Guercio et al., J. Immunol. 154:685-693, 1995; Kast et al., J. Immunol. 152:3904-3912, 1994 for reviews of relevant data.) These primary anchor residues define the HLA-A2 supermotif; which presence in peptide ligands corresponds to the ability to bind several different HLA-A2 and -A28 molecules. The HLA-A2 supermotif comprises peptide ligands with L, I, V, M, A, T, or Q as a primary anchor residue at position 2 and L, I, V, M, A, or T as a primary anchor residue at the C-terminal position of the epitope.

The corresponding family of HLA molecules (i.e., the HLA-A2 supertype that binds these peptides) is comprised of at least: A*0201, A*0202, A*0203, A*0204, A*0205, A*0206, A*0207, A*0209, A*0214, A*6802, and A*6901. Other allele-specific HLA molecules predicted to be members of the A2 superfamily are shown in Table 5.

iii. HLA-A3 Supermotif

The HLA-A3 supermotif is characterized by the presence in peptide ligands of A, L, I, V, M, S, or, T as a primary anchor at position 2, and a positively charged residue, R or K, at the C-terminal position of the epitope, e.g., in position 9 of 9-mers (see, e.g., Sidney et al., Hum. Immunol. 45:79, 1996). Exemplary members of the corresponding family of HLA molecules (the HLA-A3 supertype) that bind the A3 supermotif include at least A*0301, A*1101, A*3101, A*3301, and A*6801. Other allele-specific HLA molecules predicted to be members of the A3 supertype are shown in Table 5.

iv. HLA-A24 Supermotif

The HLA-A24 supermotif is characterized by the presence in peptide ligands of an aromatic (F, W, or Y) or hydrophobic aliphatic (L, I, V, M, or T) residue as a primary anchor in position 2, and Y, F, W, L, I, or M as primary anchor at the C-terminal position of the epitope (see, e g., Sette and Sidney, Immunogenetics, in press, 1999). The corresponding family of HLA molecules that bind to the A24 supermotif (i.e., the A24 supertype) includes at least A*2402, A*3001, and A*2301. Other allele-specific HLA molecules predicted to be members of the A24 supertype are shown in Table 5.

v. HLA-B7 Supermotif

The HLA-B7 supermotif is characterized by peptides bearing proline in position 2 as a primary anchor, and a hydrophobic or aliphatic amino acid (L, I, V, M, A, F, W, or Y) as the primary anchor at the C-terminal position of the epitope. The corresponding family of HLA molecules that bind the B7 supermotif (i.e., the HLA-B7 supertype) is comprised of at least twenty six HLA-B proteins including: B*0702, B*0703, B*0704, B*0705, B*1508, B*3501, B*3502, B*3503, B*3504, B*3505, B*3506, B*3507, B*3508, B*5101, B*5102, B*5103, B*5104, B*5105, B*5301, B*5401, B*5501, B*5502, B*5601, B*5602, B*6701, and B*7801 (see, e.g., Sidney, et al., J. Immunol. 154:247, 1995; Barber, et al., Curr. Biol. 5:179, 1995; Hill, et al., Nature 360:434, 1992; Rammensee, et al., Immunogenetics 41:178, 1995 for reviews of relevant data). Other allele-specific HLA molecules predicted to be members of the B7 supertype are shown in Table 5.

vi. HLA-B27 Supermotif

The HLA-B27 supermotif is characterized by the presence in peptide ligands of a positively charged (R, H, or K) residue as a primary anchor at position 2, and a hydrophobic (F, Y, L, W, M, I, A, or V) residue as a primary anchor at the C-terminal position of the epitope (see, e.g., Sidney and Sette, Immunogenetics, in press, 1999). Exemplary members of the corresponding family of HLA molecules that bind to the B27 supermotif (i.e., the B27 supertype) include at least B*1401, B*1402, B*1509, B*2702, B*2703, B*2704, B*2705, B*2706, B*3801, B*3901, B*3902, and B*7301. Other allele-specific HLA molecules predicted to be members of the B27 supertype are shown in Table 5.

vii. HLA-B44 Supermotif

The HLA-B44 supermotif is characterized by the presence in peptide ligands of negatively charged (D or E) residues as a primary anchor in position 2, and hydrophobic residues (F, W, Y, L, I, M, V, or A) as a primary anchor at the C-terminal position of the epitope (see, e.g., Sidney et al., Immunol. Today 17:261, 1996). Exemplary members of the corresponding family of HLA molecules that bind to the B44 supermotif (i.e., the B44 supertype) include at least: B*1801, B*1802, B*3701, B*4001, B*4002, B*4006, B*4402, B*4403, and B*4006.

viii. HLA-B58 Supermotif

The HLA-B58 supermotif is characterized by the presence in peptide ligands of a small aliphatic residue (A, S, or T) as a primary anchor residue at position 2, and an aromatic or hydrophobic residue (F, W, Y, L, I, V, M, or A) as a primary anchor residue at the C-terminal position of the epitope (see, e.g., Sidney and Sette, Immunogenetics, in press, 1999 for reviews of relevant data). Exemplary members of the corresponding family of HLA molecules that bind to the B58 supermotif (i.e., the B58 supertype) include at least: B*1516, B*1517, B*5701, B*5702, and B*5801. Other allele-specific HLA molecules predicted to be members of the B58 supertype are shown in Table 5.

ix. HLA-B62 Supermotif

The HLA-B62 supermotif is characterized by the presence in peptide ligands of the polar aliphatic residue Q or a hydrophobic aliphatic residue (L, V, M, I, or P) as a primary anchor in position 2, and a hydrophobic residue (F, W, Y, M, I, V, L, or A) as a primary anchor at the C-terminal position of the epitope (see, e.g., Sidney and Sette, Immunogenetics, in press, 1999). Exemplary members of the corresponding family of HLA molecules that bind to the B62 supermotif (i.e., the B62 supertype) include at least: B*1501, B*1502, B*1513, and B5201. Other allele-specific HLA molecules predicted to be members of the B62 supertype are shown in Table 5.

x. HLA-A1 Motif

The HLA-A1 motif is characterized by the presence in peptide ligands of T, S, or M as a primary anchor residue at position 2 and the presence of Y as a primary anchor residue at the C-terminal position of the epitope. An alternative allele-specific A1 motif is characterized by a primary anchor residue at position 3 rather than position 2. This motif is characterized by the presence of D, E, A, or S as a primary anchor residue in position 3, and a Y as a primary anchor residue at the C-terminal position of the epitope (see, e.g., DiBrino et al., J. Immunol., 152:620, 1994; Kondo et al., Immunogenetics 45:249, 1997; and Kubo et al., J. Immunol. 152:3913, 1994 for reviews of relevant data).

xi. HLA-A*0201 Motif

An HLA-A2*0201 motif was determined to be characterized by the presence in peptide ligands of L or M as a primary anchor residue in position 2, and L or V as a primary anchor residue at the C-terminal position of a 9-residue peptide (see, e.g., Falk et al., Nature 351:290-296, 1991) and was further found to comprise an I at position 2 and I or A at the C-terminal position of a nine amino acid peptide (see, e.g., Hunt et al., Science 255:1261-1263, Mar. 6, 1992; Parker et al., J. Immunol. 149:3580-3587, 1992). The A*0201 allele-specific motif has also been defined by the present inventors to additionally comprise V, A, T, or Q as a primary anchor residue at position 2, and M or T as a primary anchor residue at the C-terminal position of the epitope (see, e.g., Kast et al., J. Immunol. 152:3904-3912, 1994). Thus, the HLA-A*0201 motif comprises peptide ligands with L, I, V, M, A, T, or Q as primary anchor residues at position 2 and L, I, V, M, A, or T as a primary anchor residue at the C-terminal position of the epitope. The preferred and tolerated residues that characterize the primary anchor positions of the HLA-A*0201 motif are identical to the residues describing the A2 supermotif.

xii. HLA-A3 Motif

The HLA-A3 motif is characterized by the presence in peptide ligands of L, M, V, I, S, A, T, F, C, G, or D as a primary anchor residue at position 2, and the presence of K, Y, R, H, F, or A as a primary anchor residue at the C-terminal position of the epitope (see, e.g., DiBrino et al., *Proc. Natl. Acad. Sci USA* 90:1508,1993; and Kubo et al., *J. Immunol.* 152:3913-3924, 1994).

xiii. HLA-A11 Motif

The HLA-A11 motif is characterized by the presence in peptide ligands of V, T, M, L, I, S, A, G, N, C, D, or F as a primary anchor residue in position 2, and K, R, Y, or H as a primary anchor residue at the C-terminal position of the epitope (see, e.g., Zhang et al., *Proc. Natl. Acad. Sci USA* 90:2217-2221, 1993; and Kubo et al., *J. Immunol.* 152:3913-3924,1994).

xiv. HLA-A24 Motif

The HLA-A24 motif is characterized by the presence in peptide ligands of Y, F, W, or M as a primary anchor residue in position 2, and F, L, I, or W as a primary anchor residue at the C-terminal position of the epitope (see, e.g., Kondo et al., *J. Immunol.* 155:4307-4312, 1995; and Kubo et al., *J. Immunol.* 152:3913-3924, 1994).

5. Assays to Detect T-Cell Responses

Once heteroclitic analogs of the invention are synthesized, they can be tested for the ability to elicit a T-cell response. The preparation and evaluation of motif-bearing peptides such as heteroclitic analogs are described in PCT publications WO 94/20127 and WO 94/03205. Briefly, peptides comprising epitopes from a particular antigen are synthesized and tested for their ability to bind to the appropriate HLA proteins. These assays may involve evaluating the binding of a peptide of the invention to purified HLA Class I molecules in relation to the binding of a radioiodinated reference peptide. Alternatively, cells expressing empty Class I molecules (i.e. lacking peptide therein) may be evaluated for peptide binding by immunofluorescent staining and flow microfluorimetry. Other assays that may be used to evaluate peptide binding include peptide-dependent Class I assembly assays and/or the inhibition of CTL recognition by peptide competition. Those peptides that bind to the Class I molecule, typically with an affinity of 500 nM or less, are further evaluated for their ability to serve as targets for CTLs derived from infected or immunized individuals, as well as for their capacity to induce primary in vitro or in vivo CTL responses that can give rise to CTL populations capable of reacting with selected target cells associated with a disease.

Conventional assays utilized to detect T cell responses include proliferation assays, lymphokine secretion assays, direct cytotoxicity assays, and limiting dilution assays. Such assays are useful in comparing the induction of immune responses by heteroclitic analog peptides to response induced by non-heteroclitic analogs Class I peptides (e.g., from which the heterocloitic analog sequence was based). For example, antigen-presenting cells that have been incubated with a peptide can be assayed for the ability to induce CTL responses in responder cell populations. Antigen-presenting cells can be normal cells such as peripheral blood mononuclear cells or dendritic cells. Alternatively, mutant non-human mammalian cell lines that are deficient in their ability to load Class I molecules with internally processed peptides and that have been transfected with the appropriate human Class I gene, may be used to test for the capacity of the peptide to induce in vitro primary CTL responses.

Peripheral blood mononuclear cells (PBMCs) may be used as the responder cell source of CTL precursors. The appropriate antigen-presenting cells are incubated with peptide, after which the peptide-loaded antigen-presenting cells are then incubated with the responder cell population under optimized culture conditions. Positive CTL activation can be determined by assaying the culture for the presence of CTLs that kill radio-labeled target cells, both specific peptide-pulsed targets as well as target cells expressing endogenously processed forms of the antigen from which the peptide sequence was derived.

Additionally, a method has been devised which allows direct quantification of antigen-specific T cells by staining with Fluorescein-labelled HLA tetrameric complexes (Altman, J. D. et al., *Proc. Natl. Acad. Sci. USA* 90:10330, 1993; Altman, J. D. et al., *Science* 274:94, 1996). Other relatively recent technical developments include staining for intracellular lymphokines, and interferon-γ release assays or Elispot assays. Tetramer staining, intracellular lymphokine staining and Elispot assays all appear to be at least 10-fold more sensitive than more conventional assays (Lalvani, A. et al., *J. Exp. Med.* 186:859, 1997; Dunbar, P. R. et al., *Curr. Biol.* 8:413, 1998; Murali-Krishna, K. et al., *Immunity* 8:177, 1998).

If desired, HTL activation may also be assessed using such techniques known to those in the art such as T cell proliferation and secretion of lymphokines, e.g. IL-2 (see, e.g. Alexander, et al., *Immunity* 1:751-761, 1994).

Alternatively, immunization of HLA transgenic mice can be used to determine immunogenicity of peptide epitopes. Several transgenic mouse models including mice with human A2.1, A11 (which can additionally be used to analyze HLA-A3 epitopes), and B7 alleles have been characterized and others (e.g., transgenic mice for HLA-A1 and A24) are being developed. HLA-DR1 and HLA-DR3 mouse models have also been developed. Additional transgenic mouse models with other HLA alleles may be generated as necessary. The mice may be immunized with peptides emulsified in Incomplete Freund's Adjuvant and the resulting T cells tested for their capacity to recognize peptide-pulsed target cells and target cells transfected with appropriate genes. CTL responses may be analyzed using cytotoxicity assays described above. Similarly, HTL responses may be analyzed using such assays as T cell proliferation or secretion of lymphokines.

Heteroclitic analogs of the invention often induce both Th1 and Th2 cytokine responses. Therefore, one method to compare a heteroclitic candidate with a preselected Class I peptide is to test the induction of Th1 and Th2 cytokines. The preselected Class I peptide will typically be a peptide from which the heteroclitic analog is derived, or if such a peptide does not exist, a Class I peptide with the highest similarity to the candidate. Heteroclitic analogs of the invention typically induce both Th1 and Th2 cytokine responses, but at a level greatly enhanced compared to the Class I peptide from which the analog was derived. For example, a given heteroclitic analog will stimulate an equivalent level of Th1 or Th2 cytokine (50 to 100 pg/ml) at a 10-fold or lower dose compared to the wildtype peptide from which the analog was derived. Additionally, where the Class I peptide induces only, or mainly, either a Th1 or Th2 response, a heteroclitic analog may induce both Th1 and Th2 responses. Th1 cytokines include, e.g., IFNγ, IL-2 and IL-3. Th2 cytokines include, e.g., IL-4, IL-5, IL-6 and IL-10. Production of cytokines can be measured, for example, using ELISA or other immunological quantitation methods. See, e.g., McKinney, et al. *Journal of Immunological Methods* 237:105-117 (2000).

6. Use of Peptide Epitopes as Diagnostic Agents and for Evaluating Immune Responses In one embodiment of the invention, heteroclitic analog peptides as described herein are used as reagents to evaluate an immune response. The immune response to be evaluated is induced by using as an immunogen any agent that may result in the induction of antigen-specific CTLs or HTLs that recognize and bind to the peptide epitope(s) to be employed as the reagent. The peptide reagent need not be used as the immunogen. Assay systems that are used for such an analysis include relatively recent technical developments such as tetramers, staining for intracellular lymphokines and interferon release assays, or Elispot assays.

For example, peptides of the invention are used in tetramer staining assays to assess peripheral blood mononuclear cells for the presence of antigen-specific CTLs following exposure to a tumor cell antigen or an immunogen. The HLA-tetrameric complex is used to directly visualize antigen-specific CTLs (see, e.g., Ogg et al., *Science* 279:2103-2106, 1998; and Altman et al., *Science* 174:94-96, 1996) and determine the frequency of the antigen-specific CTL population in a sample of peripheral blood mononuclear cells. A tetramer reagent using a peptide of the invention is generated as follows: A peptide that binds to an HLA molecule is refolded in the presence of the corresponding HLA heavy chain and $\beta_2$-microglobulin to generate a trimolecular complex. The complex is biotinylated at the carboxyl terminal end of the heavy chain at a site that was previously engineered into the protein. Tetramer formation is then induced by the addition of streptavidin. By means of fluorescently labeled streptavidin, the tetramer can be used to stain antigen-specific cells. The cells can then be identified, for example, by flow cytometry. Such an analysis may be used for diagnostic or prognostic purposes. Cells identified by the procedure can also be used for therapeutic purposes.

Peptides of the invention are also used as reagents to evaluate immune recall responses (see, e.g., Bertoni, et al., *J. Clin. Invest.* 100:503-513, 1997 and Penna, et al., *J. Exp. Med.* 174:1565-1570, 1991). For example, patient PBMC samples from individuals with cancer are analyzed for the presence of antigen-specific CTLs or HTLs using specific peptides. A blood sample containing mononuclear cells can be evaluated by cultivating the PBMCs and stimulating the cells with a peptide of the invention. After an appropriate cultivation period, the expanded cell population can be analyzed, for example, for CTL or for HTL activity.

The peptides are also used as reagents to evaluate the efficacy of a vaccine. PBMCs obtained from a patient vaccinated with an immunogen are analyzed using, for example, either of the methods described above. The patient is HLA typed, and peptide epitope reagents that recognize the allele-specific molecules present in that patient are selected for the analysis. The immunogenicity of the vaccine is indicated by the presence of epitope-specific CTLs and/or HTLs in the PBMC sample.

The peptides of the invention are also used to make antibodies, using techniques well known in the art (see, e.g. CURRENT PROTOCOLS IN IMMUNOLOGY, Wiley/Greene, NY; and *Antibodies A Laboratory Manual*, Harlow and Lane, Cold Spring Harbor Laboratory Press, 1989), which may be useful as reagents to diagnose or monitor cancer. Such antibodies include those that recognize a peptide in the context of an HLA molecule, i.e., antibodies that bind to a peptide-MHC complex.

7. Vaccine Compositions

Vaccines and methods of preparing vaccines that contain an immunogenically effective amount of one or more peptides as described herein are further embodiments of the invention. Once appropriately immunogenic epitopes have been defined, they can be sorted and delivered by various means, herein referred to as "vaccine" compositions. Such vaccine compositions can include, for example, lipopeptides (e.g., Vitiello, A. et al., *J. Clin. Invest.* 95:341, 1995), peptide compositions encapsulated in poly(DL-lactide-co-glycolide) ("PLG") microspheres (see, e.g., Eldridge, et al., *Molec. Immunol.* 28:287-294, 1991: Alonso et al., *Vaccine* 12:299-306, 1994; Jones et al., *Vaccine* 13:675-681, 1995), peptide compositions contained in immune stimulating complexes (ISCOMS) (see, e.g., Takahashi et al., *Nature* 344:873-875, 1990; Hu et al., *Clin Exp Immunol.* 113:235-243, 1998), multiple antigen peptide systems (MAPs) (see e.g., Tam, J. P., *Proc. Natl. Acad. Sci. U.S.A.* 85:5409-5413, 1988; Tam, J. P., *J. Immunol. Methods* 196:17-32, 1996), peptides formulated as multivalent peptides; peptides for use in ballistic delivery systems, typically crystallized peptides, viral delivery vectors (Perkus, M. E. et al., In: *Concepts in vaccine development*, Kaufmann, S. H. E., ed., p. 379, 1996; Chakrabarti, S. et al., *Nature* 320:535, 1986; Hu, S. L. et al., *Nature* 320:537, 1986; Kieny, M.-P. et al., *AIDS Bio/Technology* 4:790, 1986; Top, F. H. et al., *J. Infect. Dis.* 124:148, 1971; Chanda, P. K. et al., *Virology* 175:535, 1990), particles of viral or synthetic origin (e.g., Kofler, N. et al., *J. Immunol. Methods.* 192:25, 1996; Eldridge, J. H. et al., *Sem. Hematol.* 30:16, 1993; Fao, L. D., Jr. et al., *Nature Med.* 7:649, 1995), adjuvants (Warren, H. S., Vogel, F. R., and Chedid, L. A. *Annu. Rev. Immunol.* 4:369, 1986; Gupta, R. K. et al., *Vaccine* 11:293, 1993), liposomes (Reddy, R. et al., *J. Immunol.* 148:1585, 1992; Rock, K. L., *Immunol. Today* 17:131, 1996), or, naked or particle absorbed cDNA (Ulmer, J. B. et al., *Science* 259:1745, 1993; Robinson, H. L., Hunt, L. A., and Webster, R. G., *Vaccine* 11:957, 1993; Shiver, J. W. et al., In: *Concepts in vaccine development*, Kaufmann, S. H. E., ed., p. 423, 1996; Cease, K. B., and Berzofsky, J. A., *Annu. Rev. Immunol.* 12:923, 1994 and Eldridge, J. H. et al., *Sem. Hematol.* 30:16, 1993). Toxin-targeted delivery technologies, also known as receptor mediated targeting, such as those of Avant Immunotherapeutics, Inc. (Needham, Mass.) may also be used.

Vaccines of the invention include nucleic acid-mediated modalities. DNA or RNA encoding one or more of the peptides of the invention can also be administered to a patient. This approach is described, for instance, in Wolff et. al., *Science* 247:1465 (1990) as well as U.S. Pat. Nos. 5,580,859; 5,589,466; 5,804,566; 5,739,118; 5,736,524; 5,679,647; WO 98/04720; and in more detail below. Examples of DNA-based delivery technologies include "naked DNA", facilitated (bupivicaine, polymers, peptide-mediated) delivery, cationic lipid complexes, and particle-mediated ("gene gun") or pressure-mediated delivery (see, e.g., U.S. Pat. No. 5,922,687).

For therapeutic or prophylactic immunization purposes, the peptides of the invention can also be expressed by viral or bacterial vectors. Examples of expression vectors include attenuated viral hosts, such as vaccinia or fowlpox. As an example of this approach, vaccinia virus is used as a vector to express nucleotide sequences that encode the peptides of the invention. Upon introduction into a host bearing a tumor, the recombinant vaccinia virus expresses the immunogenic peptide, and thereby elicits a host CTL and/or HTL response. Vaccinia vectors and methods useful in immunization protocols are described in, e.g., U.S. Pat. No. 4,722,848. Another vector is BCG (Bacille Calmette Guerin). BCG vectors are described in Stover et al., *Nature* 351:456-460 (1991). A wide variety of other vectors useful for therapeutic administration or immunization of the peptides of the invention, e g. adeno and adeno-associated virus vectors, retroviral vectors, *Salmonella typhi* vectors, detoxified anthrax toxin vectors, and the like, will be apparent to those skilled in the art from the description herein.

Furthermore, vaccines in accordance with the invention encompass compositions of one or more of the claimed peptides. A peptide can be present in a vaccine individually. Alternatively, the peptide can exist as a homopolymer comprising multiple copies of the same peptide, or as a heteropolymer of various peptides. Polymers have the advantage of increased immunological reaction and, where different peptide epitopes are used to make up the polymer, the additional ability to induce antibodies and/or CTLs that react with different antigenic determinants of the pathogenic organism or tumor-related peptide targeted for an immune response. The composition can be a naturally occurring region of an antigen or can be prepared, e.g., recombinantly or by chemical synthesis.

Carriers that can be used with vaccines of the invention are well known in the art, and include, e.g., thyroglobulin, albumins such as human serum albumin, tetanus toxoid, polyamino acids such as poly L-lysine, poly L-glutamic acid, influenza, hepatitis B virus core protein, and the like. The vaccines can contain a physiologically tolerable (i.e., acceptable) diluent such as water, or saline, preferably phosphate buffered saline. The vaccines also typically include an adjuvant. Adjuvants such as incomplete Freund's adjuvant, aluminum phosphate, aluminum hydroxide, or alum are examples of materials well known in the art. Additionally, as disclosed herein, CTL responses can be primed by conjugating peptides of the invention to lipids, such as tripalmitoyl-S-glycerylcysteinlyseryl-serine ($P_3CSS$).

Upon immunization with a peptide composition in accordance with the invention, via injection, aerosol, oral, transdermal, transmucosal, intrapleural, intrathecal, or other suitable routes, the immune system of the host responds to the vaccine by producing large amounts of CTLs and/or HTLs specific for the desired antigen. Consequently, the host becomes at least partially immune to later infection, or at least partially resistant to developing an ongoing chronic infection, or derives at least some therapeutic benefit when the antigen was tumor-associated.

In some embodiments, it may be desirable to combine the heteroclitic analog peptides of the invention with components that induce or facilitate neutralizing antibody and or helper T cell responses to the target antigen of interest. A preferred embodiment of such a composition comprises Class I and Class II epitopes in accordance with the invention. An alternative embodiment of such a composition comprises a Class I and/or Class II epitope in accordance with the invention, along with a pan-DR binding peptide such as PADRE™ (Epimmune, San Diego, Calif.) molecule (described, for example, in U.S. Pat. No. 5,736,142).

A vaccine of the invention can also include antigen-presenting cells (APC), such as dendritic cells (DC), as a vehicle to present peptides of the invention. Vaccine compositions can be created in vitro, following dendritic cell mobilization and harvesting, whereby loading of dendritic cells occurs in vitro. For example, dendritic cells are transfected, e.g., with a minigene in accordance with the invention, or are pulsed with peptides. The dendritic cell can then be administered to a patient to elicit immune responses in vivo.

Vaccine compositions, either DNA- or peptide-based, can also be administered in vivo in combination with dendritic cell mobilization whereby loading of dendritic cells occurs in vivo.

Antigenic peptides are used to elicit a CTL and/or HTL response ex vivo, as well. The resulting CTL or HTL cells, can be used to treat tumors in patients that do not respond to other conventional forms of therapy, or will not respond to a therapeutic vaccine peptide or nucleic acid in accordance with the invention. Ex vivo CTL or HTL responses to a particular tumor-associated antigen are induced by incubating in tissue culture the patient's, or genetically compatible, CTL or HTL precursor cells together with a source of antigen-presenting cells, such as dendritic cells, and the appropriate immunogenic peptide. After an appropriate incubation time (typically about 7-28 days), in which the precursor cells are activated and expanded into effector cells, the cells are infused back into the patient, where they will destroy (CTL) or facilitate destruction (HTL) of their specific target cell (an infected cell or a tumor cell). Transfected dendritic cells may also be used as antigen presenting cells.

The vaccine compositions of the invention can also be used in combination with other treatments used for cancer, including use in combination with immune adjuvants such as IL-2, IL-12, GM-CSF, and the like.

Preferably, the following principles are utilized when selecting an array of epitopes for inclusion in a polyepitopic composition for use in a vaccine, or for selecting discrete epitopes to be included in a vaccine and/or to be encoded by nucleic acids such as a minigene. It is preferred that each of the following principles are balanced in order to make the selection. The multiple epitopes to be incorporated in a given vaccine composition may be, but need not be, contiguous in sequence in the native antigen from which the epitopes are derived.

1) Epitopes are selected which, upon administration, mimic immune responses that have been observed to be correlated with tumor clearance. For HLA Class I, this includes 3-4 epitopes that come from at least one tumor-associated antigen (TAA). For HLA Class II, a similar rationale is employed; again 3-4 epitopes are selected from at least one TAA (see e.g., Rosenberg et al., *Science* 278:1447-1450). Epitopes from one TAA may be used in combination with epitopes from one or more additional TAAs to produce a vaccine that targets tumors with varying expression patterns of frequently-expressed TAAs.

2) Epitopes are selected that have the requisite binding affinity established to be correlated with immunogenicity: for HLA Class I an $IC_{50}$ of 500 nM or less, often 200 nM or less; and for Class II an $IC_{50}$ of 1000 nM or less.

3) Sufficient supermotif bearing-peptides, or a sufficient array of allele-specific motif-bearing peptides, are selected to give broad population coverage. For example, it is preferable to have at least 80% population coverage. A Monte Carlo analysis, a statistical evaluation known in the art, can be employed to assess the breadth, or redundancy of, population coverage.

4) When selecting epitopes from cancer-related antigens it is often useful to select analogs because the patient may have developed tolerance to the native epitope. When selecting epitopes for infectious disease-related antigens, it is preferable to select either native or analoged epitopes.

5) Of particular relevance are epitopes referred to as "nested epitopes." Nested epitopes occur where at least two epitopes overlap in a given peptide sequence. A nested peptide sequence can comprise both HLA Class I and HLA Class II epitopes. When providing nested epitopes, a general objective is to provide the greatest number of epitopes per sequence. Thus, an aspect is to avoid providing a peptide that is any longer than the amino terminus of the amino terminal epitope and the carboxyl terminus of the carboxyl terminal epitope in the peptide. When providing a multi-epitopic sequence, such as a sequence comprising nested epitopes, it is generally important to screen the sequence in order to insure that it does not have pathological or other deleterious biological properties.

6) If a polyepitopic protein is created, or when creating a minigene, an objective is to generate the smallest peptide that encompasses the epitopes of interest. This principle is similar, if not the same as that employed when selecting a peptide comprising nested epitopes. However, with an artificial polyepitopic peptide, the size minimization objective is balanced against the need to integrate any spacer sequences between epitopes in the polyepitopic protein. Spacer amino acid residues can, for example, be introduced to avoid junctional epitopes (an epitope recognized by the immune system, not present in the target antigen, and only created by the man-made juxtaposition of epitopes), or to facilitate cleavage between epitopes and thereby enhance epitope presentation. Junctional epitopes are generally to be avoided because the recipient may generate an immune response to that non-native epitope. Of particular concern is a junctional epitope that is a "dominant epitope." A dominant epitope may lead to such a zealous response that immune responses to other epitopes are diminished or suppressed.

8. Minigene Vaccines

A number of different approaches are available which allow simultaneous delivery of multiple epitopes. Nucleic acids encoding the peptides of the invention are a particularly useful embodiment of the invention. Epitopes for inclusion in a minigene are preferably selected according to the guidelines set forth in the previous section. A preferred means of administering nucleic acids encoding the peptides of the invention uses minigene constructs encoding a peptide comprising one or multiple epitopes of the invention.

The use of multi-epitope minigenes is described below and in, e.g., co-pending application U.S. Ser. No. 09/311,784; Ishioka et al., *J. Immunol.* 162:3915-3925, 1999; An, L. and Whitton, J. L., *J. Virol.* 71:2292, 1997; Thomson, S. A. et al., *J. Immunol.* 157:822, 1996; Whitton, J. L. et al., *J. Virol.* 67:348, 1993; Hanke, R. et al., *Vaccine* 16:426, 1998. For example, a multi-epitope DNA plasmid encoding supermotif- and/or motif-bearing epitopes (e.g., PSA, PSM, PAP, and hK2) derived from multiple regions of a TAA, a pan_DR binding peptide such as the PADRE™ universal helper T cell epitope, and an endoplasmic reticulum-translocating signal sequence can be engineered. A vaccine may also comprise epitopes that are derived from other TAAs.

The immunogenicity of a multi-epitopic minigene can be tested in transgenic mice to evaluate the magnitude of CTL induction responses against the epitopes tested. Further, the immunogenicity of DNA-encoded epitopes in vivo can be correlated with the in vitro responses of specific CTL lines against target cells transfected with the DNA plasmid. Thus, these experiments can show that the minigene serves to both: 1.) generate a CTL response and 2.) that the induced CTLs recognized cells expressing the encoded epitopes.

For example, to create a DNA sequence encoding the selected epitopes (minigene) for expression in human cells, the amino acid sequences of the epitopes may be reverse translated. A human codon usage table can be used to guide the codon choice for each amino acid. These epitope-encoding DNA sequences may be directly adjoined, so that when translated, a continuous polypeptide sequence is created. To optimize expression and/or immunogenicity, additional elements can be incorporated into the minigene design. Examples of amino acid sequences that can be reverse translated and included in the minigene sequence include: HLA Class I epitopes, HLA Class II epitopes, a ubiquitination signal sequence, and/or an endoplasmic reticulum targeting signal. In addition, HLA presentation of CTL and HTL epitopes may be improved by including synthetic (e.g. poly-alanine) or naturally-occurring flanking sequences adjacent to the CTL or HTL epitopes; these larger peptides comprising the epitope(s) are within the scope of the invention.

The minigene sequence may be converted to DNA by assembling oligonucleotides that encode the plus and minus strands of the minigene. Overlapping oligonucleotides (30-100 bases long) may be synthesized, phosphorylated, purified and annealed under appropriate conditions using well known techniques. The ends of the oligonucleotides can be joined, for example, using T4 DNA ligase. This synthetic minigene, encoding the epitope eptide, can then be cloned into a desired expression vector.

Standard regulatory sequences well known to those of skill in the art are preferably included in the vector to ensure expression in the target cells. Several vector elements are desirable: a promoter with a down-stream cloning site for minigene insertion; a polyadenylation signal for efficient transcription termination; an *E. coli* origin of replication; and an *E. coli* selectable marker (e.g. ampicillin or kanamycin resistance). Numerous promoters can be used for this purpose, e.g., the human cytomegalovirus (hCMV) promoter. See, e.g., U.S. Pat. Nos. 5,580,859 and 5,589,466 for other suitable promoter sequences.

Additional vector modifications may be desired to optimize minigene expression and immunogenicity. In some cases, introns are required for efficient gene expression, and one or more synthetic or naturally-occurring introns could be incorporated into the transcribed region of the minigene. The inclusion of mRNA stabilization sequences and sequences for replication in mammalian cells may also be considered for increasing minigene expression.

Once an expression vector is selected, the minigene is cloned into the polylinker region downstream of the promoter. This plasmid is transformed into an appropriate *E. coli* strain, and DNA is prepared using standard techniques. The orientation and DNA sequence of the minigene, as well as all other elements included in the vector, are confirmed using restriction mapping and DNA sequence analysis. Bacterial cells harboring the correct plasmid can be stored as a master cell bank and a working cell bank.

In addition, immunostimulatory sequences (ISSs or CpGs) appear to play a role in the immunogenicity of DNA vaccines. These sequences may be included in the vector, outside the minigene coding sequence, if desired to enhance immunogenicity.

In some embodiments, a bi-cistronic expression vector which allows production of both the minigene-encoded epitopes and a second protein (included to enhance or decrease immunogenicity) can be used. Examples of proteins or polypeptides that could beneficially enhance the immune response if co-expressed include cytokines (e.g., IL-2, IL-12, GM-CSF), cytokine-inducing molecules (e.g., LeIF), costimulatory molecules, or for HTL responses, pan-DR binding proteins (e.g., PADRE™, Epimmune, San Diego, Calif.). Helper (HTL) epitopes can be joined to intracellular targeting signals and expressed separately from expressed CTL epitopes; this allows direction of the HTL epitopes to a cell compartment different than that of the CTL epitopes. If required, this could facilitate more efficient entry of HTL epitopes into the HLA Class II pathway, thereby improving HTL induction. In contrast to HTL or CTL induction, specifically decreasing the immune response by co-expression of immunosuppressive molecules (e.g. TGF-β) may be beneficial in certain diseases.

Therapeutic quantities of plasmid DNA can be produced for example, by fermentation in *E. coli*, followed by purification. Aliquots from the working cell bank are used to inoculate growth medium, and grown to saturation in shaker flasks or a bioreactor according to well known techniques. Plasmid DNA can be purified using standard bioseparation technologies such as solid phase anion-exchange resins supplied by QIAGEN, Inc. (Valencia, Calif.). If required, supercoiled DNA can be isolated from the open circular and linear forms using gel electrophoresis or other methods.

Purified plasmid DNA can be prepared for injection using a variety of formulations. The simplest of these is reconstitution of lyophilized DNA in sterile phosphate-buffered saline (PBS). This approach, known as "naked DNA," is currently being used for intramuscular (IM) administration in clinical trials. To maximize the immunotherapeutic effects of minigene DNA vaccines, an alternative method for formulating purified plasmid DNA may be desirable. A variety of methods have been described, and new techniques may become available. Cationic lipids, glycolipids, and fusogenic liposomes can also be used in the formulation (see, e.g., as described by WO 93/24640; Mannino & Gould-Fogerite, *BioTechniques* 6(7): 682 (1988); U.S. Pat. No. 5,279,833; WO 91/06309; and Felgner, et al., *Proc. Nat'l Acad. Sci. USA* 84:7413 (1987). In addition, peptides and compounds referred to collectively as protective, interactive, non-condensing compounds (PINC) could also be complexed to purified plasmid DNA to influence variables such as stability, intramuscular dispersion, or trafficking to specific organs or cell types.

Target cell sensitization can be used as a functional assay for expression and HLA Class I presentation of minigene-encoded CTL epitopes. For example, the plasmid DNA is introduced into a mammalian cell line that is suitable as a target for standard CTL chromium release assays. The transfection method used will be dependent on the final formulation. Electroporation can be used for "naked" DNA, whereas cationic lipids allow direct in vitro transfection. A plasmid expressing green fluorescent protein (GFP) can be co-transfected to allow enrichment of transfected cells using fluorescence activated cell sorting (FACS). These cells are then chromium-51 ($^{51}$Cr) labeled and used as target cells for epitope-specific CTL lines; cytolysis, detected by $^{51}$Cr release, indicates both production of, and HLA presentation of, minigene-encoded CTL epitopes. Expression of HTL epitopes may be evaluated in an analogous manner using assays to assess HTL activity.

In vivo immunogenicity is a second approach for functional testing of minigene DNA formulations. Transgenic mice expressing appropriate human HLA proteins are immunized with the DNA product. The dose and route of administration can be formulation dependent (e.g., IM for DNA in PBS, intraperitoneal (IP) for lipid-complexed DNA). Twenty-one days after immunization, splenocytes are harvested and restimulated for one week in the presence of peptides encoding each epitope being tested. Thereafter, for CTL effector cells, assays are conducted for cytolysis of peptide-loaded, $^{51}$Cr-labeled target cells using standard techniques. Lysis of target cells that were sensitized by HLA loaded with peptide epitopes, corresponding to minigene-encoded epitopes, demonstrates DNA vaccine function for in vivo induction of CTLs. Immunogenicity of HTL epitopes is evaluated in transgenic mice in an analogous manner.

Alternatively, the nucleic acids can be administered intradermally, e.g. by injection or ballistic delivery as described, for instance, in U.S. Pat. No. 5,204,253. Using this technique, particles comprised solely of DNA are administered. In a further alternative embodiment, DNA can be adhered to particles, such as gold particles.

Minigenes can also be delivered using other bacterial or viral delivery systems well known in the art, e.g., an expression construct encoding epitopes of the invention can be incorporated into a viral vector such as vaccinia.

9. Combinations of CTL Peptides with Helper Peptides

Vaccine compositions comprising the peptides of the present invention can be modified to provide desired attributes, such as improved serum half-life, or to enhance immunogenicity.

For instance, the ability of a peptide to induce CTL activity can be enhanced by linking the peptide to a sequence which contains at least one epitope that is capable of inducing a T helper cell response. The use of T helper epitopes in conjunction with CTL epitopes to enhance immunogenicity is illustrated, for example, in the co-pending applications U.S. Ser. No. 08/820,360, U.S. Ser. No. 08/197,484, and U.S. Ser. No. 08/464,234.

Although a CTL peptide can be directly linked to a T helper peptide, often CTL epitope/HTL epitope conjugates are linked by a spacer molecule. The spacer is typically comprised of relatively small, neutral molecules, such as amino acids or amino acid mimetics, which are substantially uncharged under physiological conditions. The spacers are typically selected from, e.g., Ala, Gly, or other neutral spacers of nonpolar amino acids or neutral polar amino acids. It will be understood that the optionally present spacer need not be comprised of the same residues and thus may be a hetero- or homo-oligomer. When present, the spacer will usually be at least one or two residues, more usually three to six residues and sometimes 10 or more residues. The CTL peptide epitope can be linked to the T helper peptide epitope either directly or via a spacer either at the amino or carboxy terminus of the CTL peptide. The amino terminus of either the immunogenic peptide or the T helper peptide may be acylated.

In certain embodiments, the T helper peptide is one that is recognized by T helper cells present in the majority of the population. This can be accomplished by selecting amino acid sequences that bind to many, most, or all of the HLA Class II molecules. These are known as "loosely HLA-restricted" or "promiscuous" T helper sequences. Examples of peptides that are promiscuous include sequences from antigens such as tetanus toxoid at positions 830-843 (QYIKAN-SKFIGITE) (SEQ ID NO:32), *Plasmodium falciparum* circumsporozoite (CS) protein at positions 378-398 (DIEKKIAKMEKASSVFNVVNS) (SEQ ID NO:33), and *Streptococcus* 18 kD protein at positions 116 (GAVDSILG- GVATYGAA) (SEQ ID NO:34). Other examples include peptides bearing a DR 1-4-7 supermotif, or either of the DR3 motifs.

Alternatively, it is possible to prepare synthetic peptides capable of stimulating T helper lymphocytes, in a loosely HLA-restricted fashion, using amino acid sequences not found in nature (see, e.g., PCT publication WO 95/07707). These synthetic compounds called Pan-DR-binding epitopes (e.g., PADRE™, Epimmune, Inc., San Diego, Calif.) are designed to most preferably bind most HLA-DR (human HLA Class II) molecules. For instance, a pan-DR-binding epitope peptide having the formula: aKXVAAWTLKAAa, where "X" is either cyclohexylalanine (SEQ ID NO: 35), phenylalanine (SEQ ID NO:36), or tyrosine (SEQ ID NO:37), and "a" is either D-alanine or L-alanine, has been found to bind to most HLA-DR alleles, and to stimulate the response of T helper lymphocytes from most individuals, regardless of their HLA type. An alternative of a pan-DR binding epitope comprises all "L" natural amino acids and can be provided in the form of nucleic acids that encode the epitope.

HTL peptide epitopes can also be modified to alter their biological properties. For example, they can be modified to include D-amino acids to increase their resistance to proteases and thus extend their serum half life, or they can be conjugated to other molecules such as lipids, proteins, carbohydrates, and the like to increase their biological activity. For example, a T helper peptide can be conjugated to one or more palmitic acid chains at either the amino or carboxyl termini.

10. Combinations of CTL Peptides with T Cell Priming Agents

In some embodiments it may be desirable to include in the pharmaceutical compositions of the invention at least one component which primes cytotoxic T lymphocytes. Lipids have been identified as agents capable of priming CTL in vivo against viral antigens. For example, palmitic acid residues can be attached to the $\epsilon$- and $\alpha$-amino groups of a lysine residue and then linked, e.g., via one or more linking residues such as Gly, Gly-Gly-, Ser, Ser-Ser, or the like, to an immunogenic peptide. The lipidated peptide can then be administered either directly in a micelle or particle, incorporated into a liposome, or emulsified in an adjuvant, e.g., incomplete Freund's adjuvant. A preferred immunogenic composition comprises palmitic acid attached to $\epsilon$- and $\alpha$-amino groups of Lys, which is attached via linkage, e.g., Ser-Ser, to the amino terminus of the immunogenic peptide.

As another example of lipid priming of CTL responses, $E.$ $coli$ lipoproteins, such as tripalmitoyl-S-glycerylcysteinly-seryl-serine ($P_3CSS$) can be used to prime virus specific CTL when covalently attached to an appropriate peptide (see, e.g., Deres, et al., Nature 342:561, 1989). Peptides of the invention can be coupled to $P_3CSS$, for example, and the lipopeptide administered to an individual to specifically prime a CTL response to the target antigen. Moreover, because the induction of neutralizing antibodies can also be primed with $P_3CSS$-conjugated epitopes, two such compositions can be combined to more effectively elicit both humoral and cell-mediated responses.

CTL and/or HTL peptides can also be modified by the addition of amino acids to the termini of a peptide to provide for ease of linking peptides one to another, for coupling to a carrier support or larger peptide, for modifying the physical or chemical properties of the peptide or oligopeptide, or the like. Amino acids such as tyrosine, cysteine, lysine, glutamic or aspartic acid, or the like, can be introduced at the C- or N-terminus of the peptide or oligopeptide, particularly Class I peptides. However, it is to be noted that modification at the carboxyl terminus of a CTL epitope may, in some cases, alter binding characteristics of the peptide. In addition, the peptide or oligopeptide sequences can differ from the natural sequence by being modified by terminal-$NH_2$ acylation, e.g., by alkanoyl ($C_1$-$C_{20}$) or thioglycolyl acetylation, terminal-carboxyl amidation, e.g., ammonia, methylamine, etc. In some instances these modifications may provide sites for linking to a support or other molecule.

11. Vaccine Compositions Comprising DC Pulsed with CTL and/or HTL Peptides

An embodiment of a vaccine composition in accordance with the invention comprises ex vivo administration of a cocktail of epitope-bearing peptides to PBMC, or isolated DC therefrom, from the patient's blood. A pharmaceutical to facilitate harvesting of DC can be used, such as Progenipoietin™ (Monsanto, St. Louis, Mo.) or GM-CSF/IL-4. After pulsing the DC with peptides and prior to reinfusion into patients, the DC are washed to remove unbound peptides. In this embodiment, a vaccine comprises peptide-pulsed DCs that present the pulsed peptide epitopes complexed with HLA molecules on their surfaces.

The DC can be pulsed ex vivo with a cocktail of peptides, some of which stimulate CTL response to one or more antigens of interest. Optionally, a helper T cell peptide such as a PADRE™ family molecule, can be included to facilitate the CTL response.

12. Administration of Vaccines for Therapeutic or Prophylactic Purposes

The peptides of the present invention and pharmaceutical and vaccine compositions of the invention are typically used therapeutically to treat cancer. Vaccine compositions containing the peptides of the invention are typically administered to a cancer patient who has a malignancy associated with expression of one or more antigens. Alternatively, vaccine compositions can be administered to an individual susceptible to, or otherwise at risk for developing cancer.

In therapeutic applications, peptide and/or nucleic acid compositions are administered to a patient in an amount sufficient to elicit an effective CTL and/or HTL response to the tumor antigen and to cure or at least partially arrest or slow symptoms and/or complications. An amount adequate to accomplish this is defined as "therapeutically effective dose." Amounts effective for this use will depend on, e.g., the particular composition administered, the manner of administration, the stage and severity of the disease being treated, the weight and general state of health of the patient, and the judgment of the prescribing physician.

As noted above, peptides comprising CTL and/or HTL epitopes of the invention induce immune responses when presented by HLA molecules and contacted with a CTL or HTL specific for an epitope comprised by the peptide. The peptides (or DNA encoding them) can be administered individually or as fusions of one or more peptide sequences. The manner in which the peptide is contacted with the CTL or HTL is not critical to the invention. For instance, the peptide can be contacted with the CTL or HTL either in vivo or in vitro. If the contacting occurs in vivo, the peptide itself can be administered to the patient, or other vehicles, e.g., DNA vectors encoding one or more peptides, viral vectors encoding the peptide(s), liposomes and the like, can be used, as described herein.

When the peptide is contacted in vitro, the vaccinating agent can comprise a population of cells, e.g., peptide-pulsed dendritic cells, or TAA-specific CTLs, which have been induced by pulsing antigen-presenting cells in vitro with the peptide or by transfecting antigen-presenting cells with a minigene of the invention. Such a cell population is subsequently administered to a patient in a therapeutically effective dose.

For therapeutic use, administration should generally begin at the first diagnosis of cancer. This is followed by boosting doses until at least symptoms are substantially abated and for a period thereafter. The embodiment of the vaccine composition (i.e., including, but not limited to embodiments such as peptide cocktails, polyepitopic polypeptides, minigenes, or TAA-specific CTLs or pulsed dendritic cells) delivered to the patient may vary according to the stage of the disease or the patient's health status. For example, a vaccine comprising TAA-specific CTLs may be more efficacious in killing tumor cells in patients with advanced disease than alternative embodiments.

The vaccine compositions of the invention may also be used therapeutically in combination with treatments such as surgery. An example is a situation in which a patient has undergone surgery to remove a primary tumor and the vaccine is then used to slow or prevent recurrence and/or metastasis.

Where susceptible individuals, e.g., individuals who may be diagnosed as being genetically pre-disposed to developing a prostate tumor, are identified prior to diagnosis of cancer, the composition can be targeted to them, thus minimizing the need for administration to a larger population.

The dosage for an initial therapeutic immunization generally occurs in a unit dosage range where the lower value is about 1, 5, 50, 500, or 1,000 µg and the higher value is about 10,000; 20,000; 30,000; or 50,000 µg. Dosage values for a human typically range from about 500 µg to about 50,000 µg per 70 kilogram patient. Initial doses followed by boosting doses at established intervals, e.g., from four weeks to six months, may be required, possibly for a prolonged period of time to effectively treat a patient. Boosting dosages of between about 1.0 µg to about 50,000 µg of peptide pursuant to a boosting regimen over weeks to months may be administered depending upon the patient's response and condition as determined by measuring the specific activity of CTL and HTL obtained from the patient's blood.

Administration should continue until at least clinical symptoms or laboratory tests indicate that the tumor has been eliminated or that the tumor cell burden has been substantially reduced and for a period thereafter. The dosages, routes of administration, and dose schedules are adjusted in accordance with methodologies known in the art.

In certain embodiments, peptides and compositions of the present invention are employed in serious disease states, that is, life-threatening or potentially life threatening situations. In such cases, as a result of the minimal amounts of extraneous substances and the relative nontoxic nature of the peptides in preferred compositions of the invention, it is possible and may be felt desirable by the treating physician to administer substantial excesses of these peptide compositions relative to these stated dosage amounts.

The vaccine compositions of the invention can also be used as prophylactic agents. For example, the compositions can be administered to individuals at risk of developing prostate cancer. Generally the dosage for an initial prophylactic immunization generally occurs in a unit dosage range where the lower value is about 1, 5, 50, 500, or 1000 µg and the higher value is about 10,000; 20,000; 30,000; or 50,000 µg. Dosage values for a human typically range from about 500 µg to about 50,000 µg per 70 kilogram patient. This is followed by boosting dosages of between about 1.0 µg to about 50,000 µg of peptide administered at defined intervals from about four weeks to six months after the initial administration of vaccine. The immunogenicity of the vaccine may be assessed by measuring the specific activity of CTL and HTL obtained from a sample of the patient's blood.

The pharmaceutical compositions for therapeutic treatment are intended for parenteral, topical, oral, intrathecal, or local administration. Preferably, the pharmaceutical compositions are administered parentally, e.g., intravenously, subcutaneously, intradermally, or intramuscularly. Thus, the invention provides compositions for parenteral administration which comprise a solution of the immunogenic peptides dissolved or suspended in an acceptable carrier, preferably an aqueous carrier. A variety of aqueous carriers may be used, e.g., water, buffered water, 0.8% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH-adjusting and buffering agents, tonicity adjusting agents, wetting agents, preservatives, and the like, for example, sodium acetate, sodium lactate, sodium chloride, potassium chloride, calcium chloride, sorbitan monolaurate, triethanolamine oleate, etc.

The concentration of peptides of the invention in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

A human unit dose form of the peptide composition is typically included in a pharmaceutical composition that comprises a human unit dose of an acceptable carrier, preferably an aqueous carrier, and is administered in a volume of fluid that is known by those of skill in the art to be used for administration of such compositions to humans (see, e.g., Remington's Pharmaceutical Sciences, 17$^{th}$ Edition, A. Gennaro, Editor, Mack Publishing Co., Easton, Pa., 1985).

The peptides of the invention may also be administered via liposomes, which serve to target the peptides to a particular tissue, such as lymphoid tissue, or to target selectively to infected cells, as well as to increase the half-life of the peptide composition. Liposomes include emulsions, foams, micelles, insoluble monolayers, liquid crystals, phospholipid dispersions, lamellar layers and the like. In these preparations, the peptide to be delivered is incorporated as part of a liposome, alone or in conjunction with a molecule which binds to a receptor prevalent among lymphoid cells, such as monoclonal antibodies which bind to the CD45 antigen, or with other therapeutic or immunogenic compositions. Thus, liposomes either filled or decorated with a desired peptide of the invention can be directed to the site of lymphoid cells, where the liposomes then deliver the peptide compositions. Liposomes for use in accordance with the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka, et al., *Ann. Rev. Biophys. Bioeng.* 9:467 (1980), and U.S. Pat. Nos. 4,235,871, 4,501,728, 4,837,028, and 5,019,369.

For targeting cells of the immune system, a ligand to be incorporated into the liposome can include, e.g., antibodies or fragments thereof specific for cell surface determinants of the desired immune system cells. A liposome suspension containing a peptide may be administered intravenously, locally, topically, etc., in a dose which varies according to, inter alia, the manner of administration, the peptide being delivered, and the stage of the disease being treated.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient, that is, one or more peptides of the invention, and more preferably at a concentration of 25%-75%.

For aerosol administration, the immunogenic peptides are preferably supplied in finely divided form along with a surfactant and propellant. Typical percentages of peptides are 0.01%-20% by weight, preferably 1%-10%. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%-20% by weight of the composition, preferably 0.25-5%. The balance of the composition is ordinarily propellant. A carrier can also be included, as desired, as with, e.g., lecithin for intranasal delivery.

13. Kits

The peptide and nucleic acid compositions of this invention can be provided in kit form together with instructions for vaccine administration. Typically the kit would include desired peptide compositions in a container, preferably in unit dosage form and instructions for administration. An alternative kit would include a minigene construct with desired nucleic acids of the invention in a container, preferably in unit dosage form together with instructions for administration. Lymphokines such as IL-2 or IL-12 may also be included in the kit. Other kit components that may also be desirable include, for example, a sterile syringe, booster dosages, and other desired excipients.

Epitopes in accordance with the present invention were successfully used to induce an immune response. Immune responses with these epitopes have been induced by administering the epitopes in various forms. The epitopes have been administered as peptides, as nucleic acids, and as viral vectors comprising nucleic acids that encode the epitope(s) of the invention. Upon administration of peptide-based epitope forms, immune responses have been induced by direct loading of an epitope onto an empty HLA molecule that is expressed on a cell, and via internalization of the epitope and processing via the HLA Class I pathway; in either event, the HLA molecule expressing the epitope was then able to interact with and induce a CTL response. Peptides can be delivered directly or using such agents as liposomes. They can additionally be delivered using ballistic delivery, in which the peptides are typically in a crystalline form. When DNA is used to induce an immune response, it is administered either as naked DNA, generally in a dose range of approximately 1-5 mg, or via the ballistic "gene gun" delivery, typically in a dose range of approximately 10-100 μg. The DNA can be delivered in a variety of conformations, e.g., linear, circular etc. Various viral vectors have also successfully been used that comprise nucleic acids which encode epitopes in accordance with the invention.

Accordingly compositions in accordance with the invention exist in several forms. Embodiments of each of these composition forms in accordance with the invention have been successfully used to induce an immune response.

One composition in accordance with the invention comprises a plurality of peptides. This plurality or cocktail of peptides is generally admixed with one or more pharmaceutically acceptable excipients. The peptide cocktail can comprise multiple copies of the same peptide or can comprise a mixture of peptides. The peptides can be analogs of naturally occurring epitopes. The peptides can comprise artificial amino acids and/or chemical modifications such as addition of a surface active molecule, e.g., lipidation; acetylation, glycosylation, biotinylation, phosphorylation etc. The peptides can be CTL or HTL epitopes. In a preferred embodiment the peptide cocktail comprises a plurality of different CTL epitopes and at least one HTL epitope. The HTL epitope can be naturally or non-naturally (e.g., PADRE®, Epimmune Inc., San Diego, Calif.). The number of distinct epitopes in an embodiment of the invention is generally a whole unit integer from one through one hundred fifty (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, . . . , 150).

An additional embodiment of a composition in accordance with the invention comprises a polypeptide multi-epitope construct, i.e., a polyepitopic peptide. Polyepitopic peptides in accordance with the invention are prepared by use of technologies well-known in the art. By use of these known technologies, epitopes in accordance with the invention are connected one to another. The polyepitopic peptides can be linear or non-linear, e.g., multivalent. These polyepitopic constructs can comprise artificial amino acids, spacing or spacer amino acids, flanking amino acids, or chemical modifications between adjacent epitope units. The polyepitopic construct can be a heteropolymer or a homopolymer. The polyepitopic constructs generally comprise epitopes in a quantity of any whole unit integer between 2-150 (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, . . . , 150). The polyepitopic construct can comprise CTL and/or HTL epitopes. One or more of the epitopes in the construct can be modified, e.g., by addition of a surface active material, e.g. a lipid, or chemically modified, e.g., acetylation, etc. Moreover, bonds in the multiepitopic construct can be other than peptide bonds, e.g., covalent bonds, ester or ether bonds, disulfide bonds, hydrogen bonds, ionic bonds, etc.

Alternatively, a composition in accordance with the invention comprises construct which comprises a series, sequence, stretch, etc., of amino acids that have homology to (i.e., corresponds to or is contiguous with) to a native sequence.

This stretch of amino acids comprises at least one subsequence of amino acids that, if cleaved or isolated from the longer series of amino acids, functions as an HLA Class I or HLA Class II epitope in accordance with the invention. In this embodiment, the peptide sequence is modified, so as to become a construct as defined herein, by use of any number of techniques known or to be provided in the art. The polyepitopic constructs can contain homology to a native sequence in any whole unit integer increment from 70-100% (e.g., 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or, 100 percent).

A further embodiment of a composition in accordance with the invention is an antigen presenting cell that comprises one or more epitopes in accordance with the invention. The antigen presenting cell can be a "professional" antigen presenting cell, such as a dendritic cell. The antigen presenting cell can comprise the epitope of the invention by any means known or to be determined in the art. Such means include pulsing of dendritic cells with one or more individual epitopes or with one or more peptides that comprise multiple epitopes, by nucleic acid administration such as ballistic nucleic acid delivery or by other techniques in the art for administration of nucleic acids, including vector-based, e.g. viral vector, delivery of nucleic acids.

Further embodiments of compositions in accordance with the invention comprise nucleic acids that encode one or more peptides of the invention, or nucleic acids which encode a polyepitopic peptide in accordance with the invention. As appreciated by one of ordinary skill in the art, various nucleic acids compositions will encode the same peptide due to the redundancy of the genetic code. Each of these nucleic acid compositions falls within the scope of the present invention. This embodiment of the invention comprises DNA or RNA, and in certain embodiments a combination of DNA and RNA. It is to be appreciated that any composition comprising nucleic acids that will encode a peptide in accordance with the invention or any other peptide based composition in accordance with the invention, falls within the scope of this invention.

EXAMPLES

Preparation A

Peptide Synthesis and Generation of Peptide Analogs

The peptides used in these examples are shown in Table 1. All of the wildtype human CTL epitopes derived from tumor-associated antigens, as well as the wildtype viral epitopes derived from the polymerase genes of the HIV and hepatitis B virus (HBV[2]), have shown immunogenicity in human and transgenic mouse systems (Kawashima, I., et al., *Human Immunol.* (1998) 59:1; Ishioka, G., et al., *J. Immunol.* (1999) 162:3915; Epimmune, unpublished data).

Peptides that were tested initially for heteroclitic activity were synthesized by Chiron Technologies (Victor, Australia). Peptides requiring further biological characterization were synthesized at Epimmune using conventional methods (Ruppert, J., et al., *Cell* (1993) 74:929) and their purity was routinely >95%, as determined by analytical reverse-phase HPLC. The identity of the latter peptides was confirmed by mass spectral analysis.

Preparation B

Scheme for Selection of Single Amino Acid Substitutions

Table 2 shows the similarity assignments between any given amino acid pair so that a given amino acid substitution could be characterized as being a conservative, semi-conservative, or non-conservative substitution.

The degree of similarity between amino acid pairs was quantified by averaging, for each amino acid pair, the rank coefficient scores for PAM250, hydrophobicity, and side chain volume as described below. Based on the average values of these composite rankings, the table shows each pair to be conserved, semi-conserved or non-conserved.

The Dayhoff PAM250 score (Dayhoff, M. O., et al., *Atlas of Protein Sequence and Structure*, Vol. 5, suppl.3. (1978) M. O. Dayhoff, ed. National Biomedical Research Foundation, Washington D.C., p. 345; Creighton, T. E., *Proteins: structures and molecular properties* (1993) (2nd edition) W. H. Freeman and Company, NY; http://prowl.rockefeller.edu/aainfo/pam250.html) is a commonly utilized protein alignment scoring matrix which measures the percentage of acceptable point mutations (PAM) within a defined time frame. The frequencies of these mutations are different from what would be expected from the probability of random mutations, and presumably reflect a bias due to the degree of physical and chemical similarity of the amino acid pair involved in the substitution. To obtain a score of amino acid similarity that could be standardized with other measures of similarity, the PAM250 scores were converted to a rank value, where 1 indicates the highest probability of being an accepted mutation.

The most commonly utilized scales to represent the relative hydrophobicity of the 20 naturally occurring amino acids (Cornette, J., et al., *J. Mol. Biol.* (1987) 195:659) are those developed on the basis of experimental data by Kyte and Doolittle (Kyte, J. and R. F. Doolittle, *J. Mol. Biol.* (1982) 157:105), and by Fauchere and Pliska (Fauchere, J. and V. Pliska, *Eur. J. Med. Chem.* (1983) 18:369). The Kyte/Doolittle scale measures the $H_2O$/organic solvent partition of individual amino acids. Because it considers the position of amino acids in folded proteins, it may most accurately reflect native hydrophobicity in the context of proteins. The Fauchere/Pliska scale measures the octanol/$H_2O$ partitioning of N-acetyl amino acid amides, and most accurately reflects hydrophobicity in the context of denatured proteins and/or small synthetic peptides. To obtain scores for hydrophobicity, each amino acid residue was ranked on both the Kyte/Doolittle and Fauchere/Pliska hydrophobicity scales. An average rank between the two scales was calculated and the average difference in hydrophobicity for each pair was calculated.

Finally, for calculating amino acid side-chain volume, the partial volume in solution obtained by noting the increase in volume of water after adding either one molecule or one gram of amino acid residue was considered (Zamyatnin, A. A., *Ann. Rev. Biophys. Bioeng.* (1984) 13:145; Zamyatnin, A. A., *Prog. Biophys. Mol. Biol.* (1972) 24:107). The absolute difference in the partial volume of each possible pairing of the 20 naturally occurring amino acids was calculated and ranked, where 1 indicated residues with the most similar volumes, and 20 the most dissimilar.

Preparation C

Materials for Assays

1. APC Lines

Cell lines that present peptides in the context of HLA-A2.1 were prepared as follows:

The .221A2.1 cell line was generated by transfecting the HLA-A2.1 gene into the HLA-A, -B, -C-null mutant EBVtransformed human B-lymphoblastoid cell line 3A4-721.221 (Kawashima, I., et al., *Human Immunol.* (1998) 59:1). The cell line GM3107 was used as APCs to measure B7 CTL responses.

Tumor cell lines were prepared by transfection of Meth A cells, a methylcholanthrene-induced sarcoma, and the Jurkat cell line with the HLA-A2.1 or HLA-A2.1/$K^b$ transgene transfection was performed using methods described elsewhere (Vitiello, A., et al., *J. Exp. Med.* (1991) 173:1007). A combination of the HLA-typed melanoma cell lines 624mel (A2.1$^+$, MAGE$^+$) and 888mel (A2.1$^-$, MAGE$^-$), were kindly provided by Y. Kawakami and S. Rosenberg (National Cancer Institute), and were used to measure presentation of endogenously processed MAGE3 epitopes (Boon, T., et al., *Ann. Rev. Immunol.* (1994) 12:337). The melanoma cell lines were treated with 100 IU/ml human IFNγ (Genzyme, Cambridge, Mass.) for 48 h at 37° C. before using as APC.

All cells in this study were grown in RPMI-1640 medium supplemented with antibiotics, sodium pyruvate, nonessential amino acids, and 10% (v/v) heat-inactivated FBS.

2. In Vitro Induction of CTL from Human PBMC and Derivation of Human CTL Lines To generate peptide-specific CTL lines against the MAGE3.112, MAGE2.170, and a carcinoembryonic antigen (CEA) epitope, CEA.691, PBMC from normal subjects were stimulated repeatedly in vitro with peptide as described (Kawashima, I., et al., *Human Immunol.* (1998) 59:1). Briefly, peptide-pulsed dendritic cells (differentiated from adherent PBMC by culturing in GM-CSF and IL4) were co-cultured with autologous CD8$^+$ T cells, obtained by positive selection with antibody-coated beads (Dynal A. S., Oslo, Norway or Miltenyi Biotec, Auburn, Calif.) in a 48-well plate. After 7 days of culture in the presence of IL2, IL7, and IL10, each PBMC culture (well) was restimulated in vitro with adherent PBMC pulsed with peptide. Cultures were then tested for CTL activity by measuring IFNγ production after stimulation with .221A2.1 tumor APC (A2 epitopes) or GM3107 tumor cells (B7 epitopes), in the presence or absence of peptide. CTL lines were expanded from PBMC cultures demonstrating peptide-specific IFNγ responses by additional in vitro stimulation with adherent peptide-pulsed PBMC.

3. Murine CTL Lines

CTL lines against epitopes HBV Pol.455 and HIV Pol.476 peptides were generated in HLA-A2.1/$K^{bxs}$ transgenic mice by DNA immunization as described elsewhere (Ishioka, G., et al., *J. Immunol.* (1999) 162:3915). HLA-A2.1/$K^{bxs}$ and HLA-A2.1/$K^{bxd}$ transgenic mice were bred at Epimmune. These strains represent the F1 generation of a cross between an HLA-A2.1/$K^b$ transgenic strain generated on the C57BL/6 background (Vitiello, A., et al., *J. Exp. Med.* (1991) 173: 1007), and SJL or BALB/c mice (Jackson Laboratories, Bar Harbor, Me.), respectively. A CTL line against the MAGE2.157 epitope was generated by immunizing 8-12 wk old HLA-A2.1/$K^{bxs}$ mice s.c. at the tail base with 50 μg of peptide and 140 μg of the HBV Core.128 Th epitope, TPPAYRPPNAPIL (SEQ ID NO:30), emulsified in IFA and restimulating primed splenocytes repeatedly in vitro with peptide.

Preparation D

Assay Methods

1. Measurement of Peptide Binding Affinity for HLA-A2.1 or HLA-B7 Molecules Binding of test peptides to HLA-A2.1 was measured by determining the level of competition induced by a given test peptide for binding of a radiolabeled standard peptide to HLA-A2.1. The percentage of MHC-bound radioactivity was determined by gel filtration and the concentration of test peptide that inhibited 50% of the binding of the labeled standard peptide ($IC_{50}$) was calculated (Ruppert, J., et al., *Cell* (1993) 74:929; Sette, A., et al., *Mol. Immunol.* (1994) 31:813). The standard peptide was the HBV Core.18 epitope (sequence FLPSDFFPSV) (SEQ ID NO:31). A similar assay was performed to determine the binding affinity of peptides to purified HLA-B7 (B*0702) molecules. In the latter assay, the radiolabeled standard peptide was the SS 5-13a ($L_7 \rightarrow Y$) peptide (sequence APRTLVYLL) (SEQ ID NO:39).

2. Measurement of Murine and Human IFNγ, IL5, and IL10 Production by CTL

An in situ capture ELISA was used for measuring IFNγ release from CTL (McKinney, D., et al., *J. Immunol. Methods* (2000) 237:105). Briefly, CTL were stimulated with APC and peptide in ELISA-grade 96-well flat bottom wells that were precoated with either an anti-mouse IFNγ (clone R4-6A2, Pharmingen, San Diego, Calif.) or anti-human IFNγ mAb (clone NIB42, Pharmingen). After culturing cells, wells are washed and developed by adding a biotinylated anti-mouse IFNγ (clone XMG1.2, Pharmingen) or anti-human IFNγ (clone 4S.B3, Pharmingen) mAb followed by enzyme-conjugated streptavidin (Zymed, South San Francisco, Calif.) and 3, 3', 5, 5' tetramethylbenzidine substrate (ImmunoPure TMB substrate kit, Pierce, Rockford, Ill.). The absorbance of each well was measured at 450 nm on a Labsystems Multiskan RC ELISA plate reader. The level of IFNγ produced in each well was determined by extrapolation from a mouse or human IFNγ standard curve established in the same assay.

Murine and human IL5 and IL10 were measured in culture supernates using ELISA kits (R&D Biosystems, Minneapolis, Minn.). These assays, employing the quantitative sandwich ELISA technique, were performed according to the manufacturer's protocol.

3. Enzyme-liked Immunospot (Elispot) Assay for Measuring ex vivo CTL Responses Elispot assays were performed according to standard protocols (Murali-Krishna, K., et al., *Immunity* (1998) 8:177; Lewis, J. J., et al., *Int. J. Cancer* (2000) 87:391). Briefly, flat bottom 96-well nitrocellulose plates (Immobilon-P membrane, Millipore, Bedford, Mass.) were coated with anti-IFNγ mAb (10 μg/ml, clone R4-6A2) and incubated overnight at 4° C. After washing with PBS, plates were blocked with RPMI medium containing 10% FBS for 1 h at 37° C. Four×10$^5$ splenic CD8$^+$ cells isolated by magnetic beads (Miltenyi, Auburn, Calif.) and 5×10$^4$ Jurkat-A2.1/$K^b$ cells pulsed with 10 μg/ml of peptide were added to each well and cells were incubated for 20 h in RPMI medium containing 10% FBS. After incubation, the plates were washed thoroughly with PBS/0.05% Tween and biotinylated anti-IFNγ mAb (2 μg/ml, clone XMG1.2) was added to each well and plates were incubated for 4 h at 37° C. Plates were then washed four times with PBS (containing 0.1% Tween-20) and Vectastain ABC peroxidase (Vectastain Elite kit; Vector Laboratories, Burlingame, Calif.). After incubating for 1 h at room temperature, plates were washed three times with 1×PBS/0.05% Tween followed by three additional washes with 1×PBS. One hundred μl of AEC solution (Sigma Chemical, St. Louis, Mo.) was added to develop the spots. The reaction was stopped after 4-6 min under running tap water. The spots were counted by computer-assisted image analysis (Zeiss KS Elispot Reader, Jena, Germany). The net number of spots/$10^6$ CD8+ cells was calculated as follows: [(number of spots against relevant peptide)−(number of spots against irrelevant control peptide)]×2.5.

Example 1

Screening of Peptide Analogs for Heteroclitic Activity

A. Identification of CEA.691 and MAGE3.112 Analogs Associated with Increased IFNγ Release Prior to screening analogs, a peptide dose titration of IFNγ production from CTL lines was performed over a wide range of doses of wildtype peptide. .221A2.1 tumor cells were pulsed with varying doses of peptide then $10^5$ peptide-loaded cells were cultured with an equivalent number of murine or human CTL. After 24 hr (murine) or 48 hr (human) incubation at 37° C., levels of IFNγ released by CTL were measured by the in situ capture ELISA assay. After determining a dose titration curve, a suboptimal peptide dose where activity against wildtype peptide was barely detectable was selected for screening the antigenicity of a panel of peptide analogs. For all of the murine and human CTL lines, this suboptimal dose ranged from 0.1-1 µg/ml. It should be noted that although murine CTL lines were generated in HLA-A2.1/$K^{bxs}$ transgenic mice which express an HLA molecule with murine H-2 $K^b$ sequences in the third domain, all responded to peptide presented on APC expressing the native HLA-A2.1 molecule.

For screening of peptide analogs, .221A2.1 cells were pulsed with each analog at the selected suboptimal dose and peptide-loaded APC were cultured with CTL as described above. Analogs inducing enhanced CTL responses relative to wildtype peptide were then selected for further characterization. These analogs were characterized by performing a peptide dose titration side-by-side with the wildtype epitope under identical conditions described above.

CTL lines specific for the HLA-A2.1-restricted CEA.691 and MAGE3.112 epitopes were derived by repeated in vitro restimulations of human PBMCs with peptide-loaded dendritic cells or adherent monocytes, as described in Preparation C.

A total of 117 CEA.691 and 116 MAGE3.112 analogs were generated by systematically replacing each residue with 17 different single amino acids. CEA.691 is IMIGVLVGV (SEQ ID NO: 1); MAGE3.112 is KVAELVHFL (SEQ. ID. NO: 4). The residues Cys, Trp and Met were in general avoided unless they corresponded to conservative changes. Substitutions were introduced at all positions in the peptide except at the main MHC anchor positions, position 2 and the C-terminus.

Figures 1A, 1B:
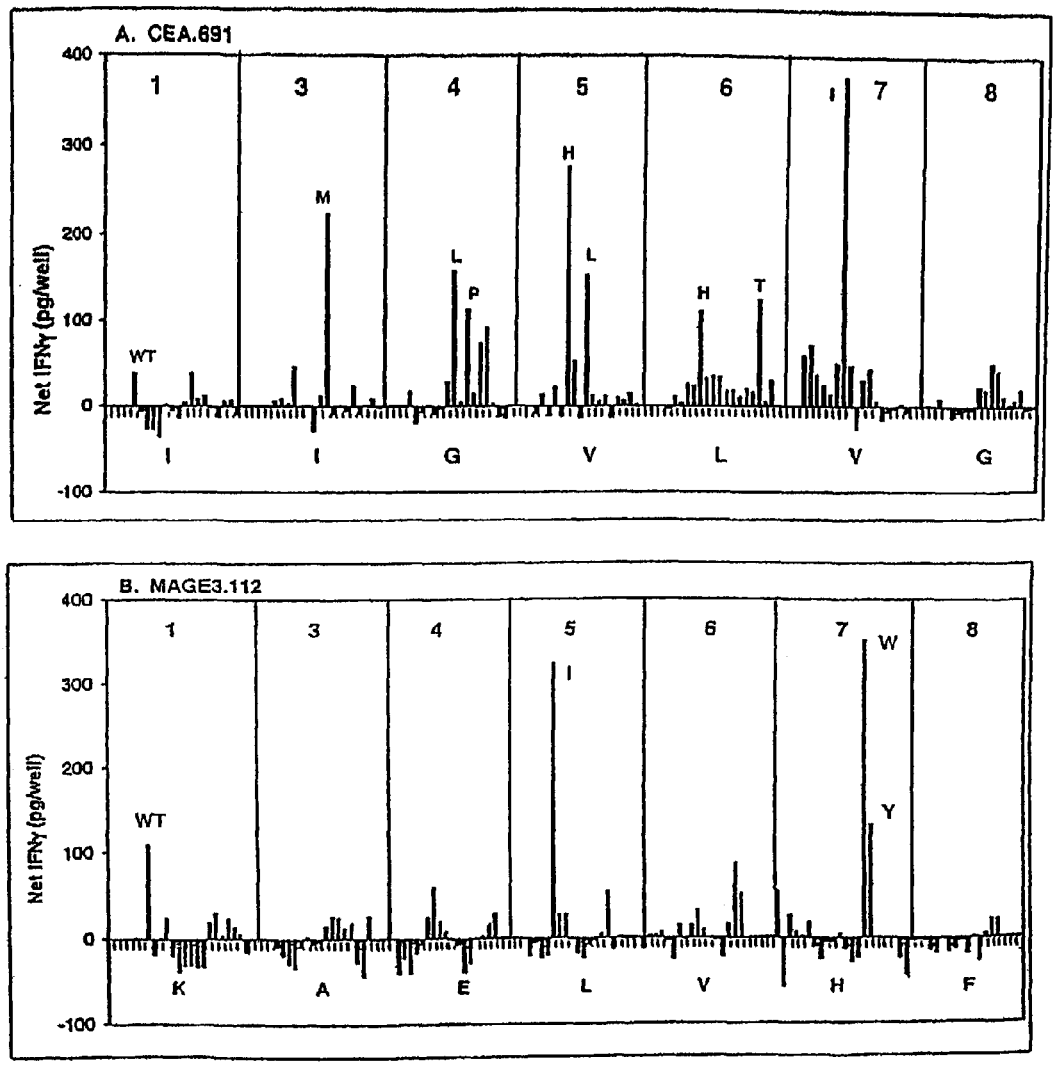

These analogs were then tested in vitro for their antigenicity. As described above, preliminary dose titration experiments for each CTL line were performed to define an antigen concentration at which IFNγ production in response to wildtype peptide was barely detectable. This suboptimal concentration was then used subsequently for all antigenicity analysis on analog peptides for each epitope, to identify analogs associated with increased T cell stimulatory capacity. Results of such antigenicity analysis are shown in FIG. 1. As shown in FIG. 1A, the suboptimal 100 ng/ml dose the wildtype CEA.691 peptide yielded only marginal IFNγ production (<50 pg/well). By contrast, at the same dose, several CEA.691 analogs (M3, L4, P4, H5, L5, H6, T6, and I7) induced detectable levels of IFNγ production, in the 150 to 350 pg/well range. As shown in FIG. 1B, MAGE3.112-specific CTL line 100 ng/ml of wildtype peptide induced the release of 100 pg/ml of IFNγ, whereas two analogs (I5 and W7) were associated with inducing IFNγ levels of over 300 pg/well.

All analogs of CEA.691 and MAGE3.112 that stimulated IFNγ above 100 pg/well were chosen for further characterization and a complete dose titration was carried out to identify heteroclitic analogs. Heteroclitic analogs are those that stimulate significant IFNγ release (>100 pg/well) at 10-fold or lower peptide concentrations than wildtype peptide. For the CEA.691 epitope two different analogs, M3 (SEQ ID NO: 2) and H5 (SEQ ID NO: 3), were identified. As seen in FIG. 1C, for epitope CEA.691, the wildtype peptide yielded a significant detectable IFNγ signal in the 1 to 100 µg/ml dose range, while the analogs M3 and H5 stimulated significant release with as little as 0.01 ng/ml of peptide. By these criteria, these two CEA.691 analogs are, on a molar basis, 100,000-fold more potent in terms of IFNγ release than their unmodified wildtype counterpart.

Similarly, for the MAGE3.112 epitope two heteroclitic analogs, I5 and W7, were identified. As shown in FIG. 1D, 1 µg/ml of wildtype peptide concentration is required for significant IFNγ release whereas 0.1 ng/ml of either I5 (SEQ ID NO:5) or W7 (SEQ ID NO:6) analogs was required to stimulate an equivalent response. This corresponds to a greater than 100,000-fold increase in biological activity compared to wildtype peptide.

In general, the modification of a wildtype Class I epitope by substitution with a conservative or semi-conservative amino acid at position 3 and/or 5 and/or 7 of the epitope to generate a heteroclitic analog enhances the immune response to the corresponding wildtype epitope. The heteroclitic analogs not only induced a dose response shift, but also stimulated CTL's to produce higher levels of IFNγ compared to wildtype peptide so that the maximal dose response (plateau) reached in response to the analog was much higher than the response obtained in response to the unmodified antigen.

Example 2

Identification of Additional Heteroclitic Analogs

Three additional A2.1-restricted epitopes, the MAGE2.157 YLQLVFGIEV, SEQ ID NO: 7 tumor epitope, and two epitopes from viral antigens, HBV Pol.455, GLSRYVARL (SEQ ID NO: 16) and HIV Pol.476 ILKEPVHGV (SEQ ID NO: 18), were analyzed. All of these epitopes have previously been shown to be immunogenic for CTL.

A panel of 240 different analogs was synthesized which included five conservative and five non-conservative amino acid substitutions at epitope positions 3, 5, 7 in each of the three epitopes, as well as at epitope positions 1, 4, 6, using the amino acid conservancy assignments described in the Preparation B and in Table 2. These analogs were tested for heteroclicity using murine CTL lines generated in HLA-A2.1/$K^{bxs}$ transgenic mice and following an experimental strategy similar to the one described in Example 1 for the CEA.691 and MAGE3.112 epitopes. Murine CTL lines derived from HLA transgenic mice were used instead of human CTL lines due to technical ease associated with generating and maintaining mouse lines.

Figure 2A:
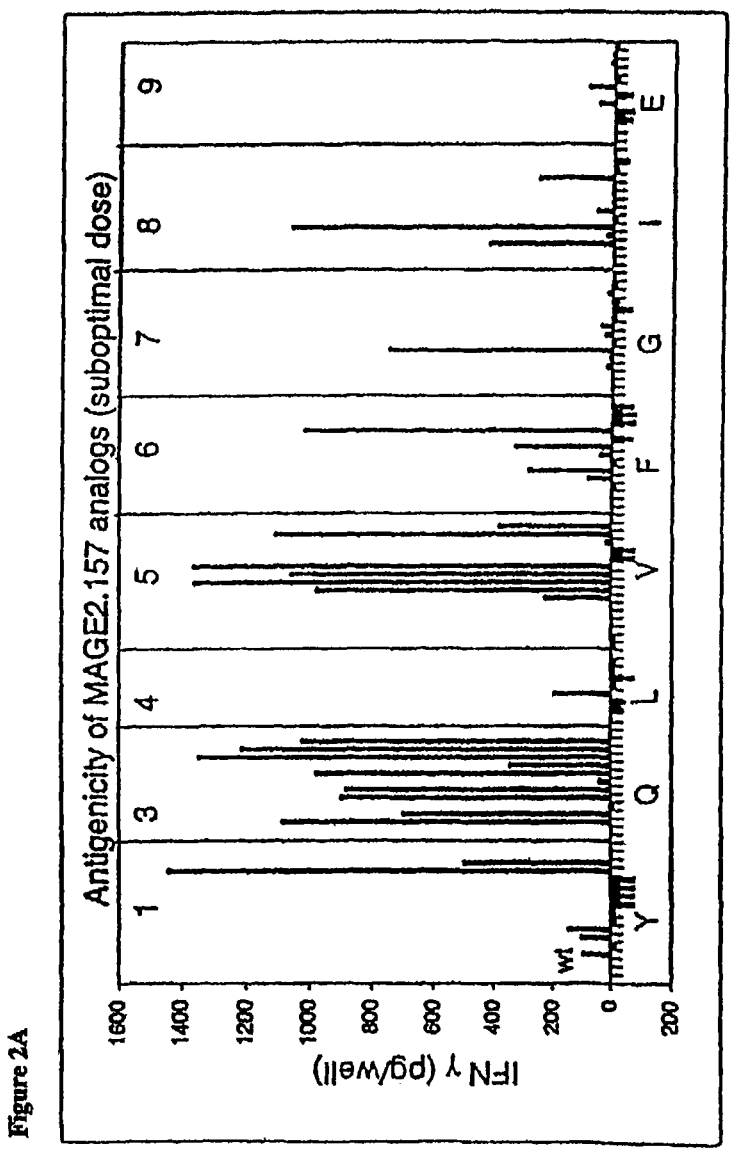
Figure 2B:
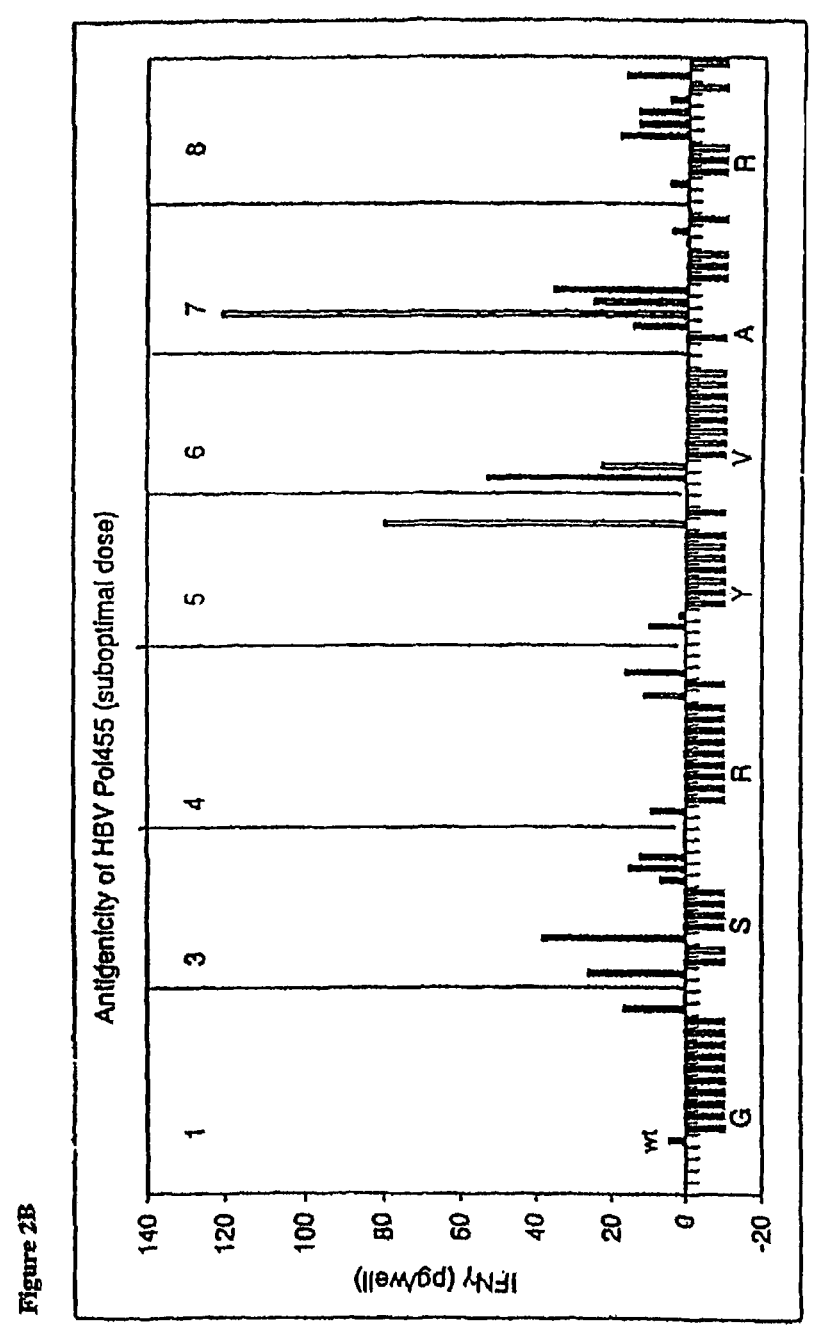
Figure 2C:
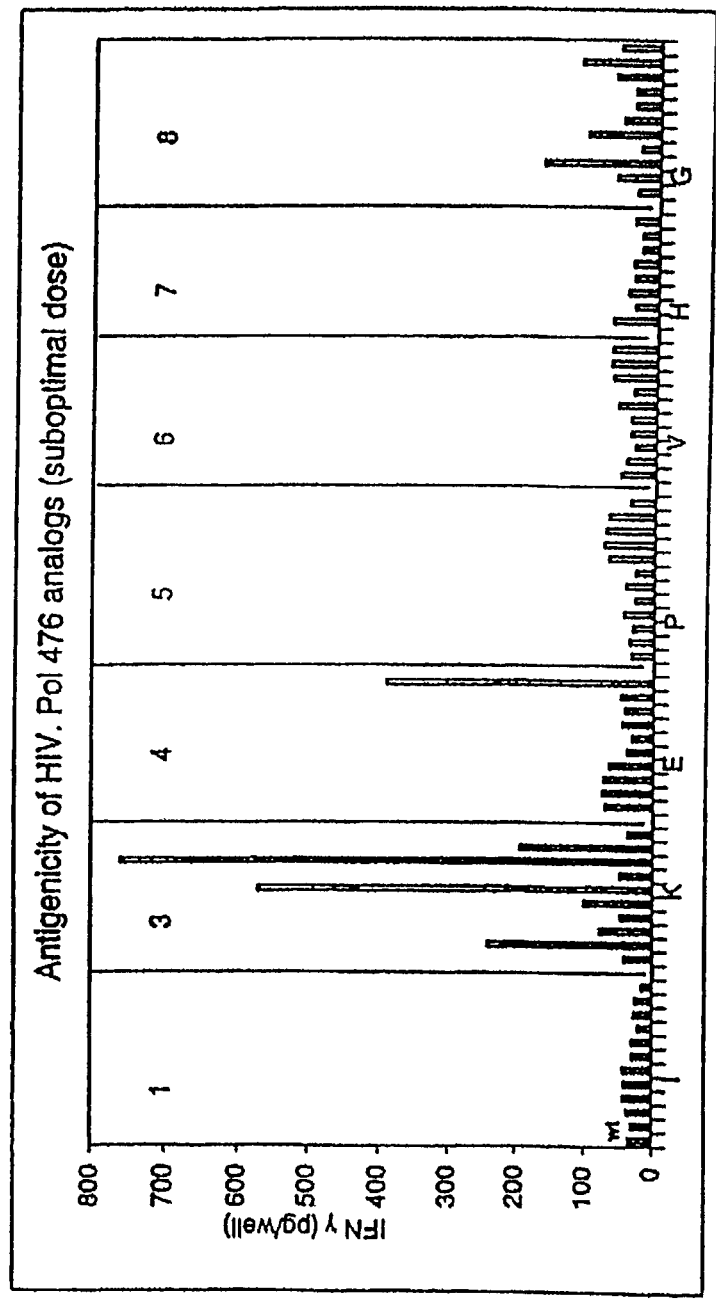

The results are shown in FIG. 2A (MAGE2.157), 2B (HBV Pol.455), and 2C (HIV Pol.476) with a corresponding dose titration profile for HIV Pol.476 in FIG. 2D. (See Example 3 for MAGE2.157 and HIV Pol.455.)

Analysis of a total of 85 different analogs of the MAGE2.157 epitope tested resulted in identification of two heteroclitic analogs, 15 (SEQ ID NO: 8) and F5 (SEQ ID NO: 9), that stimulated IFNγ responses at 100- to 100,000-fold lower doses than wildtype peptide (Table 1); both of these analogs had substitutions that were conservative or semi-conservative in nature occurring at an odd-numbered position in the center of the peptide (position 5).

For the HIV Pol.476 epitope, out of 78 different analogs screened, two were identified as having heteroclitic activity (H3 (SEQ ID NO: 19) and L3 (SEQ ID NO: 20)) (Table 1); both analogs carried either a conservative or semi-conservative substitution at an odd-numbered position in the center of the peptide. one heteroclitic analog of HIV Pol.455 epitope out of 77 tested was identified; this analog had a conservative substitution (P) at position 7 of the peptide (SEQ ID NO: 17) (Table 1). An additional HIV Pol.476 analog is prepared and tested (ILIEPVHGV) (SEQ ID NO: 53).

Thus, data obtained from 240 analogs for three additional epitopes of tumor and viral origin (MAGE2.157, HIV Pol.476, and HBV Pol.455), were consistent with the analysis of the MAGE3.112 and CEA.691 epitopes as set forth in Example 1.

Heteroclicity analysis was also performed on two p53 epitopes. One epitope, p53.149M2, SMPPPGTRV (SEQ ID NO: 10) represents a fixed anchor analog of a human p53 epitope having a methionine residue substitution which enhances MHC binding. The second epitope, p53 Mu.184, GLAPPQHLIRV (SEQ ID NO: 13) has a sequence that is completely conserved between mice and humans (Theobald, et al., 92(26):11993 (1995)).

Figure 5:
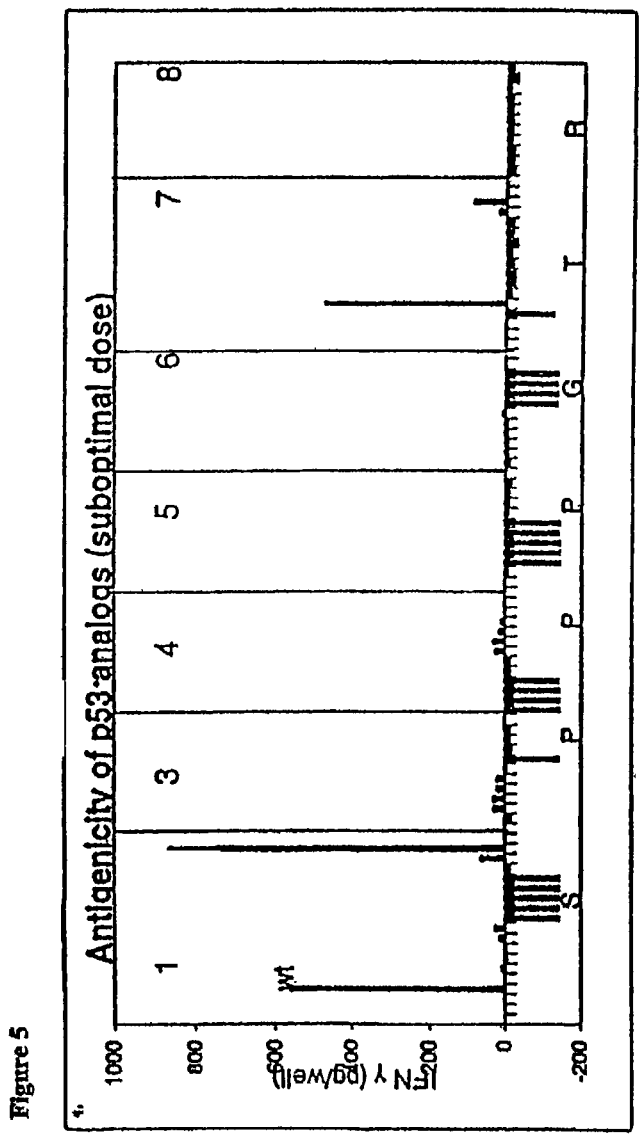
FIG. 5 shows the results of testing a panel of potential heteroclitic analogs of the epitope p53.149M2 with respect to IFNγ production from appropriate CTLs.

Dose titration analysis performed on the p53.149M2 revealed optimal and suboptimal responses at 1 µg/ml and 0.1 µg/ml dose range. A panel of 76 analogs for p53.149M2 (five conservative and five non-conservative substitutions at each position) was screened and only two analogs, C1 (SEQ ID NO: 11) and P7 (SEQ ID NO: 12), were identified both giving IFNγ release of 100 pg/well at a suboptimal dose, FIG. 5. On further analysis, both analogs induced significant IFNγ production at 10-fold lower concentrations than wildtype peptide. In addition, the C1 analog also induced significant IL10 levels at 100-fold lower peptide concentrations, FIG. 6.

Figure 7:
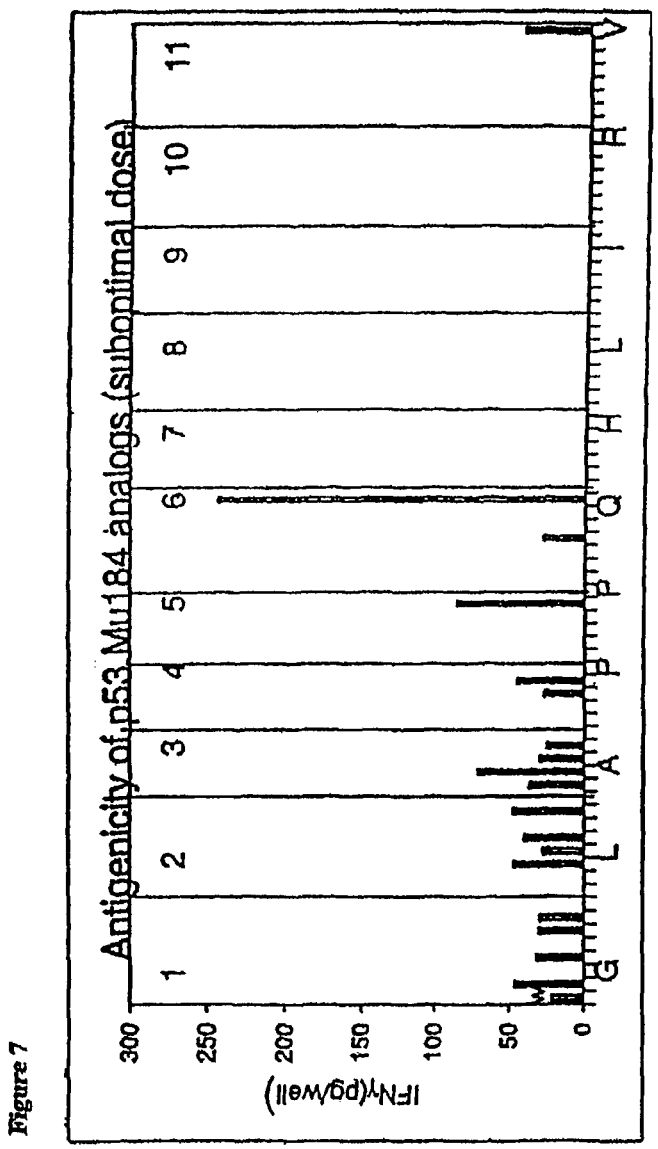
FIG. 7 shows the results of testing a panel of potential analogs of p53.Mu184 epitope for IFNγ production in CTLs.
Figure 8:
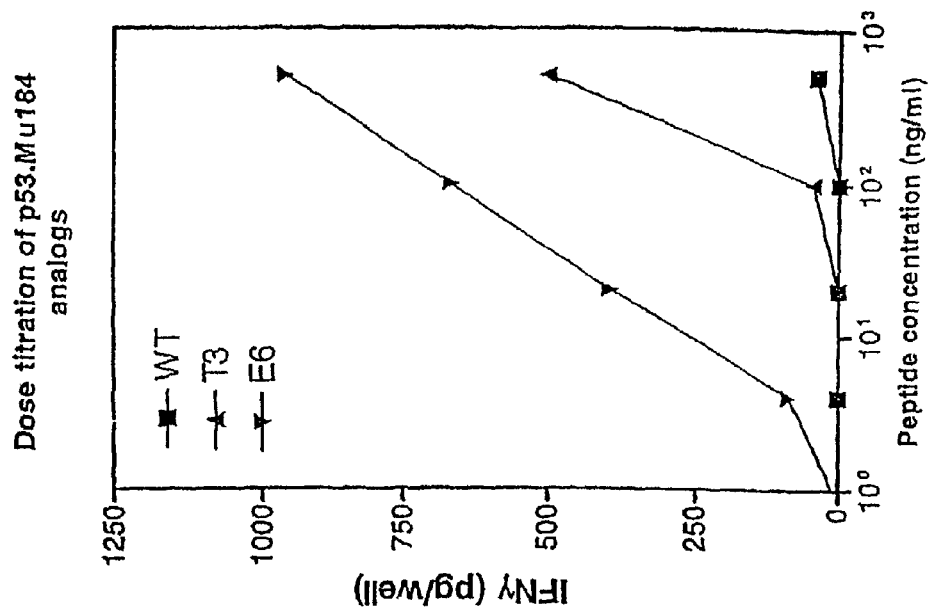
FIG. 8 shows the dose response curve for wildtype and two successful heteroclitic analogs of p53.Mu184 with respect to IFNγ production.

For the p53mu.184 epitope optimal and suboptimal levels of peptide were determined to be 500 ng/ml and 10 ng/ml respectively after performing a dose titration analysis. A panel of 63 conservative and semi-conservative substitution analogs were tested for immunogenicity. Two analogs with enhanced immunogenicity were found-T3 (SEQ ID NO: 14) and T3,E6 (SEQ ID NO: 15). See FIGS. 7 and 8.

Example 3

Lymphokine Profile Induced by Heteroclitic Analogs

Figure 4:
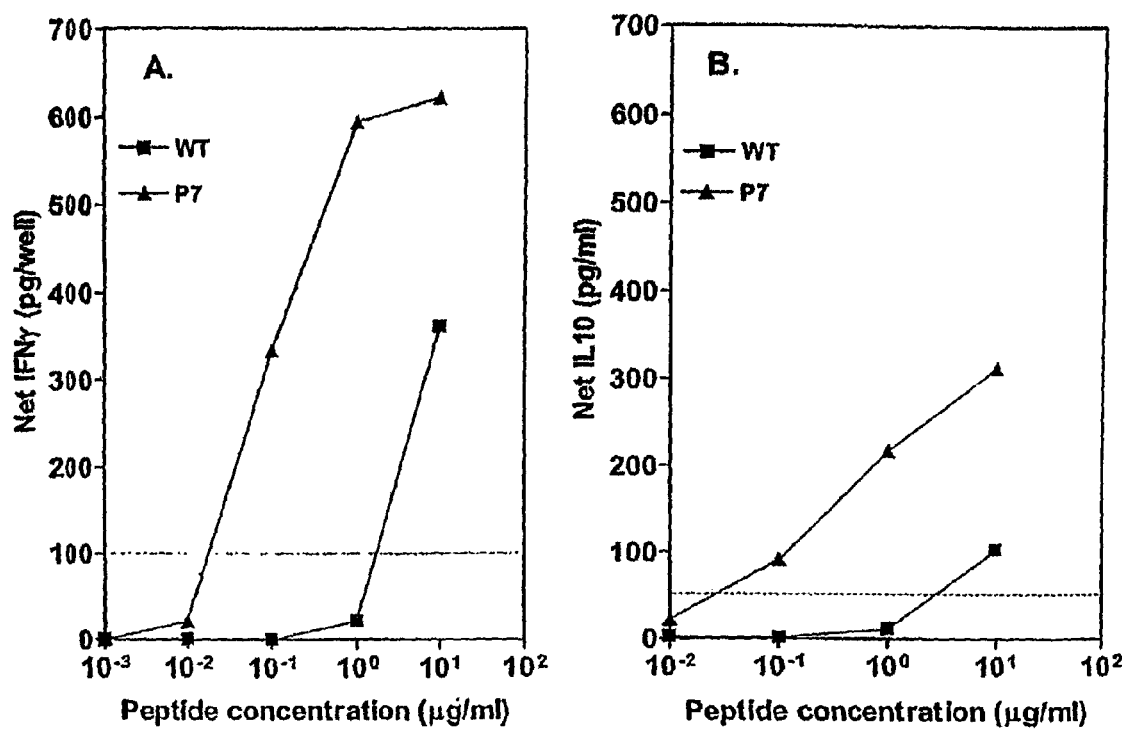
FIGS. 4A and 4B are the dose response curves for wildtype and a heteroclitic analog of HIVPol.476 to produce IFNγ and IL10 in appropriate CTLs.

Heteroclitic analogs have been shown previously to differentially activate cytokine production from T cells whereby some analogs specifically activate T cells to produce Th1 cytokines whereas others preferentially activate the production of Th2 cytokines. To investigate the pattern of lymphokine release associated with the heteroclitic analogs of the invention, the production of Th2 cytokines IL5 and/or IL10 from CTL lines was compared to the production of IFNγ. Representative data from two different epitopes are shown in FIGS. 3 and 4.

FIGS. 3A and 3B show the lymphokine profile induced by MAGE2.157 analogs. IFNγ (A) and IL10 (B) produced by MAGE2.157-specific CTL's in response to .221A2.1 targets pulsed with analogs I5 or F5, or wildtype (WT) peptide was measured over several different doses. Dotted lines indicate significant levels of IFNγ (100 pg/well) or IL10 (50 pg/ml). As seen in FIG. 3A, the F5 and I5 analogs of MAGE2.157 induced significant levels of IFNγ production at 100-fold or 10,000-fold lower concentrations than wildtype peptide respectively. Moreover, the same analogs also induced significant IL10 production at 10-fold or 100-fold lower peptide concentrations than wildtype peptide.

Data from another epitope, HBV Pol.455, depicting the same trend are shown in FIGS. 4A and 4B. IFNγ (A) or IL10 (B) released by HBV Pol.455 CTL's in response to analog P7 or wildtype (WT) peptide over several different peptide doses are shown. Once again, the P7 analog of HBV Pol.455 induced significant levels of IFNγ (FIG. 4A) and IL10 (FIG. 4B) at 100-fold lower peptide concentrations than wildtype peptide. Taken together the data summarizing all the heteroclitic analogs tested for induction of Th2 cytokines (Table 6) indicates that most heteroclitic analogs stimulate increased production of both of Th1 and Th2 cytokines.

Example 4

HLA-A2.1 Binding Affinity of Heteroclitic Analogs

To verify that the enhanced recognition by CTL lines observed was not due to a fortuitous increase in MHC binding capacity of the analog epitope, the MHC binding affinity of all heteroclitic analogs was measured in vitro utilizing purified HLA-A2.1 molecules, and compared to their unmodified wildtype counterparts as described in Preparation D.

As summarized in Table 6, three analogs (MAGE3.112 W7, HIV Pol.476 H3, and HIV Pol.476 L3) bound to HLA-A2.1 with four-fold or higher affinity than wildtype peptide and two analogs bound with lower affinity (MAGE2.157 I5, MAGE2.157 F5). The four remaining heteroclitic analogs, MAGE3.112 I5, CEA.691 M3, CEA.691 H5, and HBV Pol.455 P7, were associated with little or no change in HLA-A2.1 binding capacity. Collectively these data suggest a lack of correlation between increased binding and heteroclicity.

Example 5

Prediction and Immunogenicity of Analogs for the Murine p53.261 Epitope

To test for immunogenicity in vivo, the HLA-A2.1-restricted murine p53.261 epitope was used since CTL responses against this epitope have been shown to be partially tolerized in HLA-A2.1/K$^b$ transgenic mice. This permits analysis of the capacity of predicted heteroclitic analogs to break T cell tolerance in vivo. Although heteroclitic analogs heretofore have been detected through in vitro screening with CTL lines raised against wildtype epitopes, we reasoned that analogs identified by the substitution rules could potentially induce CTL in vivo that were heteroclitic against the wildtype epitope, an application of interest for designing vaccines against tolerant tumor-associated epitopes.

Immunogenicity for the p53.261 predicted analogs were tested in HLA-A2.1/K$^{bxd}$ transgenic mice by co-immunizing mice with 50 µg of the p53.261 epitope (LLGRDSFEV) (SEQ ID NO:21) or its predicted analogs and 140 µg of HBV Core. 128 helper epitope in IFA. Eleven days later, primed spleen cells were harvested and cultured in vitro with irradiated syngeneic LPS-activated spleen cells that had been pulsed with 10 µg/ml of peptide. After 10 days of culture, CTL were restimulated with peptide-pulsed LPS blasts in the presence of Con A-conditioned media as a source of IL2 (Ishioka, G., et al., *J. Immunol.* (1999) 162:3915). Spleen cells from mice immunized with the predicted analogs were stimulated in vitro against both wildtype peptide (to determine the cross-reactivity, avidity and precursor frequency of CTL's that respond to wildtype antigen) and the respective immunizing analog (to determine avidity and precursor frequency of CTL's responding to the analog). All short-term, bulk populations of CTL were tested for peptide specificity by the IFNγ in situ ELISA assay 5 days after the second restimulation in vitro, using Jurkat-A2.1 tumor cells as APC. Alternatively, CTL responses were performed on freshly isolated spleen cells from immunized animals using the Elispot assay.

A panel of nine analogs of the p53.261 epitope consisting of three conservative or semi-conservative substitutions at positions 3, 5, and 7 of the 9-mer peptide was tested for immunogenicity in HLA-A2.1/$K^{bxd}$ transgenic mice. Immunization of mice with each of the nine analogs and in vitro expansion of primed splenocytes with the respective immunizing analog resulted in identification of six analogs (L7, D3, H7, H3, N5, G5) that gave CTL responses characterized by IFNγ production of 100 pg/well at much lower peptide concentrations compared to CTL induced in vivo and expanded in vitro with wildtype peptide.

Spleen cells from mice immunized with either WT peptide or the indicated analogs were stimulated in vitro with the corresponding immunizing peptide (FIGS. 9A, B) or with WT peptide (FIGS. 9C, D). IFNγ release by these CTL's was then measured over a dose range against targets pulsed with the immunizing peptide (FIGS. 9A, B) or with WT peptide (FIGS. 9C, D). IFNγ release at 100 pg/well is shown as a dotted line. These results indicate that a significant percentage of the analogs induce CTL of a higher avidity than those induced by wildtype peptide itself.

The cross-reactivity of CTL primed with these heteroclitic analogs against wildtype peptide is shown in FIG. 9C and FIG. 9D. While CTL's obtained from animals immunized and restimulated with wildtype peptide induced 100 pg/well IFNγ at peptide doses between 0.1-10 μg/ml, CTL's obtained from animals immunized with analogs L7, H3, and D3, and stimulated and tested in vitro with wildtype peptide, required 10-, 100-, or 1000-fold lower doses of wildtype peptide respectively, to induce 100 pg/well of IFNγ (FIG. 9C). This suggests that in three out of six cases the predicted heteroclitic analogs were 10-1000-fold more active/potent at inducing CTL's reactive to wildtype peptide in situations where partial CTL tolerance to wildtype antigen exists.

Example 6

Cross Reactivity with Wildtype

The cross-reactivity of CTL induced by the D3 and H3 analogs were also tested against the wildtype epitope naturally processed by a p53-expressing Meth A tumor cell clone transfected with HLA-A2.1/$K^b$; it was found that CTL generated by p53.261 analogs that are heteroclitic for wildtype epitope respond to endogenously-processed p53.261 epitope presented by Meth A/A2.1$K^b$ tumor cells.

The CTL population ($10^5$/well) were cultured with 2.5× $10^4$ Meth A tumor cells or with a Meth A clone transfected with HLA-A2.1/$K^b$ and IFNγ release was measured by the in situ ELISA assay. As shown in FIG. 10, CTL lines raised against both D3 and H3 analogs of the p53.261 epitope responded to the endogenous epitope expressed by a Meth A/A2.1$K^b$ tumor cell clone but not to the parental HLA-A2.1-negative Meth A tumor cell line.

Example 7

Precursor Frequency Analysis Using Elispot Assays

To confirm that cross-reactive CTL against wildtype peptide are generated in mice immunized with analogs CD8+ cells were isolated from spleen cells of mice immunized with analogs or wildtype peptide, without further CTL expansion in vitro and the precursor frequency of CTL reactive against either wildtype or analog was determined using an Elispot assay.

CD8+ cells isolated from mice immunized with either WT peptide or the D3, H3, L7, and H7 analogs were analyzed for their ability to release IFNγ when stimulated in the Elispot assay with WT peptide. FIG. 11 shows that while the precursor frequencies of wildtype peptide-reactive CTL were $1/66,000$ (15 spots/$10^6$) in mice immunized with wildtype peptide, precursor frequencies of wildtype peptide-reactive cells in mice immunized with predicted analogs were approximately $1/15,000$ for analogs D3, H3, and L7 (60-75 spots/$10^6$ cells), and $1/83,000$ (12 spots/$10^6$) for analog H7. This indicates wildtype-reactive cells were present at a four-fold higher frequency in mice immunized with three out of the four analogs compared to mice immunized with the native peptide. This finding is significant since it implies that in vivo immunization with heteroclitic analogs does indeed induce a higher number of CTL reactive against wildtype peptide, using a more direct assay system where in vitro expansion of in vivo-primed CTL is avoided.

Example 8

Heteroclitic Analogs Induce Human CTL Capable of Recognizing Tumor Cells In Vitro Immunogenicity of heteroclitic analogs of MAGE3.112 was also tested by inducing primary CTL from PBMC, as described in Preparation C, against either the MAGE3.112 peptide or the I5 and W7 analogs of this epitope. After two rounds of in vitro stimulation, PBMC cultures in 48-wells were scored positive for CTL induction if the net IFNγ production was >100 pg/well and production was at least two-fold above background, after stimulating with .221-A2.1 APC in the presence or absence of peptide.

To underline the physiologic relevance of our observations to human tumor antigens, we examined whether heteroclitic analogs of the MAGE3.112 epitope could induce human CTL's in a primary in vitro induction system. Fresh naïve human PBMC from normal donors were stimulated repetitively in vitro with either wildtype or analogs as described previously (Kawashima, I., et al., *Human Immunol.* (1998) 59:1). Peptide-specific CTL responses were detected in cultures stimulated with either wildtype peptide (FIG. 12A) or the I5 (FIG. 12B) and W7 analogs (FIG. 12C). Briefly, .221A2.1 cells were pulsed overnight with 10 μg/ml of WT peptide (FIG. 12A), the I5 (FIG. 12B) analog, or the W7 analog (FIG. 12C). IFNγ production by CTL's growing in individual wells from a 48-well plate were tested against .221A2.1 cells in the presence or absence of peptide, or against the endogenous epitope-negative 888mel and the endogenous epitope-positive 624mel tumor cell lines. Only wells showing a positive peptide-specific CTL response are shown.

More importantly cultures induced with these analogs recognized the 624mel tumor cell line that endogenously processes and presents the wildtype sequence. This demonstrates that heteroclitic analogs can induce physiologically relevant human CTL's that recognize endogenously-generated wildtype peptide presented by tumor cells and that the phenomenon is relevant in both human and in transgenic mouse systems.

Example 9

Synthesis and Analysis of Heteroclitic Analogs Derived from the HLA-A2.1 Supermotif on HLA A2 Superfamily Members To further validate the heteroclitic substitution rules for other HLA molecules within the A2 superfamily, the panel of nine analogs of the p53.261 epitopes discussed above consisting of three conservative/semiconservative substitutions at positions 3, 5 and 7 are tested for in vivo immunogenicity in transgenic mice expressing one of the following human HLA molecules: A*0202, A*0203, A*0204, A*0205, A*0206, A*0207, A*0209, A*0214, A*6802 and A*6901.

CTLs from the mice immunized with the above-described analogs are tested for induction of at least 100 pg/well of IFNγ production. This IFNγ production typically occurs at much lower peptide concentrations than those induced and restimulated with wildtype peptide (e.g., the p53.261 epitope). These results indicate that our predicted heteroclitic analogs are more potent at inducing higher avidity CTL against the native wildtype epitope than wildtype peptide itself.

Typically, CTLs obtained from animals immunized and restimulated with a wildtype peptide will induce 100 pg/well IFNγ at peptide doses of 5-10 µg/ml, whereas CTLs obtained from animals immunized with the above-described analogs, and stimulated and tested in vitro with wildtype peptide, require 10-fold, 100-fold or even 1000-fold lower doses of wildtype peptide respectively, to induce 100 pg/well of IFNγ.

Example 10

Identification of Heteroclitic Analogs of a B7 Superfamily CTL Epitope, MAGE2.170

To better define the application of the invention to HLA Supertype families other than HLA-A2, analogs of the B7 superfamily epitope MAGE2.170 (sequence VPISHLYIL) (SEQ ID NO:46) were synthesized and screened in a fashion similar to that described previously for A2 superfamily epitopes. A panel of analogs of the MAGE2.170 epitope consisting of conservative/semi-conservative and non-conservative substitutions at every non-anchor position were screened at two suboptimal peptide doses using a human CTL line generated against the wildtype epitope. As previously described, this screening assay served to identify any potentially heteroclitic analogs that induce stronger CTL responses compared to wildtype peptide.

As shown in FIG. 13, analogs substituted at position 7 with either a H, M, E, G, or D residue stimulated IFNγ responses that were greater than the wildtype peptide when tested at the 0.01 µg/ml dose. When the stimulatory capacity of these five analogs were further analyzed in a peptide dose titration using the same wildtype epitope-specific CTL line, all of them demonstrated strong heteroclitic activity inasmuch as they all stimulated an equivalent level of IFNγ production (e.g. 200 pg/well) at >10-fold lower doses compared to the wildtype epitope, and the magnitude of response stimulated by the analogs was >2-fold greater than wildtype epitope at several peptide doses (FIG. 14).

To determine whether the heteroclitic activity of MAGE2.170 analogs was correlated with an increase or decrease in MHC binding activity, the binding affinity of the H7, M7, E7, G7, and D7 analogs to purified HLA-B7 molecules was determined relative to the wildtype epitope. Results shown in Table 7 indicate that there was no correlation between MHC binding of the analogs and heteroclicity inasmuch as 4 of the 5 MAGE2.170 analogs demonstrated binding affinities within a two-fold range of the wildtype peptide. The fifth epitope, MAGE2.170 D7, demonstrated a >100-fold decrease in binding compared to the wildtype peptide, therefore an enhancement in MHC binding could not account for the heteroclitic activity observed with this analog.

In summary, these results indicate that heteroclitic analogs can be generated from a B7 superfamily epitope by introducing single amino acid substitutions and that the substitution pattern showed similarity and differences with A2 heteroclitic epitopes. Like A2 heteroclitic epitopes, heteroclitic analogs of the B7 superfamily epitope MAGE2.170 could be generated by introducing substitutions at an odd-number position in the middle of the peptide (position 7). The nature of the substitutions for the MAGE2.170 epitope was either conservative/semi-conservative (the Y→H and Y→M substitutions) or non-conservative (the Y→E, Y→G, and Y→D substitutions) compared to the native residue (Table 7). Thus, the observation that non-conservative substitutions can result in heteroclitic analogs for the MAGE2.170 CTL epitope indicate a partially overlapping substitution pattern than that observed with A2 superfamily epitopes.

Example 11

Synthesis and Analysis of Heteroclitic Analogs Derived from the HLA-B7 Supermotif on HLA B7 Superfamily Members To further validate the heteroclitic substitution rules, additional studies are carried out with heteroclitic analogs derived from a peptide bearing a sequence within the HLA-B7 supermotif. For example, the analogs can be tested for in vivo immunogenicity.

For this study, the HLA-B7 supermotif bearing peptide, APRTLVYLL (SEQ. ID.NO:39) epitope is chosen and synthesized. A panel of analogs consisting of three conservative/semiconservative substitutions at positions 3, 5 and 7 of the 9-mer peptide, are tested for immunogenicity in HLA-B*0702/$K^b$ transgenic mice. The panel includes APETLVYLL (SEQ ID NO:40), APRTWVYLL (SEQ ID NO:41), and APRTLVPLL (SEQ ID NO:42), corresponding to a semi-conservative change is the third, fifth and seventh position, respectively.

CTLs from the mice immunized with the above-described analogs are tested for induction of at least 100 pg/well of IFNγ production. This IFNγ production will typically occur at much lower peptide concentrations than those induced and restimulated with wildtype peptide (e.g., APRTLVYLL) (SEQ ID NO:39). These results will indicate that our predicted heteroclitic analogs are more potent at inducing higher avidity CTL than wildtype peptide itself.

Typically, CTLs obtained from animals immunized and restimulated with a wildtype peptide will induce 100 pg/well IFNγ at peptide doses of 5-10 µg/ml, whereas CTLs obtained from animals immunized with the above-described analogs, and stimulated and tested in vitro with wildtype peptide, require 10-fold, 100-fold or even 1000-fold lower doses of wildtype peptide respectively, to induce 100 pg/well of IFNγ.

To further validate the heteroclitic substitution rules for other HLA molecules with the B7 superfamily, the peptides APETLVYLL (SEQ ID NO:40), APRTWVYLL (SEQ ID NO:41) and APRTLVPLL (SEQ ID NO:42) are tested for in vivo immunogenicity in transgenic mice expressing one of the following human HLA molecules: B*0702, B*0703, B*0704, B*0705, B*1508, B*3501, B*3502, B*3503, B*3503, B*3504, B*3505, B*3506, B*3507, B*3508, B*5101, B*5102, B*5103, B*5104, B*5105, B*5301, B*5401, B*5501, B*5502, B*5601, B*5602, B*6701 and B*7801.

CTLs from the mice immunized with the above-described analogs are tested for induction of at least 100 pg/well of IFNγ production. This IFNγ production will typically occur at much lower peptide concentrations than those induced and restimulated with wildtype peptide (e.g., APRTLVYLL) (SEQ ID NO:39). These results will indicate that our predicted heteroclitic analogs are more potent at inducing higher avidity CTL than wildtype peptide itself.

Typically, CTLs obtained from animals immunized and restimulated with a wildtype peptide will induce 100 pg/well IFNγ at peptide doses of 5-10 μg/ml, whereas CTLs obtained from animals immunized with the above-described analogs, and stimulated and tested in vitro with wildtype peptide, require 10-fold, 100-fold or even 1000-fold lower doses of wildtype peptide respectively, to induce 100 pg/well of IFNγ.

Precursor Frequency Analysis Using Elispot Assays

To confirm that cross-reactive CTL against wildtype peptide are generated in mice immunized with analogs, CD8+ cells are isolated from spleens immunized with analogs or wildtype peptide without further CTL expansion in vitro. From this material, the precursor frequency of CTL reactive against either wildtype or analog using Elispot assay is determined. The precursor frequencies of wildtype peptide reactive CTLs are typically much lower than the precurser frequencies of the analogs.

Heteroclitic Analogs can Induce Human CTL Capable of Recognizing Epitopes in vitro Heteroclitic analogs can be analyzed for induction of CTLs in a primary in vitro induction system. Fresh naïve human PBMC from normal donors are stimulated repetitively in vitro, with either wildtype or analogs, in 48 well plates as described previously. Peptide specific CTL responses are then detected in cultures stimulated with either a wildtype peptide or a heteroclitic analog. Cultures induced with these analogs can recognize targets that are endogenously processed and present the wildtype sequence. This demonstrates that heteroclitic analogs can induce physiologically relevant human CTLs that recognize endogenously generated wildtype peptide expressed on cells and that the phenomenon is relevant in both human and in transgenic mouse systems.

Example 12

Synthesis and Analysis of Heteroclitic Analogs Derived from the HLA-A3 Supermotif on HLA A3 Superfamily Members To further validate the heteroclitic substitution rules, additional studies are carried out with heteroclitic analogs derived from a peptide bearing a sequence within the HLA-A3 supermotif. For example, the analogs can be tested for in vivo immunogenicity.

For this study, the HLA-A3 supermotif bearing peptide, KVFPYALINK (SEQ ID NO:29) epitope is chosen and synthesized. A panel of analogs of SEQ ID NO:29 consisting of three conservative/semiconservative substitutions at positions 3, 5 and 7 of the 9-mer peptide, are tested for immunogenicity in HLA-A*3101/K$^b$ transgenic mice. The panel includes KVHPYALINK (SEQ ID NO:43), KVFPQALINK (SEQ. ID.NO:44) and KVFPYAKINK (SEQ ID NO:45), corresponding to a semi-conservative change in the third, fifth and seventh position, respectively.

CTLs from the mice immunized with the above-described analogs are tested for induction of at least 100 pg/well of IFNγ production. This IFNγ production typically occurs at much lower peptide concentrations than those induced and restimulated with wildtype peptide (e.g., KVFPYALINK) (SEQ ID NO:29). These results indicate that our predicted heteroclitic analogs are more potent at inducing higher avidity CTL against wildtype than wildtype peptide itself.

Typically, CTLs obtained from animals immunized and restimulated with a wildtype peptide induce 100 pg/well IFNγ at peptide doses of 5-10 μg/ml, whereas CTLs obtained from animals immunized with the above-described analogs, and stimulated and tested in vitro with wildtype peptide, require 10-fold, 100-fold or even 1000-fold lower doses of wildtype peptide respectively, to induce 100 pg/well of IFNγ.

To further validate the heteroclitic substitution rules for other HLA molecules with the A3 superfamily, the peptides KVHPYALINK (SEQ ID NO:43), KVFPQALINK (SEQ ID NO:44) and KVFPYAKINK (SEQ ID NO:45) are tested for in vivo immunogenicity in transgenic mice expressing one of the following human HLA molecules: A*0301, A*1101, A*3101, A*3301 and A*6801.

CTLs from the mice immunized with the above-described analogs are tested for induction of at least 100 pg/well of IFNγ production. This IFNγ production typically occurs at much lower peptide concentrations than those induced and restimulated with wildtype peptide (e.g., KVFPYALINK) (SEQ ID NO:29). These results will indicate that our predicted heteroclitic analogs are more potent at inducing higher avidity CTL than wildtype peptide itself.

Typically, CTLs obtained from animals immunized and restimulated with a wildtype peptide induce 100 pg/well IFNγ at peptide doses of 5-10 μg/ml, whereas CTLs obtained from animals immunized with the above-described analogs, and stimulated and tested in vitro with wildtype peptide, require 10-fold, 100-fold or even 1000-fold lower doses of wildtype peptide respectively, to induce 100 pg/well of IFNγ.

Precursor Frequency Analysis Using Elispot Assays

To confirm that cross-reactive CTL against wildtype peptide are generated in mice immunized with analogs, CD8+ cells are isolated from spleens immunized with analogs or wildtype peptide without further CTL expansion in vitro. From this material, the precursor frequency of CTL reactive against either wildtype or analog using Elispot assay is determined. The precursor frequencies of wildtype peptide reactive CTLs are typically much lower than the precurser frequencies of the analogs.

Heteroclitic Analogs can Induce Human CTL Capable of Recognizing Epitopes in vitro Heteroclitic analogs are analyzed for induction of CTLs in a primary in vitro induction system. Fresh naïve human PBMC from normal donors are stimulated repetitively in vitro, with either wildtype or analogs, in 48 well plates as described previously. Peptide specific CTL responses are then detected in cultures stimulated with either a wildtype peptide or a heteroclitic analog. Cultures induced with these analogs recognize targets that are endogenously processed and present the wildtype sequence. This demonstrates that heteroclitic analogs induce physiologically relevant human CTLs that recognize endogenously generated wildtype peptide expressed on cells and that the phenomenon is relevant in both human and in transgenic mouse systems.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

TABLE 1

| SEQ. ID NO: 1 | IMIGVLVGV | CEA.691 |
| SEQ. ID NO: 2 | IMMGVLVGV | CEA.691 M3 |
| SEQ. ID NO: 3 | IMIGHLVGV | CEA.691 H5 |
| SEQ. ID NO: 4 | KVAELVHFL | MAGE3.112 |
| SEQ. ID NO: 5 | KVAEIVHFL | MAGE3.112 I5 |
| SEQ. ID NO: 6 | KVAELVWFL | MAGE3.112 W7 |
| SEQ. ID NO: 7 | YLQLVFGIEV | MAGE2.157 |
| SEQ. ID NO: 8 | YLQLIFGIEV | MAGE2.157 I5 |
| SEQ. ID NO: 9 | YLQLFFGIEV | MAGE2.157 F5 |
| SEQ. ID NO: 10 | SMPPPGTRV | p53.149M2 |
| SEQ. ID NO: 11 | CMPPPGTRV | p53.149M2 C1 |
| SEQ. ID NO: 12 | SMPPPGPRV | p53.149M2 P7 |
| SEQ. ID NO: 13 | GLAPPQHLIRV | p53.Mu.184 |
| SEQ. ID NO: 14 | GLTPPQHLIRV | p53.Mu.184 T3 |
| SEQ. ID NO: 15 | GLTPPEHLIRV | p53.Mu.184 T3,E6 |
| SEQ. ID NO: 16 | GLSRYVARL | HBV Pol.455 |
| SEQ. ID NO: 17 | GLSRYVPRL | HBV Pol.455 P7 |

TABLE 1-continued

| SEQ. ID NO: 18 | ILKEPVHGV | HIV Pol.476 |
| SEQ. ID NO: 19 | ILHEPVHGV | HIV Pol.476 H3 |
| SEQ. ID NO: 20 | ILLEPVHGV | HIV Pol.476 L3 |
| SEQ. ID NO: 21 | LLGRDSFEV | p53.261 |
| SEQ. ID NO: 22 | LLDRDSFEV | p53.261 D3 |
| SEQ. ID NO: 23 | LLHRDSFEV | p53.261 H3 |
| SEQ. ID NO: 24 | LLGRDSLEV | p53.261 L7 |
| SEQ. ID NO: 25 | LLGRDSHEV | p53.261 H7 |
| SEQ. ID NO: 26 | LLGRNSFEV | p53.261 N5 |
| SEQ. ID NO: 27 | LLGRGSFEV | p53.261 G5 |
| SEQ. ID NO: 28 | APAAAAAAY | |
| SEQ. ID NO: 29 | KVFPYALINK | A3 wildtype |
| SEQ. ID NO: 30 | TPPAYRPPNAPIL | HBVCore.128 Th |
| SEQ. ID NO: 31 | FLPSDFFPSV | HBVCore.18 |
| SEQ. ID NO: 39 | APRTLVYLL | HLA-B7 |
| SEQ. ID NO: 48 | VPISHLYIL | MAGE2.170 |
| SEQ. ID NO: 49 | VPISHLHIL | MAGE2.170 H7 |
| SEQ. ID NO: 50 | VPISHLMIL | MAGE2.170 M7 |
| SEQ. ID NO: 51 | VPISHLGIL | MAGE2.170 G7 |
| SEQ. ID NO: 52 | VPISHLEIL | MAGE2.170 E7 |
| SEQ. ID NO: 53 | VPISHLDIL | MAGE2.170 D7 |

Table 2. Compiled rankings and similarity assignments.

| A | | C | | D | | E | | F | | G | | H | | I | | K | | L | |
|---|---|---|---|---|---|---|---|---|---|---|---|---|---|---|---|---|---|---|---|
| A | 1.0 | C | 1.0 | D | 1.0 | E | 1.0 | F | 1.0 | G | 1.0 | H | 1.0 | I | 1.0 | K | 1.0 | L | 1.0 |
| S | 4.5 | V | 5.5 | N | 3.5 | Q | 3.3 | L | 3.8 | S | 2.8 | Q | 2.0 | L | 2.5 | R | 2.7 | I | 3.3 |
| T | 4.8 | T | 6.5 | E | 4.0 | N | 4.2 | Y | 4.3 | A | 4.2 | E | 5.8 | M | 4.5 | Q | 6.0 | M | 4.0 |
| P | 5.3 | A | 6.7 | Q | 6.2 | D | 4.7 | I | 4.8 | T | 4.7 | N | 6.2 | F | 5.2 | H | 6.8 | F | 4.5 |
| G | 5.7 | S | 7.3 | T | 7.2 | H | 5.3 | M | 6.2 | D | 6.3 | R | 8.2 | V | 5.2 | N | 7.2 | V | 5.5 |
| C | 9.3 | P | 8.0 | S | 7.7 | T | 8.3 | V | 6.7 | P | 7.0 | K | 8.7 | Y | 8.8 | E | 7.5 | Y | 8.2 |
| V | 9.5 | I | 9.0 | H | 7.8 | K | 8.7 | W | 7.2 | N | 7.3 | P | 9.0 | T | 10.3 | D | 8.5 | H | 9.7 |
| D | 10.0 | Y | 10.2 | G | 8.8 | P | 9.0 | H | 10.2 | E | 8.3 | D | 9.2 | H | 11.3 | M | 9.2 | Q | 10.5 |
| M | 10.0 | N | 10.7 | P | 9.2 | R | 10.5 | C | 11.2 | Q | 9.3 | S | 10.5 | A | 11.5 | T | 10.5 | W | 11.0 |
| N | 10.2 | F | 11.0 | A | 9.3 | S | 10.5 | T | 11.5 | H | 9.8 | T | 10.5 | C | 11.7 | S | 11.3 | T | 11.3 |
| E | 11.3 | G | 11.0 | K | 9.5 | V | 11.0 | R | 11.8 | C | 11.5 | Y | 11.0 | K | 12.0 | P | 11.5 | A | 11.8 |
| Q | 11.3 | M | 11.0 | R | 11.5 | G | 12.0 | A | 13.0 | V | 12.0 | M | 11.2 | P | 12.0 | I | 12.2 | K | 12.2 |
| H | 12.3 | H | 11.3 | C | 12.0 | A | 12.2 | | | | | V | 12.2 | Q | 12.2 | L | 12.7 | P | 12.2 |
| Y | 13.0 | D | 12.0 | | | M | 12.3 | | | | | | | R | 13.0 | Y | 12.8 | | |

| M | | N | | P | | Q | | R | | S | | T | | V | | W | | Y | |
|---|---|---|---|---|---|---|---|---|---|---|---|---|---|---|---|---|---|---|---|
| M | 1.0 | N | 1.0 | P | 1.0 | Q | 1.0 | R | 1.0 | S | 1.0 | T | 1.0 | V | 1.0 | W | 1.0 | Y | 1.0 |
| L | 3.8 | D | 3.2 | T | 3.5 | E | 3.2 | K | 2.0 | T | 4.0 | P | 4.7 | L | 5.3 | F | 4.2 | F | 6.2 |
| I | 5.0 | E | 4.5 | S | 6.0 | H | 3.3 | H | 5.8 | G | 4.2 | S | 5.0 | I | 5.5 | Y | 4.5 | W | 6.3 |
| V | 5.2 | Q | 5.8 | A | 6.3 | N | 6.0 | Q | 6.7 | A | 4.7 | A | 5.7 | M | 5.5 | L | 6.3 | H | 7.3 |
| F | 7.0 | H | 6.8 | H | 7.2 | K | 7.0 | E | 8.7 | P | 5.3 | N | 6.5 | P | 7.8 | M | 6.5 | M | 8.0 |
| K | 9.7 | T | 7.2 | Q | 7.2 | D | 7.2 | N | 8.7 | N | 6.5 | D | 7.8 | T | 8.2 | R | 8.7 | L | 9.7 |
| Q | 10.3 | S | 7.7 | N | 7.8 | R | 8.3 | M | 9.2 | D | 8.0 | E | 8.3 | F | 8.5 | I | 9.2 | T | 10.0 |
| R | 10.5 | K | 8.5 | D | 9.2 | P | 8.5 | D | 10.0 | C | 9.3 | G | 8.8 | A | 10.0 | H | 10.2 | I | 10.3 |
| Y | 10.8 | P | 8.7 | E | 9.5 | M | 10.5 | P | 10.2 | E | 9.3 | H | 10.5 | C | 10.7 | V | 10.3 | C | 10.7 |
| H | 11.0 | R | 10.5 | G | 10.2 | T | 10.8 | W | 10.3 | H | 10.2 | Q | 10.5 | H | 11.0 | K | 10.5 | V | 11.0 |
| A | 11.2 | A | 10.7 | V | 11.2 | V | 11.3 | S | 11.3 | Q | 10.5 | V | 10.5 | Q | 11.0 | Q | 12.3 | P | 11.5 |
| T | 11.3 | G | 11.8 | C | 11.8 | S | 12.3 | T | 12.0 | K | 12.3 | C | 12.2 | E | 11.3 | S | 12.3 | A | 11.7 |
| P | 11.8 | V | 12.8 | M | 12.2 | A | 13.0 | I | 12.5 | | | K | 12.2 | N | 12.3 | A | 12.5 | N | 11.7 |
| W | 12.7 | | | | | | | L | 13.0 | | | M | 12.3 | S | 12.7 | P | 12.7 | Q | 12.0 |
| C | 13.0 | | | | | | | Y | 13.0 | | | | | T | 12.7 | | | S | 12.2 |
| | | | | | | | | | | | | | | | | | | K | 12.7 |
| | | | | | | | | | | | | | | | | | | R | 13.0 |
☐ Conserved (1-7)     Semi-conserved (7.1-13)     Non-conserved (13.1-20)

TABLE 3

| SUPER-MOTIFS | POSITION 2 (Primary Anchor) | POSITION 3 (Primary Anchor) | POSITION C Terminus (Primary Anchor) |
|---|---|---|---|
| A1 | T, I, *L, V, M, S* | | F, W, *Y* |
| A2 | L, I, V, M, *A, T, Q* | | I, V, *M, A, T, L* |
| A3 | V, S, M, A, *T, L, I* | | R, K |
| A24 | Y, F, *W, I, V, L, M, T* | | F, I, *Y, W, L, M* |
| B7 | P | | V, I, L, F, *M, W, Y, A* |
| B27 | R, H, K | | F, Y, L, *W, M, I, V, A* |
| B44 | E, *D* | | F, W, L, I, M, V, A |
| B58 | A, T, S | | F, W, Y, *L, I, V, M, A* |
| B62 | Q, L, *I, V, M, P* | | F, W, Y, *M, I, V, L, A* |
| MOTIFS | | | |
| A1 | T, S, M | | Y |
| A1 | | D, E, *A, S* | Y |
| A2.1 | L, M, *V, Q, I, A, T* | | V, *L, I, M, A, T* |
| A3 | L, M, V, I, S, A, *T, F, C, G, D* | | K, Y, R, *H, F, A* |
| A11 | V, T, M, L, I, S, *A, G, N, C, D, F* | | K, *R, Y, H* |
| A24 | Y, F, W, *M* | | F, L, I, W |
| A*3101 | M, V, T, *A, L, I, S* | | R, *K* |
| A*3301 | M, V, A, L, F, *I, S, T* | | R, K |
| A*6801 | A, V, T, *M, S, L, I* | | R, K |
| B*0702 | P | | L, M, F, *W, Y, A, I, V* |
| B*3501 | P | | L, M, F, W, Y, *I, V, A* |
| B51 | P | | L, I, V, F, *W, Y, A, M* |
| B*5301 | P | | I, M, F, W, Y, *A, L, V* |
| B*5401 | P | | A, T, I, V, *L, M, F, W, Y* |

Bolded residues are preferred, italicized residues are less preferred: A peptide is considered motif-bearing if it has primary anchors at each primary anchor position for a motif or supermotif as specified in the above table.

TABLE 4

| SUPER-MOTIFS | POSITION 2 (Primary Anchor) | POSITION 3 (Primary Anchor) | POSITION C Terminus (Primary Anchor) |
|---|---|---|---|
| A1 | T, I, *L, V, M, S* | | F, W, *Y* |
| A2 | V, *Q, A, T* | | I, V, *L, M, A, T* |
| A3 | V, S, M, A, *T, L, I* | | R, K |
| A24 | Y, F, *W, I, V, L, M, T* | | F, I, *Y, W, L, M* |
| B7 | P | | V, I, L, F, *M, W, Y, A* |
| B27 | R, H, K | | F, Y, L, *W, M, I, V, A* |
| B58 | A, T, S | | F, W, Y, *L, I, V, M, A* |
| B62 | Q, L, *I, V, M, P* | | F, W, Y, *M, I, V, L, A* |
| MOTIFS | | | |
| A1 | T, S, M | | Y |
| A1 | | D, E, *A, S* | Y |
| A2.1 | *V, Q, A, T*\* | | V, *L, I, M, A, T* |
| A3.2 | L, M, V, I, S, A, *T, F, C, G, D* | | K, Y, R, *H, F, A* |
| A11 | V, T, M, L, I, S, *A, G, N, C, D, F* | | K, *R, H, Y* |
| A24 | Y, F, W | | F, L, I, W |

*If 2 is V, or Q, the C-term is not L

Bolded residues are preferred, italicized residues are less preferred: A peptide is considered motif-bearing if it has primary anchors at each primary anchor position for a motif or supermotif as specified in the above table.

TABLE 5

Allele-specific HLA-supertype members

| HLA-supertype | Verified[a] | Predicted[b] |
|---|---|---|
| A1 | A*0101, A*2501, A*2601, A*2602, A*3201 | A*0120, A*2604, A*3601, A*4301, A*8001 |
| A2 | A*0201, A*0202, A*0203, A*0204, A*0205, A*0206, A*0207, A*0209, A*0214, A*6802, A*6901 | A*0208, A*0210, A*0211, A*0212, A*0213 |
| A3 | A*0301, A*1101, A*3101, A*3301, A*6801 | A*0302, A*1102, A*2603, A*3302, A*3303, A*3401, A*3402, A*6601, A*6602, A*7401 |
| A24 | A*2301, A*2402, A*3001 | A*2403, A*2404, A*3002, A*3003 |
| B7 | B*0702, B*0703, B*0704, B*0705, B*1508, B*3501, B*3502, B*3503, B*3503, B*3504, B*3505, B*3506, B*3507, B*3508, B*5101, B*5102, B*5103, B*5104, B*5105, B*5301, B*5401, B*5501, B*5502, B*5601, B*5602, B*6701, B*7801 | B*1151, B*4201, B*5901 |
| B27 | B*1401, B*1402, B*1509, B*2702, B*2703, B*2704, B*2705, B*2706, B*3801, B*3901, B*3902, B*7301 | B*2701, B*2707, B*2708, B*3802, B*3903, B*3904, B*3905, B*4801, B*4802, B*1510, B*1518, B*1503 |
| B44 | B*1801, B*1802, B*3701, B*4402, B*4403, B*4404, B*4001, B*4002, B*4006 | B*4101, B*4501, B*4701, B*4901, B*5001 |
| B58 | B*5701, B*5702, B*5801, B*5802, B*1516, B*1517 | |
| B62 | B*1501, B*1502, B*1513, B*5201 | B*1301, B*1302, B*1504, B*1505, B*1506, B*1507, B*1515, B*1520, B*1521, B*1512, B*1514, B*1510 |

[a]Verified alleles include alleles whose specificity has been determined by pool sequencing analysis, peptide binding assays, or by analysis of the sequences of CTL epitopes.
[b]Predicted alleles are alleles whose specificity is predicted on the basis of B and F pocket structure to overlap with the supertype specificity.

TABLE 6

Characterization of heterocyclic analogs identified from tumor and viral antigens.

| Antigen | SEQ ID NO: | Sequence | Heterocyclic substitution | Type of substitution | Position of substitution | Th1 cytokines[a] | Th2 cytokines[b] | A*0201 binding (IC50, nM)[d] |
|---|---|---|---|---|---|---|---|---|
| CEA.691 | 1 | IMIGVLVGV | None (WT) | None | | 1 | 10 | 54 |
| CEA.691 M3 | 2 | IMMGVLVGV | I→M | Conservative | 3 | $10^{-5}$ | 1 | 27 |
| CEA.691 H5 | 3 | IMIGHLVGV | V→H | Semi-conservative | 5 | $10^{-7}$ | $10^{-1}$ | 16 |
| MAGE3.112 | 4 | KVAELVHFL | None (WT) | None | | 1 | NS[c] | 94 |
| MAGE3.112 I5 | 5 | KVAEIVHFL | L→I | Conservative | 5 | $10^{-4}$ | NS | 66 |

TABLE 6-continued

Characterization of heterocyclic analogs identified from tumor and viral antigens.

| Antigen | SEQ ID NO: | Sequence | Heterocyclic substitution | Type of substitution | Position of substitution | Th1 cytokines[a] | Th2 cytokines[b] | A*0201 binding (IC50, nM)[d] |
|---|---|---|---|---|---|---|---|---|
| MAGE3.112 W7 | 6 | KVAELVWFL | H→W | Semi-conservative | 7 | $10^{-7}$ | NS | 7 |
| MAGE2.157 | 7 | YLQLVFGIEV | None (WT) | None | | 1 | 10 | 40 |
| MAGE2.157 I5 | 8 | YLQLIFGIEV | V→I | Conservative | 5 | $10^{-4}$ | $10^{-2}$ | 476 |
| MAGE2.157 F5 | 9 | YLQLFFGIEV | V→F | Semi-conservative | 5 | $10^{-2}$ | $10^{-2}$ | 212 |
| HBV Pol.455 | 16 | GLSRYVARL | None (WT) | None | | 10 | 10 | 83 |
| HBV Pol.455 P7 | 17 | GLSRYVPRL | A→P | Conservative | 7 | $10^{-2}$ | $10^{-2}$ | 267 |
| HIV Pol.476 | 18 | ILKEPVHGV | None (WT) | | | >10 | >10 | 369 |
| HIV Pol.476 H3 | 19 | ILHEPVHGV | K→H | Conservative | 3 | 1 | 1 | 78 |
| HIV Pol.476 L3 | 20 | ILLEPVHGV | K→L | Semi-conservative | 3 | $10^{-1}$ | 1 | 63 |

[a]Minimum peptide concentration (μg/ml) required to induce 100 pg/well of IFNγ (Th1 cytokines)
[b]Minimum peptide concentration (μg/ml) required to induce 50 pg/ml of IL10 or IL15 (Th2 cytokines)
[c]NS, cytokine levels not significant (<5 pg/ml)
[d]A relative binding change of four-fold or more compared to wildtype peptide is considered significant and is indicated in bold

TABLE 7

Summary of heteroclitic analogs of MAGE2.170

| Antigen | Heteroclitic substitution | Type of substitution | Position of Substitution | B*0702 binding (IC50, nM) | SEQ ID NO: |
|---|---|---|---|---|---|
| MAGE2.170 | None (WT) | None | | 112 | SEQ ID NO:48 |
| MAGE2.170H7 | Y --> H | Semi-conservative | 7 | 75 | SEQ ID NO:49 |
| MAGE2.170M7 | Y --> M | Semi-conservative | 7 | 69 | SEQ ID NO:50 |
| MAGE2.170G7 | Y --> G | Non-conservative | 7 | 105 | SEQ ID NO:51 |
| MAGE2.170E7 | Y --> E | Non-conservative | 7 | 186 | SEQ ID NO:52 |
| MAGE2.170D7 | Y --> D | Non-conservative | 7 | 1276 | SEQ ID NO:53 |

What is claimed is:

1. A method of producing a polypeptide of 9 to 20 amino acids in length comprising a heteroclitic analog of a Major Histocompatibility Complex (MHC) class I immunogenic epitope, wherein said heteroclitic analog has enhanced immunogenicity compared to said epitope, said method comprising:

(a) identifying a MT-IC class I immunogenic epitope from a protein antigen comprising a formula (A), wherein formula (A) is Rn-R2-R3-R4-R5-R6-R7- . . . Rx, Rn is the N-terminal amino acid, Rx is the C-terminal amino acid, x=8-11 such that Rx can be from the eighth to the eleventh amino acid residue from Rn, R2 is a primary anchor residue of an A2 supermotif selected from the group consisting of L, I, V, M, A, T and Q, Rx is a primary anchor residue of an A2 supermotif selected from the group consisting of L, I, V, M, A and T, and (b) designing predicted analogs of said epitope having a formula (B) identical to said formula (A) except having one or more conservative or semi-conservative amino acid substitutions, in comparison to the original amino acid(s) at only R3 and/or R5 and/or R7, (c) producing the predicted analogs of step (b) by introducing one or more conservative or semi-conservative amino acid substitutions, in comparison to the original amino acid(s) at only R3 and/or R5 and/or R7, wherein if said residue of said epitope is A, said conservative amino acid of said analog is S, T, P or G; if said residue of said epitope is C, said conservative amino acid of said analog is V, T, or A; if said residue of said epitope is D, said conservative amino acid of said analog is N, E, or Q; if said residue of said epitope is E, said conservative amino acid of said analog is Q, N, D, or H; if said residue of said epitope is F; said conservative amino acid of said analog is L, Y, I, M or V; if said residue of said epitope is G; said conservative amino acid of said analog is S, A, T, D or P; if said residue of said epitope is H; said conservative amino acid of said analog is Q, E, or N; if said residue of said epitope is I; said conservative amino acid of said analog is L, M, F, or V; if said residue of said epitope is K; said conservative amino acid of said analog is R, Q, or H; if said residue of said epitope is L; said conservative amino acid of said analog is I, M, F, or V; if said residue of said epitope is M; said conservative amino acid of said analog is L, I, V, or F; if said residue of said epitope is N; said conservative amino acid of said analog is D, E, Q, or H; if said residue of said epitope is P; said conservative amino acid of said analog is T, S, or A; if said residue of said epitope is Q; said conservative amino acid of said analog is E, H, N, or K; if said residue of said epitope is R; said conservative amino acid of said analog is K, H, or Q; if said residue of said epitope is S; said conservative amino acid of said analog is T, G, A, P or N; if said residue of said epitope is T; said conservative amino acid of said analog is P, S, A, or N; if said residue of said epitope is V; said conservative amino acid of said analog is L, I, or M; if said residue of said epitope is W; said conservative amino acid of said analog is F, Y, L, or M; and if said residue of said epitope is Y, said conservative amino acid of said analog is F or W; and wherein if said residue of said epitope is A, said semi-conservative amino acid of said analog is C, V, D, M, N, E, Q, H, or Y; if said residue of said epitope is C, said semi-conservative amino acid of said analog is S, P, I, Y, N, F, G, M, H, or D; if said residue of said epitope is D, said semi-conservative amino acid of said analog is T, S, H, G, P, A, K, R, or C; if said residue of said epitope is E, said semi-conservative amino acid of said analog is T, K, P, R, S, V, G, A, or M; if said residue of said epitope is F, said semi-conservative amino acid of said analog is W, H, C, T, R, or A; if said residue of said epitope is G, said semi-conservative amino acid of said analog is N, E, Q, H, C, or V; if said residue of said epitope is H, said semi-conservative amino acid of said analog is R, K, P, D, S, T, Y, M, or V; if said residue of said epitope is 1, said semi-conservative amino acid of said analog is Y, T, H, A, C, K, P, Q, or R; if said residue of said epitope is K, said semi-conservative amino acid of said analog is N, E, D, M, T, S, P, I, L, or Y; if said residue of said epitope is L, said semi-conservative amino acid of said analog is Y, H, Q, W, T, A, K, or P; if said residue of said epitope is M, said semi-conservative amino acid of said analog is K, Q, R, Y, H, A, T, P, W, or C; if said residue of said epitope is N, said semi-conservative amino acid of said analog is T, S, K, P, R, A, G, or V; if said residue of said epitope is P, said semi-conservative amino acid of said analog is H, Q, N, D, E, G, V, C, or M; if said residue of said epitope is Q, said semi-conservative amino acid of said analog is D, R, P, M, T, V, S, or A; if said residue of said epitope is R, said semi-conservative amino acid of said analog is E, N, M, D, P, W, S, T, I, L, or Y; if said residue of said epitope is S, said semi-conservative amino acid of said analog is D, C, E, H, Q, or K; if said residue of said epitope is T, said semi-conservative amino acid of said analog is D, E, G, H, Q, V, C, K, or M; if said residue of said epitope is V, said semi-conservative amino acid of said analog is P, T, F, A, C, H, Q, E, N, or S; if said residue of said epitope is W, said semi-conservative amino acid of said analog is R, I, H, V, K, Q, S, A, P, or T; and if said residue of said epitope is Y, said semi-conservative amino acid of said analog is H, M, L, T, I, C, V, P, A, N, Q, S, K or R;

(d) performing an analysis to identify analogs that render heteroclitic activity to said epitope as measured by an increased ability to elicit a T cell response, and (e) producing a polypeptide of 9 to 20 amino acids in length comprising an analog with heteroclitic activity, wherein said method does not entail screening analogs containing random amino acid substitutions.

2. The method of claim 1, wherein said analog exhibits at least 50% increased potency for a specific T-cell compared to said epitope.

3. The method of claim 1, wherein only one substitution is introduced.

4. The method of claim 3, wherein the substitution is a conservative substitution.

5. The method of claim 3, wherein the substitution is a semi-conservative substitution.

6. The method of claim 1, wherein the peptide comprising said analog induces both Th1 and Th2 cytokines when said analog is bound by an HLA Class I molecule and contacted with a cytotoxic T lymphocyte (CTL).

7. The method of claim 1, wherein said epitope is derived from a viral antigen, a tumor-associated antigen, a parasitic antigen, a bacterial antigen or a fungal antigen.

8. A method of producing a polypeptide of 9 to 20 amino acids in length comprising a heteroclitic analog of a Major Histocompatibility Complex (MHC) class I immunogenic epitope, wherein said heteroclitic analog has enhanced immunogenicity compared to said epitope, said method consisting of:

(a) identifying a MHC class I immunogenic epitope from a protein antigen comprising a formula (A), wherein formula (A) is Rn-R2-R3-R4-R5-R6-R7- . . . Rx, Rn is the N-terminal amino acid, Rx is the C-terminal amino acid, x=8-11 such that Rx can be from the eighth to the eleventh amino acid residue from Rn, R2 is a primary anchor residue of an A2 supermotif selected from the group consisting of L, I, V, M, A, T and Q, Rx is a primary anchor residue of an A2 supermotif selected from the group consisting of L, I, V, M, A and T, and (b) designing predicted analogs of said epitope having a formula (B) identical to said formula (A) except having one or more conservative or semi-conservative amino acid substitutions, in comparison to the original amino acid(s) at only R3 and/or R5 and/or R7, (c) producing the predicted analogs of step (b) by introducing one or more conservative or semi-conservative amino acid substitutions, in comparison to the original amino acid(s) at only R3 and/or R5 and/or R7, wherein if said residue of said epitope is A, said conservative amino acid of said analog is S, T, P or G; if said residue of said epitope is C, said conservative amino acid of said analog is V, T, or A; if said residue of said epitope is D, said conservative amino acid of said analog is N, E, or Q; if said residue of said epitope is E, said conservative amino acid of said analog is Q, N, D, or H; if said residue of said epitope is F; said conservative amino acid of said analog is L, Y, I, M or V; if said residue of said epitope is G; said conservative amino acid of said analog is S, A, T, D or P; if said residue of said epitope is H; said conservative amino acid of said analog is Q, E, or N; if said residue of said epitope is I; said conservative amino acid of said analog is L, M, F, or V; if said residue of said epitope is K; said conservative amino acid of said analog is R, Q, or H; if said residue of said epitope is L; said conservative amino acid of said analog is I, M, F, or V; if said residue of said epitope is M; said conservative amino acid of said analog is L, I, V, or F; if said residue of said epitope is N; said conservative amino acid of said analog is D, E, Q, or H; if said residue of said epitope is P; said conservative amino acid of said analog is T, S, or A; if said residue of said epitope is Q; said conservative amino acid of said analog is E, H, N, or K; if said residue of said epitope is R; said conservative amino acid of said analog is K, H, or Q; if said residue of said epitope is S; said conservative amino acid of said analog is T, G, A, P or N; if said residue of said epitope is T; said conservative amino acid of said analog is P, S, A, or N; if said residue of said epitope is V; said conservative amino acid of said analog is L, I, or M; if said residue of said epitope is W; said conservative amino acid of said analog is F, Y, L, or M; and if said residue of said epitope is Y, said conservative amino acid of said analog is F or W; and wherein if said residue of said epitope is A, said semi-conservative amino acid of said analog is C, V, D, M, N, E, Q, H, or Y; if said residue of said epitope is C, said semi-conservative amino acid of said analog is S, P, I, Y, N, F, G, M, H, or D; if said residue of said epitope is D, said semi-conservative amino acid of said analog is T, S, H, G, P, A, K, R, or C; if said residue of said epitope is E, said semi-conservative amino acid of said analog is T, K, P, R, S, V, G, A, or M; if said residue of said epitope is F, said semi-conservative amino acid of said analog is W, H, C, T, R, or A; if said residue of said epitope is G, said semi-conservative amino acid of said analog is N, E, Q, H, C, or V; if said residue of said epitope is H, said semi-conservative amino acid of said analog is R, K, P, D, S, T, Y, M, or V; if said residue of said epitope is I, said semi-conservative amino acid of said analog is Y, T, H, A, C, K, P, Q, or R; if said residue of said epitope is K, said semi-conservative amino acid of said analog is N, E, D, M, T, S, P, I, L, or Y; if said residue of said epitope is L, said semi-conservative amino acid of said analog is Y, H, Q, W, T, A, K, or P; if said residue of said epitope is M, said semi-conservative amino acid of said analog is K, Q, R, Y, H, A, T, P, W, or C; if said residue of said epitope is N, said semi-conservative amino acid of said analog is T, S, K, P, R, A, G, or V; if said residue of said epitope is P, said semi-conservative amino acid of said analog is H, Q, N, D, E, G, V, C, or M; if said residue of said epitope is Q, said semi-conservative amino acid of said analog is D, R, P, M, T, V, S, or A; if said residue of said epitope is R, said semi-conservative amino acid of said analog is E, N, M, D, P, W, S, T, I, L, or Y; if said residue of said epitope is S, said semi-conservative amino acid of said analog is D, C, E, H, Q, or K; if said residue of said epitope is T, said semi-conservative amino acid of said analog is D, E, G, H, Q, V, C, K, or M; if said residue of said epitope is V, said semi-conservative amino acid of said analog is P, T, F, A, C, H, Q, E, N, or S; if said residue of said epitope is W, said semi-conservative amino acid of said analog is R, I, H, V, K, Q, S, A, P, or T; and if said residue of said epitope is Y, said semi-conservative amino acid of said analog is H, M, L, T, I, C, V, P, A, N, Q, S, K or R;

(d) performing an analysis to identify analogs that render heteroclitic activity to said epitope as measured by an increased ability to elicit a T cell response, and (e) producing a polypeptide of 9 to 20 amino acids in length comprising an analog with heteroclitic activity.

9. The method of claim 1, wherein the increased ability of heteroclitic analogs to elicit a T cell response is tested by inducing a primary cytotoxic T lymphocyte (CTL) response from a responder cell in a primary in vitro induction system.

10. The method of claim 8, wherein peripheral blood mononuclear cells (PBMCs) are the responder cell source of the primary CTL.

11. The method of claim 8, wherein the increased ability of heteroclitic analogs to elicit a T cell response is tested by inducing a primary CTL response from a responder cell in a primary in vitro induction system.

12. The method of claim 11, wherein PBMCs are the responder cell source of the primary CTL.

* * * * *